(12) United States Patent
Miller et al.

(10) Patent No.: US 7,091,481 B2
(45) Date of Patent: Aug. 15, 2006

(54) METHOD AND APPARATUS FOR PLASMA GENERATION

(75) Inventors: Raanan A. Miller, Chestnut Hill, MA (US); Erkinjon G. Nazarov, Lexington, MA (US); Evgeny Krylov, Las Cruces, NM (US); Gary A. Eiceman, Las Cruces, NM (US); John A. Wright, Billerica, MA (US); Stephen D. Kendig, Carlisle, MA (US); C. James Morris, Norfolk, MA (US); Douglas B. Cameron, Wellesley, MA (US)

(73) Assignee: Sionex Corporation, Bedford, MA (US)

(*) Notice: Subject to any disclaimer, the term of this patent is extended or adjusted under 35 U.S.C. 154(b) by 96 days.

(21) Appl. No.: 10/894,861

(22) Filed: Jul. 19, 2004

(65) Prior Publication Data

US 2005/0121607 A1    Jun. 9, 2005

Related U.S. Application Data

(63) Continuation-in-part of application No. 10/215,251, filed on Aug. 7, 2002.

(60) Provisional application No. 60/520,284, filed on Nov. 14, 2003, provisional application No. 60/518,367, filed on Nov. 8, 2003, provisional application No. 60/498,093, filed on Aug. 27, 2003, provisional application No. 60/498,163, filed on Aug. 27, 2003, provisional application No. 60/488,019, filed on Jul. 17, 2003, provisional application No. 60/388,052, filed on Jun. 12, 2002, provisional application No. 60/340,815, filed on Dec. 12, 2001, provisional application No. 60/335,219, filed on Oct. 25, 2001, provisional application No. 60/310,902, filed on Aug. 8, 2001.

(51) Int. Cl.
*B01D 59/44* (2006.01)

(52) U.S. Cl. .................... 250/288; 250/286

(58) Field of Classification Search ............. 250/288, 250/286, 287
See application file for complete search history.

(56) References Cited

U.S. PATENT DOCUMENTS 2,615,135 A    10/1952    Glenn (Continued)

FOREIGN PATENT DOCUMENTS

RU    1627984 A2    7/1988

(Continued)

OTHER PUBLICATIONS

"A Micromachined Field Driven Radio Ffrequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

(Continued)

*Primary Examiner*—Kiet T. Nguyen
(74) *Attorney, Agent, or Firm*—Fish & Neave IP Group Ropes & Gray LLP

(57) ABSTRACT

An RF-driven plasma source, including a pair of spaced-apart plasma electrodes, wherein the electrodes act as plates of a capacitor, the gas electrically discharges and creates a plasma of both positive and negative ions, in a clean process that enables efficient sample analysis, with preferred isolated sample photo-ionization, reduced-power operation and also including signal detection with modulated drive electronics.

71 Claims, 46 Drawing Sheets

U.S. PATENT DOCUMENTS

| | | | |
|---|---|---|---|
| 2,818,507 | A | 12/1957 | Britten |
| 2,919,348 | A | 12/1959 | Bierman |
| 3,511,986 | A | 5/1970 | Llewellyn |
| 3,619,605 | A | 11/1971 | Cook et al. |
| 3,621,240 | A | 11/1971 | Cohen et al. |
| 3,931,589 | A | 1/1976 | Aisenberg et al. |
| 4,019,989 | A | 4/1977 | Hazewindus et al. |
| 4,025,818 | A | 5/1977 | Giguere et al. |
| 4,136,280 | A | 1/1979 | Hunt et al. |
| 4,163,151 | A | 7/1979 | Bayless et al. |
| 4,201,921 | A | 5/1980 | McCorkle |
| 4,315,153 | A | 2/1982 | Vahrenkamp |
| 4,517,462 | A | 5/1985 | Boyer et al. |
| 4,577,461 | A | 3/1986 | Cann |
| 4,761,545 | A | 8/1988 | Marshall et al. |
| 4,931,640 | A | 6/1990 | Marshall et al. |
| 5,019,706 | A | 5/1991 | Allemann et al. |
| 5,144,127 | A | 9/1992 | Williams et al. |
| 5,218,203 | A | 6/1993 | Eisele et al. |
| 5,298,745 | A | 3/1994 | Kernan et al. |
| 5,420,424 | A | 5/1995 | Carnahan et al. |
| 5,455,417 | A | 10/1995 | Sacristan |
| 5,479,815 | A | 1/1996 | White et al. |
| 5,492,867 | A | 2/1996 | Kotvas et al. |
| 5,508,204 | A | 4/1996 | Norman |
| 5,536,939 | A | 7/1996 | Freidhoff et al. |
| 5,541,408 | A | 7/1996 | Sittler |
| 5,654,544 | A | 8/1997 | Dresch |
| 5,723,861 | A | 3/1998 | Carnahan et al. |
| 5,736,739 | A | 4/1998 | Uber et al. |
| 5,763,876 | A | 6/1998 | Perinarides et al. |
| 5,789,745 | A | 8/1998 | Martin et al. |
| 5,801,379 | A | 9/1998 | Kouznetsov |
| 5,811,059 | A | 9/1998 | Genovese et al. |
| 5,834,771 | A | 11/1998 | Yoon et al. |
| 5,838,003 | A | 11/1998 | Bertsch et al. |
| 5,846,331 | A | 12/1998 | Miyamoto |
| 5,869,344 | A | 2/1999 | Linforth et al. |
| 5,965,882 | A | 10/1999 | Megerle et al. |
| 5,998,788 | A | 12/1999 | Breit |
| 6,035,101 | A | 3/2000 | Sajoto et al. |
| 6,051,832 | A | 4/2000 | Bradshaw |
| 6,055,151 | A | 4/2000 | Tormey et al. |
| 6,066,848 | A | 5/2000 | Kassel et al. |
| 6,107,624 | A | 8/2000 | Doring et al. |
| 6,107,628 | A | 8/2000 | Smith et al. |
| 6,124,592 | A | 9/2000 | Spangler |
| 6,180,414 | B1 | 1/2001 | Katzman |
| 6,200,539 | B1 | 3/2001 | Sherman et al. |
| 6,239,428 | B1 | 5/2001 | Kunz |
| 6,323,482 | B1 | 11/2001 | Clemmer et al. |
| 6,407,382 | B1 * | 6/2002 | Spangler ............... 250/286 |
| 6,479,815 | B1 | 11/2002 | Goebel et al. |
| 6,495,823 | B1 | 12/2002 | Miller et al. |
| 6,504,149 | B1 | 1/2003 | Guevremont et al. |
| 6,509,562 | B1 | 1/2003 | Yang et al. |
| 6,512,224 | B1 | 1/2003 | Miller et al. |
| 6,540,691 | B1 | 4/2003 | Philips |
| 6,621,077 | B1 | 9/2003 | Guevremont et al. |
| 6,639,212 | B1 | 10/2003 | Guevremont |
| 6,653,627 | B1 | 11/2003 | Guevremont |
| 6,690,004 | B1 | 2/2004 | Miller et al. |
| 6,703,609 | B1 | 3/2004 | Guevremont |
| 6,713,758 | B1 | 3/2004 | Guevremont |
| 6,753,522 | B1 | 6/2004 | Guevremont |
| 6,770,875 | B1 | 8/2004 | Guevremont |
| 6,774,360 | B1 | 8/2004 | Guevremont |
| 6,787,765 | B1 | 9/2004 | Guevremont |
| 6,799,355 | B1 | 10/2004 | Guevremont |
| 6,806,466 | B1 | 10/2004 | Guevremont |
| 2001/0030285 | A1 | 10/2001 | Miller et al. |
| 2002/0070338 | A1 | 6/2002 | Loboda |
| 2002/0134932 | A1 | 9/2002 | Guevremont et al. |
| 2003/0020012 | A1 | 1/2003 | Guevremont et al. |
| 2003/0038235 | A1 | 2/2003 | Guevremont et al. |
| 2003/0052263 | A1 | 3/2003 | Kaufman et al. |
| 2003/0089847 | A1 | 5/2003 | Guevremont et al. |
| 2003/0132380 | A1 | 7/2003 | Miller et al. |
| 2004/0094704 | A1 | 5/2004 | Miller et al. |

FOREIGN PATENT DOCUMENTS

| | | |
|---|---|---|
| RU | 1412447 A1 | 6/1998 |
| RU | 1405489 A1 | 10/1998 |
| RU | 1485808 | 10/1998 |
| SU | 966583 | 10/1982 |
| SU | 1337934 A2 | 9/1987 |
| WO | WO 96/19822 | 6/1996 |
| WO | WO 97/38302 | 10/1997 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/071053 A | 9/2002 |
| WO | WO 02/083276 A1 | 10/2002 |
| WO | WO 03/005016 A1 | 1/2003 |
| WO | WO 03/015120 A1 | 2/2003 |

OTHER PUBLICATIONS

Barnett, D.A. et al., "Isotope Separation Using High-Field Asymmetric Waveform Ion Mobility Spectrometry," Nuclear Instruments & Methods in Physics Research (2000), pp. 179-185, 450(1).

Buryakov, I.A. et al., "Drift Spectrometer for the Control of Amine Traces in the Atmosphere," J. Analytical Chem. 48(1):156-165 (1993).

Buryakov, I.A. et al., "Separation Ions According to Mobility in a Strong ac electric Field," Sov. Tech. Phs. Lett. (1991), pp. 446-447, 17(6).

Buryakov, I.A. et al., Device and Method For Gas Electrophoresis, Chemical Analysis fo Environment, edit. Prof. V.V. Malakhov, Novosibirsk; Nauka (1991), pp. 113-127.

Buryakov, I.A. et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes (1993), pp. 143-148, 128.

Carnahan, B. et al., "Field Ion Spectrometry—A New Analytical Technology for Trace Gas Analysis," ISA, (1996), pp. 87-96; 51(1).

Carnahan, B. et al., "Field Ion Spectrometry—A New Technology for Cocaine and Heroin Detection," SPIE, (1997), pp. 106-119, 2937.

Eiceman, G.A., et al., "Miniature radio-frequency mobility analyzer as a gas chromatographic detector for oxygen-containing volatile organic compounds, pheromones, and other insect attractants," J. Chromatography, (2001), pp. 205-217, 917.

Guevremont, R. and Purves, R., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R. et al., "Atmospheric Pressure In Focusing in a High-Field Asymmetric Waveform Ion Mobility Spectrometer," Review of Scientific Instruments, (1999), pp. 1370-1383, 70(2).

Handy, Russell et al., "Determination of nanomlar levels of perchlorate in water by ESI-FAIMS-MS," JAAS (2000), pp. 907-911, 15.

Javahery, G. et al., A Segmented Radiofrequency-Only Quadrupole Collision Cell for Measurements of Ion Collision Cross Section on a Triple Quadrupole Mass Spectrometer, J. Am. Soc. Mass. Spectom., (1997), pp. 697-702, 8.

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio-frequency ion mobility spectrometer for chemical vapor detection," Sensors and Actuators, (2001), pp. 301-312, A91.

Miller, R.A. et al., "A Novel Micromachined High-Field Asymmetric Waveform-Ion Mobility Spectrometer," Sensors and Actuators B, (2000) pp. 300-306, B67 (3).

Phillips, M., "Method for the Collection and Assay of Volatile Organic Compounds in Breath," Analytical Biochemistry, 247:272-278 (1997).

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., High Sensitivity GC-FIS for Simultaneous Detection of Chemical Warfare Agents, Mine Safety Appliances Co., Pittsburgh, PA, USA, (2000), AT-Process, pp. 124-136, 5(3,4), CODEN: APJCFR ISSN: 1077-419X.

Shute, L.A. et al., "Curie-point Pyrolysis Mass Spectrometry Applied to Characterization and Identification of Selected Bacillus Species," J. General Micro., (JGMIAN) (1984), pp. 343-355, 130(2).

Verenchikov, A.N. et al., Analysis ions in solutes by gaseous ion analyzer. "Chemical Analysis of the Environmental Objects" red. Mlakhov. Novosibirsk, Nauka, (1991), pp. 127-134.

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

\* cited by examiner

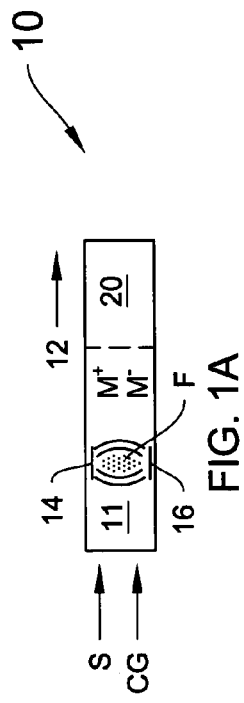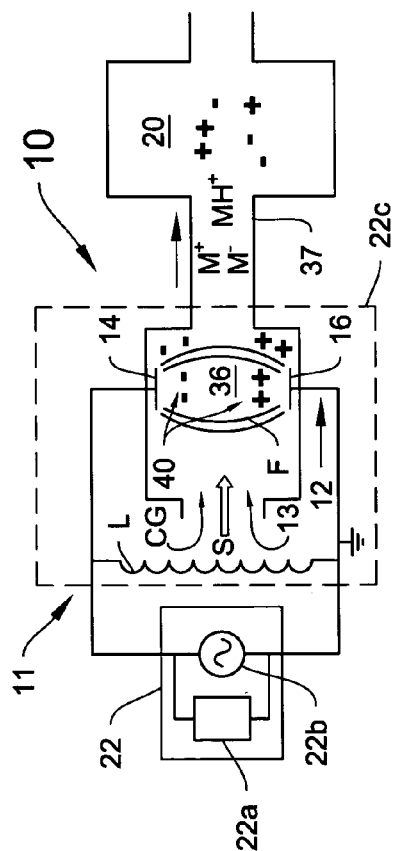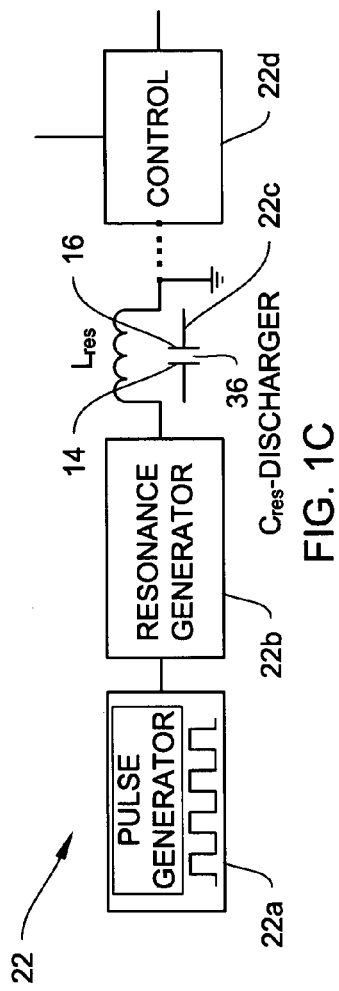

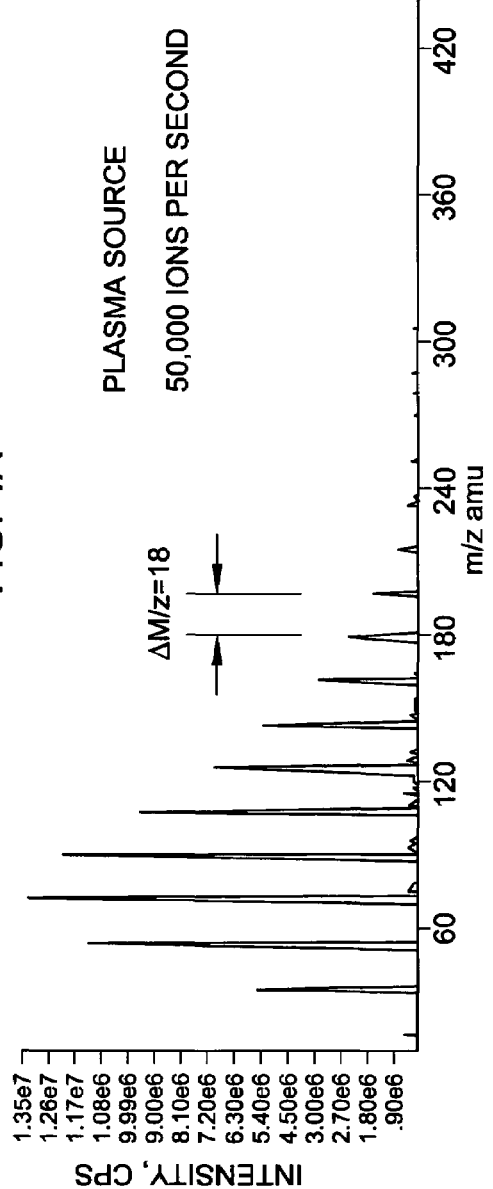
FIG. 4A
FIG. 4B

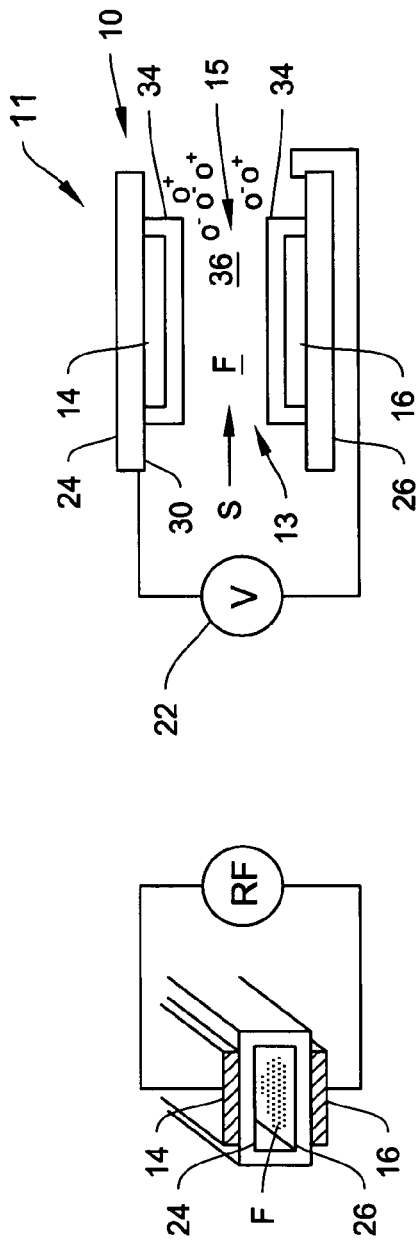
FIG. 13A
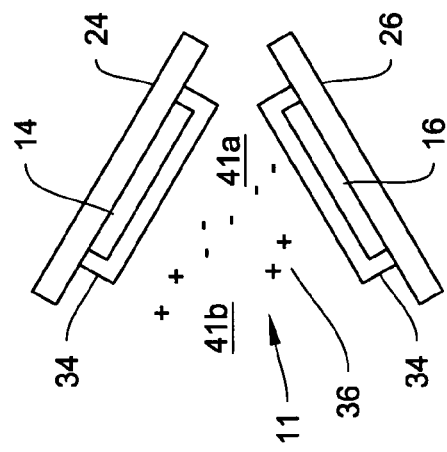
FIG. 13B
FIG. 13C

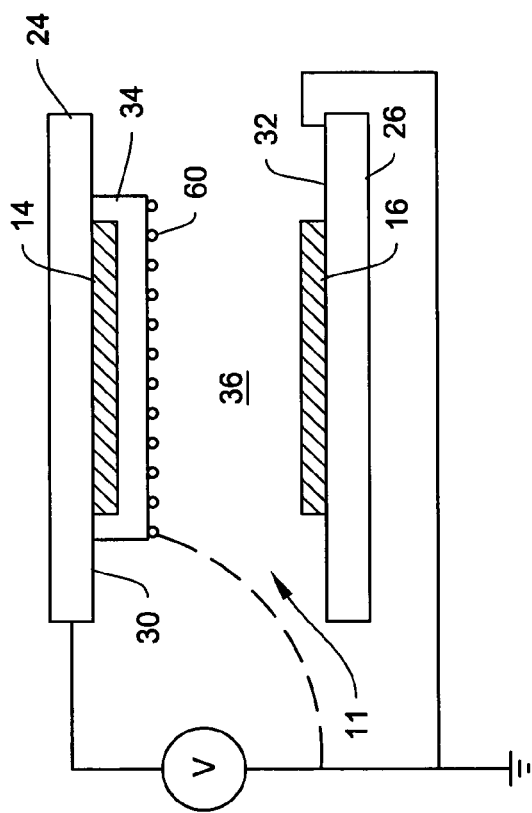
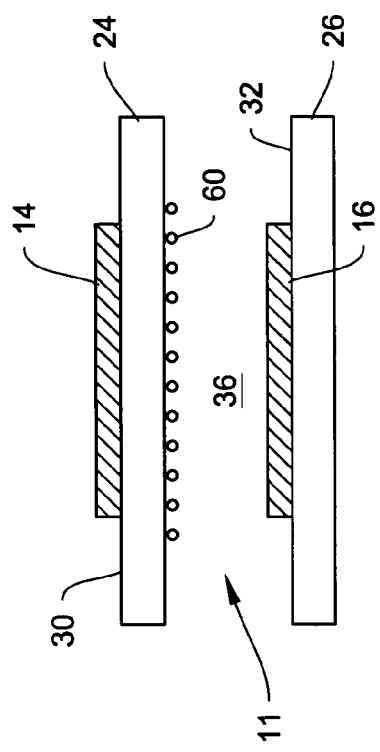
FIG. 13I
FIG. 13J

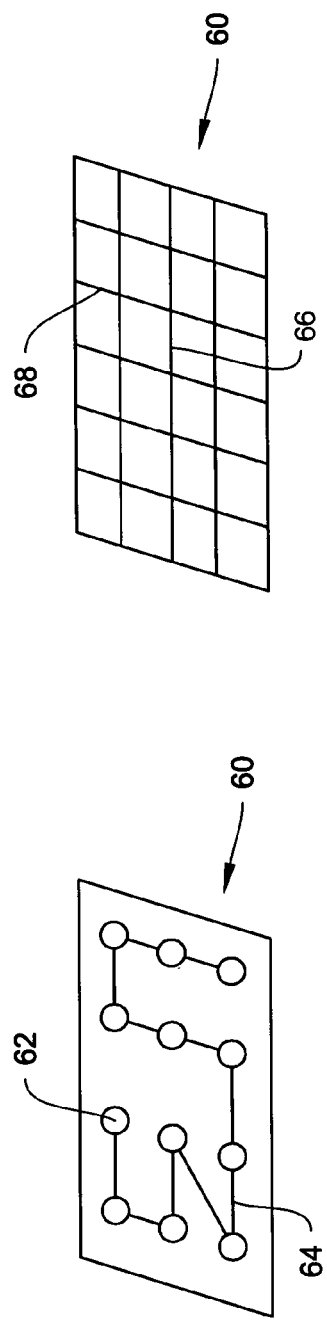

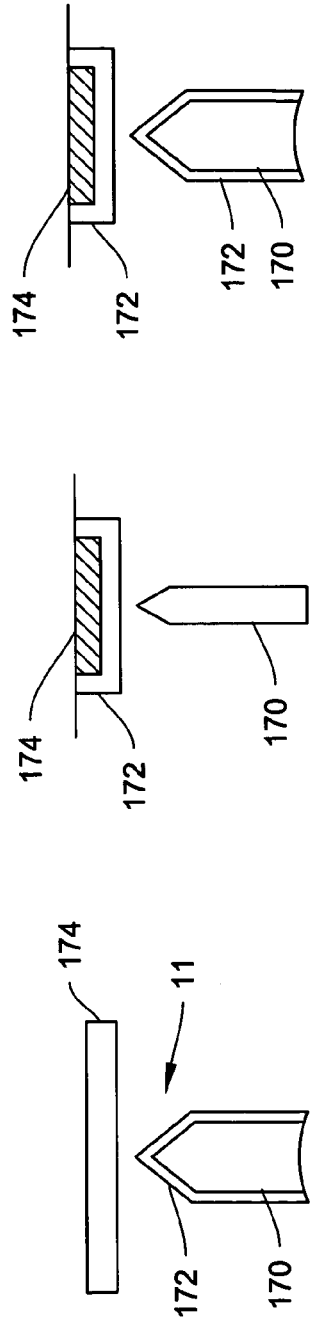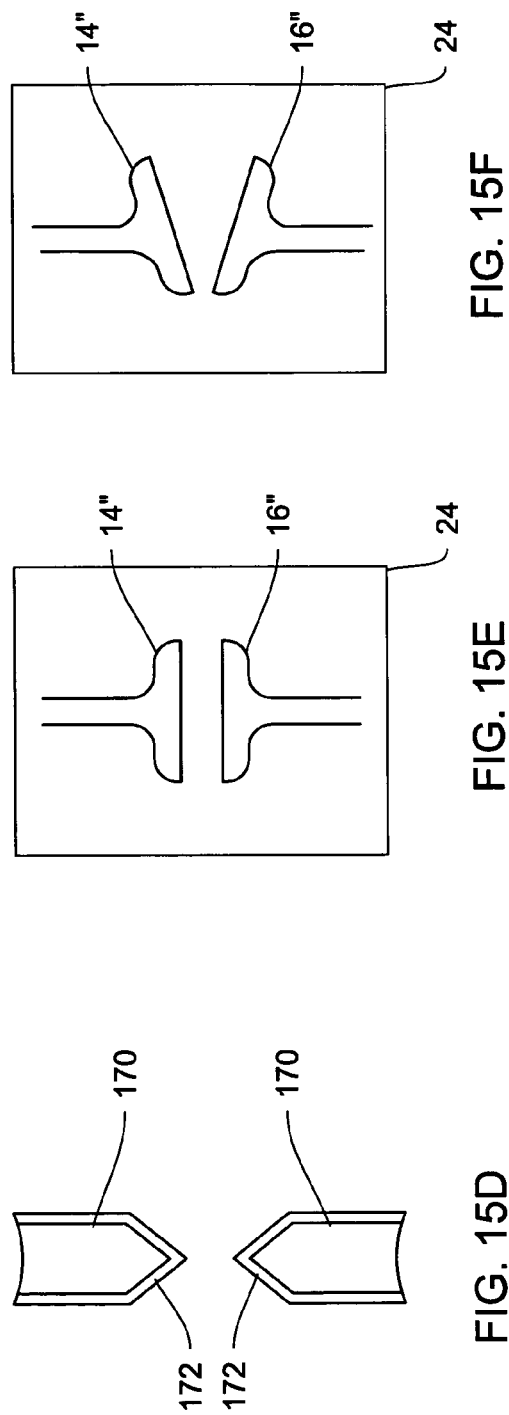

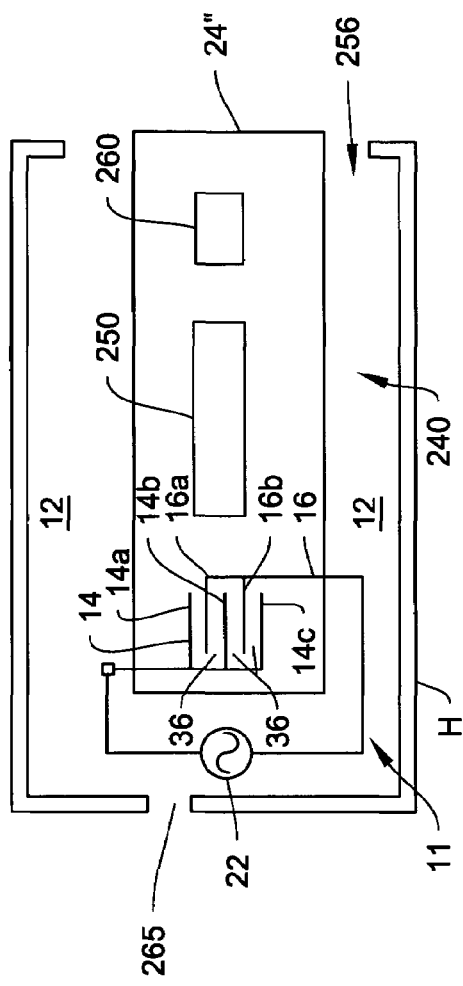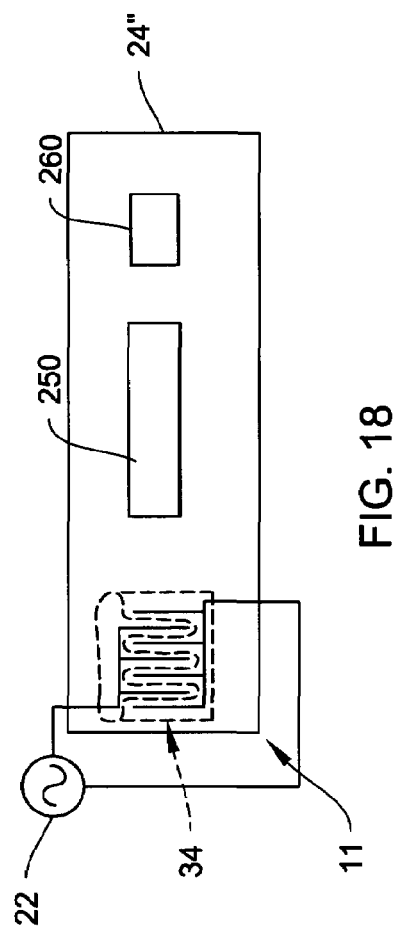

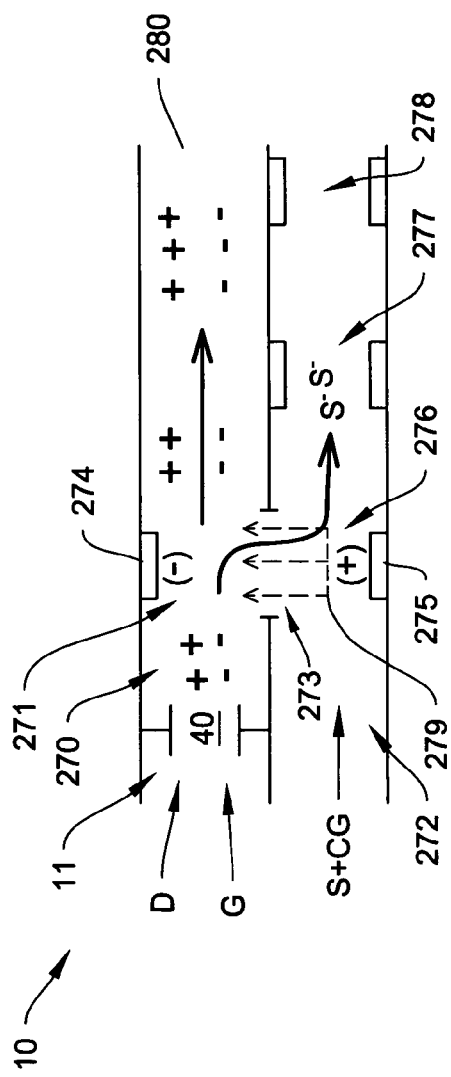
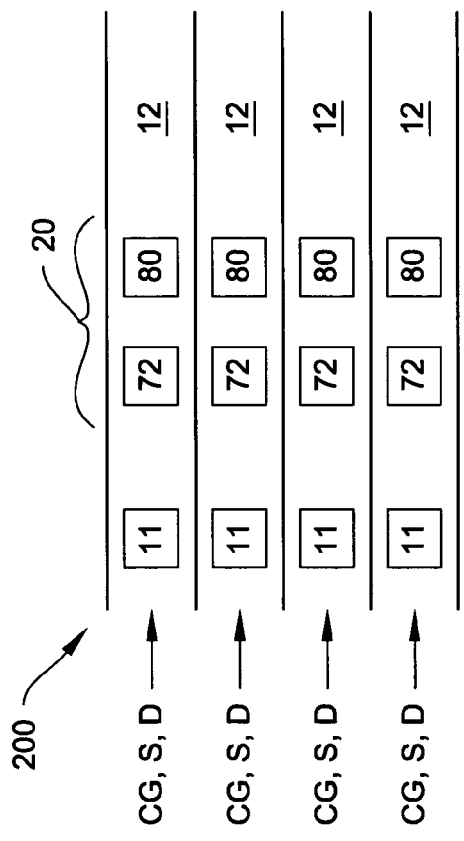
FIG. 20F
FIG. 20G

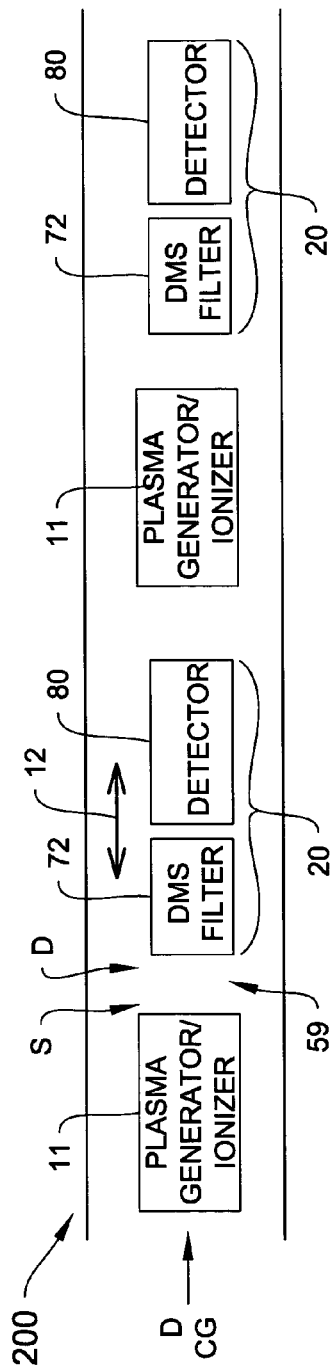
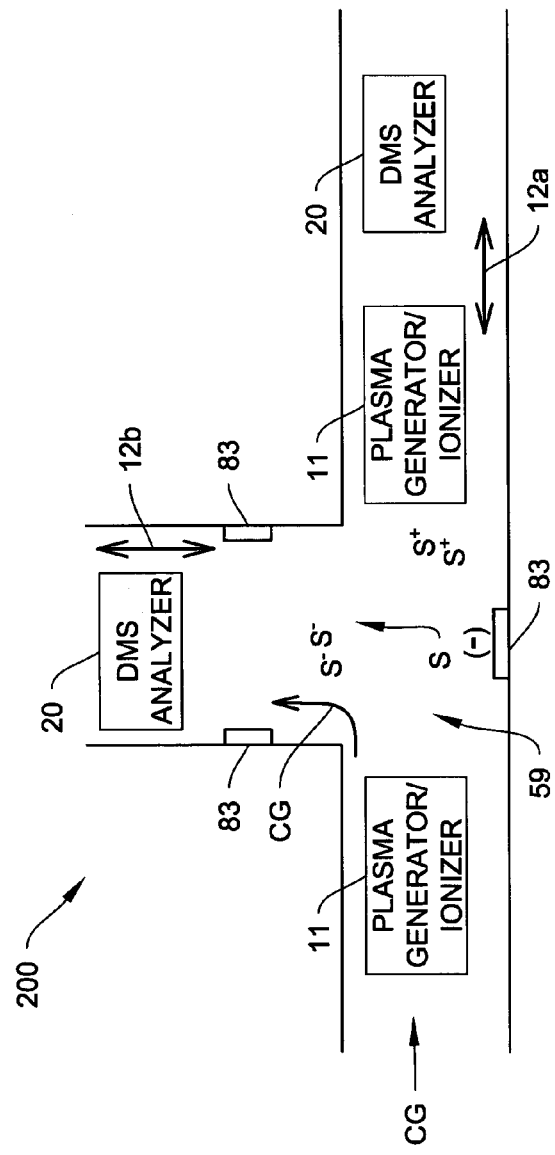
FIG. 20H
FIG. 20I

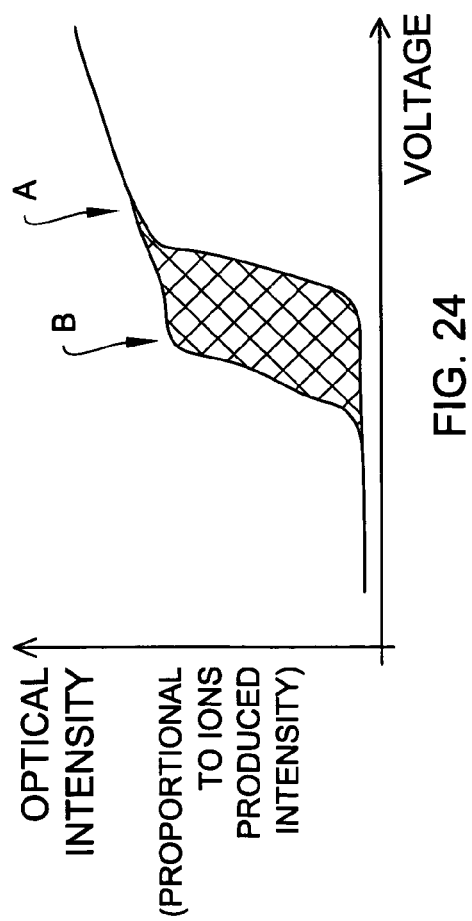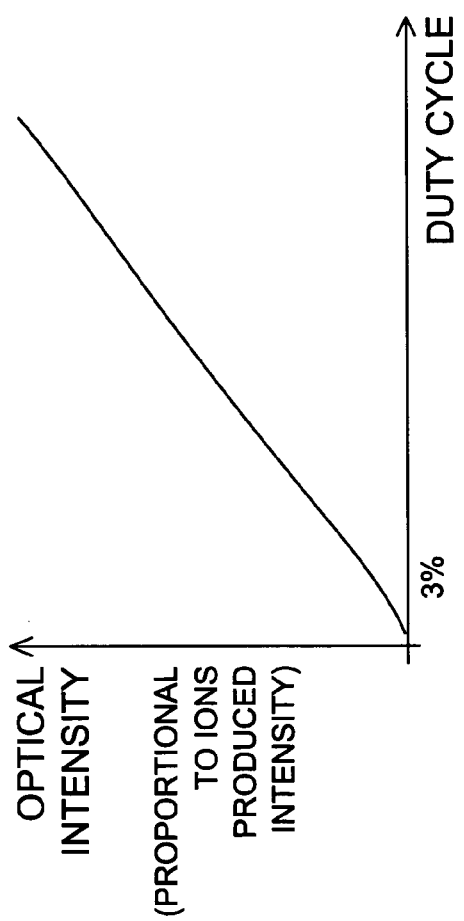

EXAMPLE RF WAVEFORM:
DUTY CYCLE ≈ 20%
FREQ. ≈ 1.2 MHz
VOLTAGE ≈ 1500 $V_{P-P}$

EXAMPLE COMPENSATION
VOLTAGE WAVEFORM (TOP VIEW)

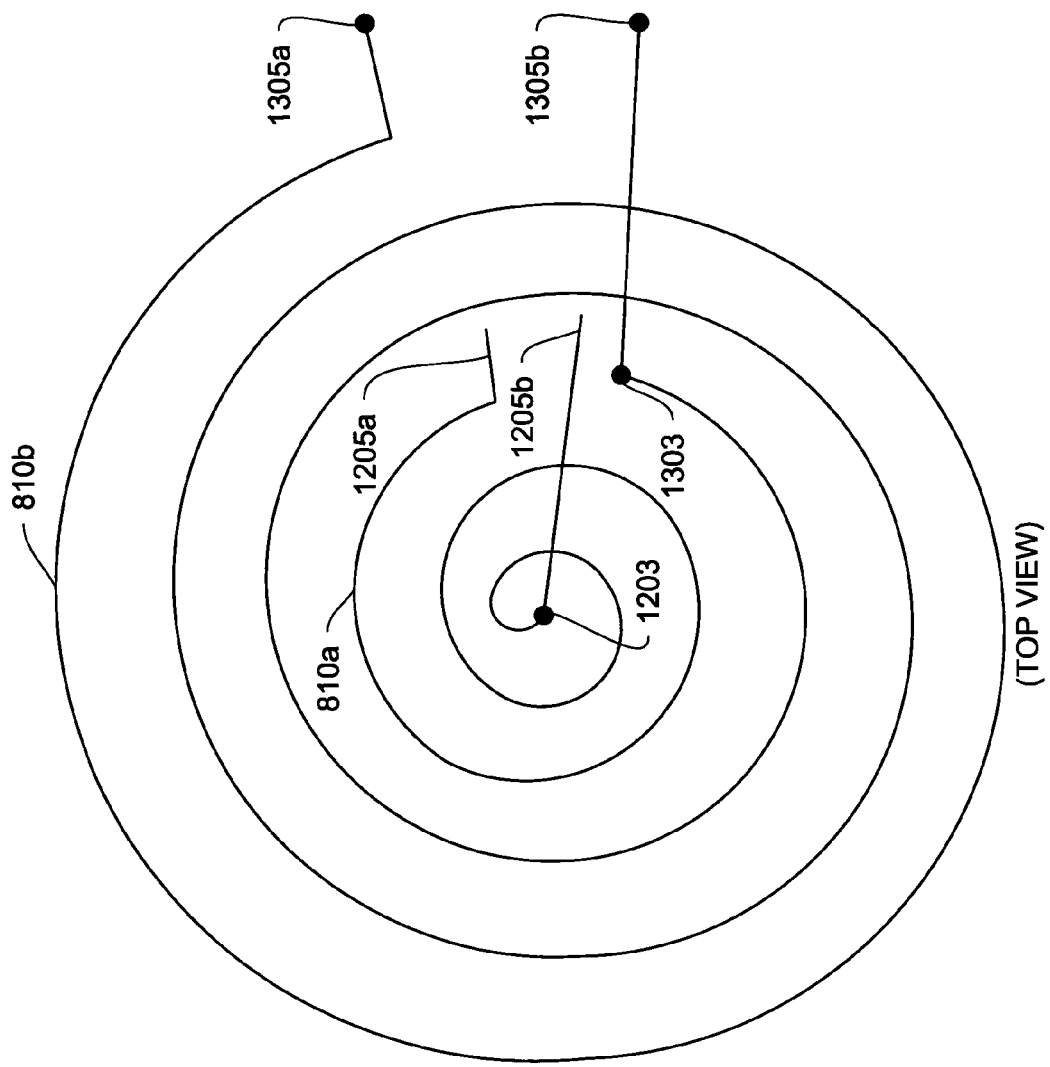

METHOD AND APPARATUS FOR PLASMA GENERATION

REFERENCE TO RELATED APPLICATIONS

This application is a continuation-in-part of U.S. patent application Ser. No. 10/215,251 (filed 7 Aug. 2002). the entire contents of which are incorporated herein by reference, which claims priority to and the benefit of the following applications: U.S. Provisional Patent Application 60/310,902 (filed 8 Aug. 2001): U.S. Provisional Patent Application 60/335,219 (filed 25 Oct. 2001); U.S. Provisional Patent Application 60/340,815 (filed 12 Dec. 2001); and U.S. Provisional Application 60/388,052 (filed 12 Jun. 2002). This application claims priority to and the benefit of, and incorporates by reference, the following applications: U.S. Provisional Patent Application 60/488,019 (filed 17 Jul. 2003); U.S. Provisional Application 60/498,163 (filed 27 Aug. 2003); U.S. Provisional Patent Application 60/498,093 (filed 27 Aug. 2003); and U.S. Provisional Patent Application 60/518,367 (filed 8 Nov. 2003). This application claims priority to and the benefit of U.S. Provisional Patent Application 60/520,284 (filed 14 Nov. 2003).

This application also incorporates herein by reference the entire contents of U.S. patent application Ser. No. 10/462,206 (filed 13 Jun. 2003).

FIELD OF THE INVENTION

The invention relates to an ionization source, and more particularly, in one embodiment, to a plasma generator for atmospheric gas discharge ionization.

BACKGROUND OF THE INVENTION

Creation of ionized particles is a useful tool for many applications, such as for ignition of lasing or to assist chemical analysis, among other uses. In some equipment, high energy radioactive sources of alpha or beta particles are employed for the ionization process. However, because of the potential health hazard and need for regulation, widespread use of equipment using radioactive ionization sources has been limited. And even though smoke alarms use radioactive sources, the amount of ionization is low, and they still require government regulation.

There are several ionization methods that avoid radioactive sources. Corona discharge is a source of non-radioactive ionization. It provides high energy in a compact package. However, this process is not stable and can contaminate the sample with metal ions or NOx, as would interfere with analytical results. Furthermore, the generated ion species depends upon the applied voltage.

RF discharge ionization reduces some of these disadvantageous effects. RF discharges are subdivided into inductive and capacitive discharges, differing in the way the discharge is produced.

Inductive methods are based on electromagnetic induction so that the created electric field is a vortex field with closed lines of force. Inductive methods are used for high-power discharges, such as for production of refractory materials, abrasive powders, and the like.

Capacitive discharge methods are used to maintain RF discharges at moderate pressures $p \sim 1$–$100$ Torr and at low pressures $p \sim 10^{-3}$–$1$ Torr. The plasma in them is weakly ionized and non-equilibrium, like that of a corona discharge. Moderate-pressure discharges have found application in laser technology to excite $CO_2$ lasers, while low-pressure discharges are used for ion treatment of materials and in other plasma technologies.

Another ionization process is UV ionization. This process is sometimes referred to as atmospheric pressure photo-ionization (APPI). In low pressure conditions, photo-ionization involves direct interaction of photons with samples, forming positively charged molecular ions and free electrons. At elevated pressure conditions, the situation is not so simple and the ionization process for sample molecules can include a sequence of gas phase reactions, the details of which depend on the energetic properties of initially formed ions and free electrons (due to direct photo-ionization) and on the nature of the ambient gas.

One disadvantage of UV ionization is that it provides low to moderate ionization energies. This limits the types of molecules that can be ionized. As well, sometimes APPI can give unexpected results. The photons are typically generated in a tube, with the photons passing through a window, and this window material affects efficiency. Also, the surfaces of the UV devices can become contaminated or coated from the ionization product, which can degrade device performance or output intensity. As well, the UV tubes can be delicate and fragile, and hence are generally not suitable to operation in harsh environments or in applications requiring a significant amount of manual handling.

SUMMARY OF THE INVENTION

The invention, in various embodiments, addresses the deficiencies in the prior art by providing reliable non-radioactive ionization sources for various applications. More particularly, in one aspect, the invention provides a capacitive discharge apparatus for generating a stable plasma at pressures including at or around atmospheric pressure.

According to one embodiment, a plasma ionization source of the invention, also referred to as a plasma generator or a plasma ionizer, includes at least two plasma electrodes spaced by an ionization gap. In one practice of the invention, a system includes a capacitive gas discharge plasma generator for generating a plasma and a sample ionizer for ionizing a sample, with the sample ionizer being enabled by the plasma. In one embodiment, the gas is air and the plasma is formed at substantially atmospheric pressure and generates positive and negative ions substantially concurrently.

According to one advantage, the invention reduces or eliminates creation of ions from electrode material, and/or creation of other by-products, which may contaminate plasma ionization and which may impact further processes, such as sample ionization and analysis.

In various practices of the invention, the electrodes may or may not be protected from the plasma. In some embodiments, the electrodes are outside of the plasma environment or are otherwise isolated from the plasma to achieve a clean and more stable plasma. This favorably impacts downstream sample analysis.

In various practices of the invention, plasma formation may be immediate to sample ionization or may be physically separated from sample ionization. Sample ionization may or may not occur in the plasma. Separation of plasma formation from sample ionization results in cleaner, more reliable, and more stable sample ionization. This also favorably impacts downstream sample analysis.

In one practice of the invention, the plasma is formed in a gas flow channel and at least one of the plasma electrodes is protected from contact with the plasma. One or more of the plasma electrodes may be located external to the gas flow channel. Alternatively, at least one of the plasma electrodes may have an associated material layer for protecting the surface of the electrode(s) from destructive contact with the plasma. In one embodiment of the invention, the material layer includes a low or non-conductive material (e.g., an insulator or dielectric) for isolating one or more of the plasma electrodes. In one implementation, the invention employs a dielectric of high permitivity material to enlarge spacing between the metal electrodes of the plasma generator, while still achieving tight, effective gap spacing. This embodiment achieves a plasma with well-defined, temp-controlled emission qualities.

In various implementations, electrode surface protection reduces and/or prevents erosion of electrode surfaces, and/or limits and/or prevents ion contamination of the plasma. Thus, according to one advantage, a plasma generator of the invention is able to ionize a wide range of compounds for practical analytical applications, without contaminating the ionized sample.

In various practices of the invention, plasma formation results in ionized atoms and molecules, generation of free electrons, and the like. This process may be favorably controlled by changing the plasma electric field drive parameters. Regulation of drive waveform characteristics may include selectively adjusting the plasma drive signal frequency and/or magnitude and/or duty cycle, and/or by making changes in pressure, humidity, gas content, volume, and the like. According to another advantage, the invention enables achieving controlled and selective ionization and/or intended fragmentation of a sample, with control of formation of by-products (e.g., NOx), and/or control of undesired formation of clusters, fragmentation, and the like.

According to various practices, the invention enables operation at a wide range of ionization levels, as needed, from low to moderate to high energy, and from "soft" to "hard" ionization, as desired.

Soft ionization involves charge attraction and transfer reactions and produces molecular ions, and is non-destructive. Hard ionization results from electron impact and produces fragment ions. Both types of ionization may be achieved in practice of the invention. According to one feature, soft ionization may be selected for analysis of intact ionized molecules and hard ionization may be selected for sample fragmentation for generating additional useful data, such as, without limitation, for analyzing when complex mixtures. According to another feature, the invention controls plasma intensity and ionization levels as needed.

According to a further embodiment of the invention, one or more dopants may be introduced into the plasma process to change characteristics (e.g., frequency) of the emitted light, such as where a target photon output is sought, or to suppress interferences. Furthermore, introduction and control of dopants (e.g., acetone, water vapor, or other suitable dopant.) can reduce ignition energy or keep alive energy, as such function is expressed in known Paschen curves, for a given plasma, as well as impacting species creation, density and energy. Control of plasma energy impacts rate, energy and efficiency of ionization in the plasma field.

Thus, according to one aspect, the invention enables control of a plurality of levels of ionization. Plasma ionization control improves sample ionization control. Such controls, in turn, improve the ability to direct and control sample analysis.

According to a further embodiment, the invention provides substantially concurrent, or in some embodiments, substantially simultaneous generation of both positive and negative ions in the plasma. Such generation in the plasma enables a correspondingly similar generation of positive and negative sample ion species. In a one embodiment of the invention, positive and negative sample ion species are generated and then filtered, detected and identified substantially concurrently or even simultaneously in a DMS system of the invention. One result is fast, reliable and efficient chemical analysis of ionized sample species.

In one practice, the invention includes a flow path for flow of a gas and a sample. Embodiments of the flow path enable local plasma formation and local sample ionization and, optionally, enable local sample analysis. The flow path may accommodate, for example, multiple flows, split flows and/or counter flows, and may include an analytical system with a plurality of flow channels for processing an ionized sample.

Ionizing the gas generates ionization media and by-products. In a particular practice of the invention, a flow arrangement enables (1) flow of the by-products in the plasma field in a direction away from the sample ionizer, and (2) flow of the ionization media out of the region of the plasma field and into the sample ionizer. Therefore, the sample is advantageously ionized in the sample ionizer by the ionization media outside of the plasma and away from the by-products. One result is cleaner and more reliable sample ionization.

In another practice, the plasma generator generates photons. In one configuration, the sample is ionized with the photons outside of the plasma generator in a "windowless" photo-ionization arrangement. In one embodiment, the invention includes a windowless atmospheric pressure photo-ionization (APPI) system in which capacitive gas discharge plasma ionization is used as a source of photons, and the photons are used downstream to ionize the sample outside of the plasma region.

The photo-ionized sample is then transported downstream for other use. Such arrangement improves ion species generation and analysis by avoiding the affect of the complex chemistry of plasma ionization upon sample processing. The windowless photon source is an improvement over a typical UV photo-ionization source and avoids inconsistencies and absorption limitations that often stem from transmission through a UV window. This process reduces sample contamination and calibration needs.

Various electrode configurations are within the spirit and scope of the invention, including planar, cylindrical, curved, molded, wire, and/or needle shapes, which present any variety of flat, pointed, or curved surfaces and may be integrated into planar, curved, cylindrical and/or other suitably configured filters, separators and/or spectrometers, and may be parallel or at an angle to each other. The gas sample may flow, for example, over, between and/or around the electrodes.

The flow path may have one or more inlets, accommodating one or more flows, which may include gas, a sample, dopant(s) and/or other flows. In one embodiment, multiple gas flows are arranged to permit selective introduction of a selected gas, such as a dopant, to control, optimize or stabilize plasma parameters. In another embodiment, a multiple flow channel system is provided for localization of plasma formation, sample ionization, and sample analysis. In a further multi-channel device of the invention, multiple processes are performed for characterizing ion species. This arrangement may include a parallel or serial array of processes.

Preferably the system includes a controller and the system is operated for optimization of plasma generation and sample processing.

In one practice, the flow path receives a dopant, the dopant flowing in the plasma generator to affect the plasma generation. In another practice, the dopant flows in the sample ionizer to affect sample ionization. In another practice, the dopant flows in the sample analyzer to affect analyzing of the ionized sample.

In another practice, a first flow channel part includes a flow inlet and outlet and sample flow into the flow channel part and both positive and negative sample ions are generated. The sample ions are transported along the first flow channel part toward the outlet and are influenced by an ion deflector, wherein selected ions of the positive and negative sample ions are deflected from the first flow channel part into the second flow channel part by the ion deflector. The selected and deflected sample ions are processed in the second flow channel part by the sample analyzer. The sample analyzer characterizes the sample based on the processing in the second flow channel part of the selected and deflected sample ions.

Efficient plasma generation may be implemented in circuit design. In one practice of the invention, a resonant drive is used for generating the plasma, which produces a high frequency RF field at low power. In a further practice, a feedback loop including a photo-detector is implemented as part of a plasma drive stabilization circuit, resulting in a stabilized plasma ionization source. In various embodiments of the invention such feedback may be implemented using a simple detector to gauge photon intensity or a photo-spectrometer that evaluates photo emission spectra to more completely evaluate the plasma formation and sample ionization process.

In one practice of the invention, a resonant plasma drive circuit generates plasma formation. In a one embodiment, the plasma electrodes are driven with a modulated drive signal. This modulation stimulates the electrodes to produce ions in "packets" having a frequency related to the modulated drive signal, and having an average intensity controlled by the modulated drive signal. A system using this modulated drive signal technique uses low power, provides precise and linear control of plasma intensity. Plasma intensity sufficient to produce ion levels compatible with a compatible sensor can be achieved.

Modulation of the plasma generator drive signal reduces plasma drive power consumption. Use of such plasma modulation also improves spectrometer performance in a preferred DMS embodiment of the invention. According to one feature, the plasma drive modulation encodes the ionized sample signal to be detected. According to another feature, this characteristic of the modulation can be used to discriminate against noise contribution, which is spread over a different and wider band of frequencies.

Embodiments of the invention may also include improvements in DMS drive techniques. Driving a DMS RF filter with a modulated RF drive signal improves DMS operating efficiency. In one embodiment, a circuit drives the DMS filter electrodes to generate an asymmetric high RF field with a duty cycle and DC offset compensation voltage to filter the ions in the ion flow by DMS techniques. A system using a modulated filter drive signal technique may include a circuit operating with a low voltage DC source (e.g., 20 volts) compared to traditional circuits that operate with sources providing 200 Volts or more. As a result of the lower source voltage, a low cost, small geometry MOSFET transistor can be used in this circuit, and low cost components overall can be used.

According to some embodiments, the invention includes both plasma ionization methods and DMS filtering methods. According to other embodiments, the invention includes both modulated plasma formation and modulated DMS filtering methods.

Additional features, benefits and advantages of the invention are further described with respect to the following illustrative embodiments.

BRIEF DESCRIPTION OF THE DRAWINGS

The foregoing and other objects, features and advantages of the invention will now be described with respect to the the accompanying drawings in which like reference designations refer to like parts throughout the different drawings. The drawings are not necessarily to scale, emphasis instead being placed upon illustrating the principles of the invention.

FIG. 1A is a generalized block diagram of a system employing a capacitive gas discharge plasma ionizer according to an illustrative embodiment of the invention.

FIG. 1B is a more detailed block diagram of a system employing a capacitive discharge plasma ionizer according to an illustrative embodiment of the invention.

FIG. 1C is an illustrative resonant RF drive circuit of the type that may be employed in the system of FIG. 1B.

FIGS. 4A and 4B are graphs showing a comparison of the mass positive spectra (FIG. 4A) from a radioactive source and (FIG. 4B) from an illustrative embodiment of the invention, as detected by a mass spectrometer with a low plenum gas flow.

FIGS. 13A–13J show diagrams of alternative electrode configurations for a capacitive discharge plasma ionizer according to various illustrative embodiments of the invention.

FIGS. 14A–14C show additional illustrative electrode configurations for a capacitive discharge plasma ionizer of the invention.

FIGS. 15A–15F show further illustrative electrode configurations for a capacitive discharge plasma ionizer of the invention.

FIG. 17 shows a diagram of intermeshed electrodes for a plasma generator formed on a single substrate according to an illustrative embodiment of the invention.

FIG. 18 shows a diagram of intermeshed electrodes for a plasma generator formed on a single substrate and rotated 90 degrees on the surface of the substrate according to another illustrative embodiment of the invention.

FIGS. 20A–20I are diagrams of illustrative flow structures exemplary of the type that may be employed with capacitive discharge plasma ionizers according to various illustration embodiment of the invention.

FIG. 24 is a graph of optical intensity output versus voltage for a conventional plasma generation source.

FIG. 25 is a graph of optical intensity versus duty cycle for a plasma generation source using a drive circuit according to the principles of an illustrative embodiment invention.

FIG. 37 is a top view of a circuit board trace used to implement a primary or secondary winding in the transformers of FIG. 31 according to an alternative illustrative embodiment of the invention.

DESCRIPTION OF ILLUSTRATIVE EMBODIMENTS

Figure 2B:
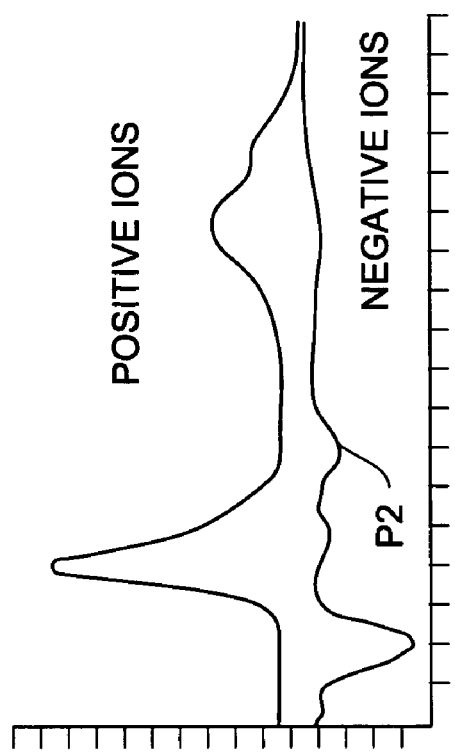
FIG. 2B is a graph depicting positive and negative DMS spectra generated by a capacitive according to an illustrative embodiment of the invention and having both electrodes insulated.

The invention, in one aspect, relates to plasma-assisted sample ionization. According to one embodiment, the invention features capacitive discharge plasma ionization of a chemical sample and an analyzer for analyzing the ionized sample. Turning to the illustrative embodiments of FIG. 1A-1C, the system 10 includes a capacitive discharge plasma ionization source 11 and an analytical system 20, wherein the sample S and the carrier gas CG flow into a plasma field F in the plasma source 11. The ions M+ and M− from the ionization process flow along the flow path 12 out of the plasma source 11 and into the analyzer 20 for analysis.

In the illustrative embodiment, the analyzer 20 provides an analytical electric field for analyzing ions associated with the ionized sample. The analyzer 20 may be, for example, a mass spectrometer, an IMS spectrometer or other suitable detector. According to one illustrative embodiment, the analyzer 20 is DMS spectrometer and the analysis is based on aspects of the mobility of the ions in an analytical field. Detection of ion species of interest is indicated as m+/− output from the analyzer 20.

In FIG. 1B, the plasma source 11, also referred to as a plasma generator or plasma ionizer, is separate from, but in communication with, the analyzer 20. Alternatively, the plasma source 11 may be integrated into the analyzer 20 to form an integrated system 10.

The capacitive discharge plasma ionization source 11 includes a pair of electrodes 14 and 16, which are preferably insulated from gas reactions in the plasma ionization region 36. In response to a sufficient drive voltage being supplied across the electrodes 14 and 16, a discharge field F is established. According to the illustrative embodiment, the plasma drive voltage ranges from about 1 to about 100 kHz and is modulated in some aspect (such as in intensity, duty cycle, frequency, or the like).

In embodiment of FIG. 1B, a carrier gas CG (also referred to as a transport gas) and sample S are fed through an inlet 13 into a plasma ionization region 36. The transport gas is ionized by capacitive discharge between the electrodes 14 and 16. This discharge process produces a plasma 40, which ionizes the gas CG and the sample S with both positive and negative ions, $M^+$, $MH^+$, and $M^-$, and illustratively generates $(H2O)_n$, $H^+$, $O^-$, $O_2^-$, $O_3^-$, $(N_xO_n)^+$ and/or $(N_xO_y)^-$ $(H_2O)_n$.

The generated ions in the ionization region 36 exit through a passage 37 for further downstream utilization. In an analytical embodiment of the invention, these ions proceed from the passage 37 into the spectrometer 20 for analysis, as shown in FIG. 1B.

FIG. 1B shows an illustrative control and drive circuit 22. The control and drive circuit 22 is depicted in more detail in FIG. 1C. As shown, the illustrative circuit 22 includes a pulse generator 22a, a resonance generator 22b, and a resonant circuit 22c. The resonant circuit 22c includes the electrodes 14 and 16 (spaced by an ionization gap G) and an inductor L. A microchip or other logic or controller device 22d may also be supplied in communication with drive circuit 22, and optionally may include inputs from other system feedback or data sources, to affect total system control. The control and drive circuit 22 may be driven using known techniques. The control and drive circuit 22 may also employ an optimization routine for selecting operating conditions based on the above mentioned system inputs.

Figure 2A:
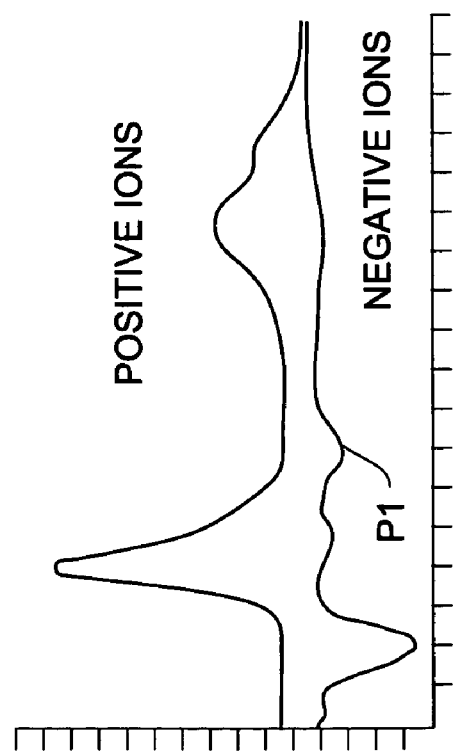
FIG. 2A is a graph depicting positive and negative spectra generated with a radioactive source.

Plasma sources of the invention offer a viable alternative to radioactive ionization sources. FIG. 2A shows positive and negative DMS spectra generated with a radioactive ionization source ($^{63}$Ni at 10 mCu) and FIG. B shows positive and negative DMS spectra generated by a capacitive discharge plasma ionization source, such as the source 11, with both electrodes 14 and 16 being electrically isolated from each other (insulated) and/or physically isolated from the plasma (for example, by applying a low or non-conductive coating, such as a dielectric or an insulating material, to the electrodes), according to an illustrative embodiment of the invention. This comparison demonstrates that the non-radioactive ionization source 11 of the invention can replace a radioactive source and provide similar performance.

Figure 3B:
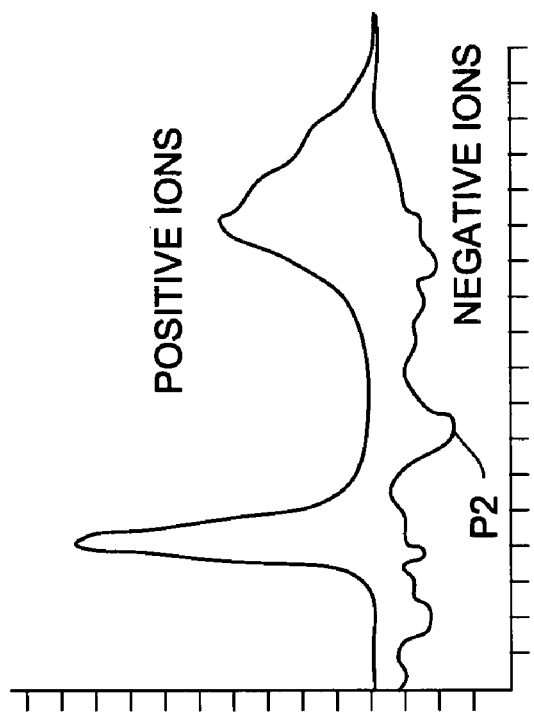
FIG. 3B is a graph depicting positive and negative DMS spectra generated by a capacitive discharge plasma ionization source according to an illustrative embodiment of the invention and having one electrode insulated.
Figure 3A:
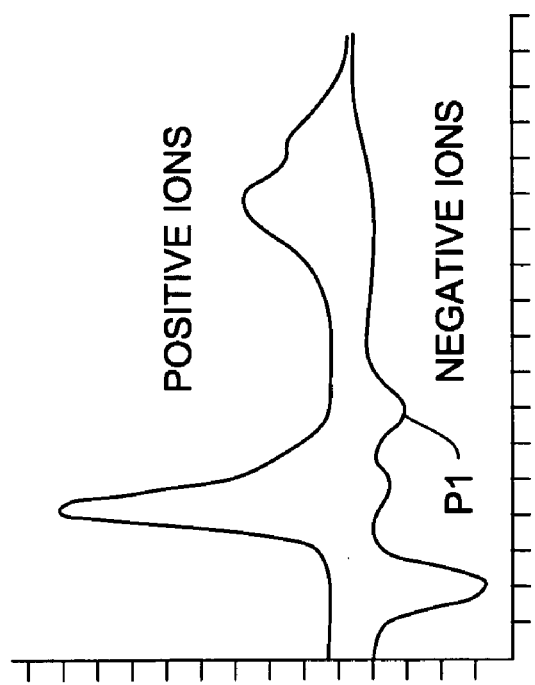
FIG. 3A is a graph depicting positive and negative spectra generated with a radioactive source having one electrode insulated.

FIG. 3A shows positive and negative DMS spectra generated with the radioactive ionization source of FIG. 2A, but with only one of electrodes 14 and 16 being electrically and/or physically isolated, for example, by application of a coating as described in relation to FIG. 2A. FIG. 3B shows positive and negative DMS spectra generated plasma generator 11, also with only one of electrodes 14 and 16 being isolated (electrically and/or physical, as described above). As can be seen, the positive spectra from the radioactive and the plasma sources are nearly identical. However, the negative spectra in FIG. 3B, with one electrode protected (for example, by being isolated as a result of an application of a low- or non-conductive coating)—the protection being from, for example, accelerated ions and/or electrons—is somewhat degraded versus that of FIG. 3A, where both electrodes are protected.

In implementations of various illustrative embodiments, we have found that the plasma source of the invention is capable of providing adequate ionization energy in many applications, operating on as low as about a few watts or lower (e.g., about 0.5 watts in one embodiment). We also observed that in the comparisons described with respect to FIGS. 2A–2B and FIGS. 3A–3B, the beta source was capable of generating a maximum ion current of about 4 pA, while the above described illustrative embodiment of the invention delivered a maximum of about 12 pA. Thus, one important advantage of the invention is that it provides an efficient and powerful plasma ionization source.

FIGS. 4A and 4B show graphs depicting a comparison between the positive spectra from a $^{63}$Ni radioactive source (FIG. 4A) and from a plasma source (FIG. 4B) of the invention. The spectra of FIGS. 4A and 4B were, detected by a mass spectrometer with a low plenum gas flow (i.e., a barrier counter-flow of clean gas to prevent introduction of laboratory air into the MS). The system of FIG. 4A was capable of generating about 4,000 ions per second, while the system of the invention (FIG. 4B) recreated the same or comparable spectra, while achieving an ion production rate of about 50,000 ions per second. Thus, another important advantage of the invention is that it can provide a rich source of ions for a broad range of applications. It is further noted that while FIGS. 4A–4B show MS results with a low plenum gas flow, the invention is not limited to particular flow rates, whether in the plasma ionizer (sample and carrier gas) or in a DMS analyzer (ion flow) or at the front end of an MS (plenum).

Figure 5A:
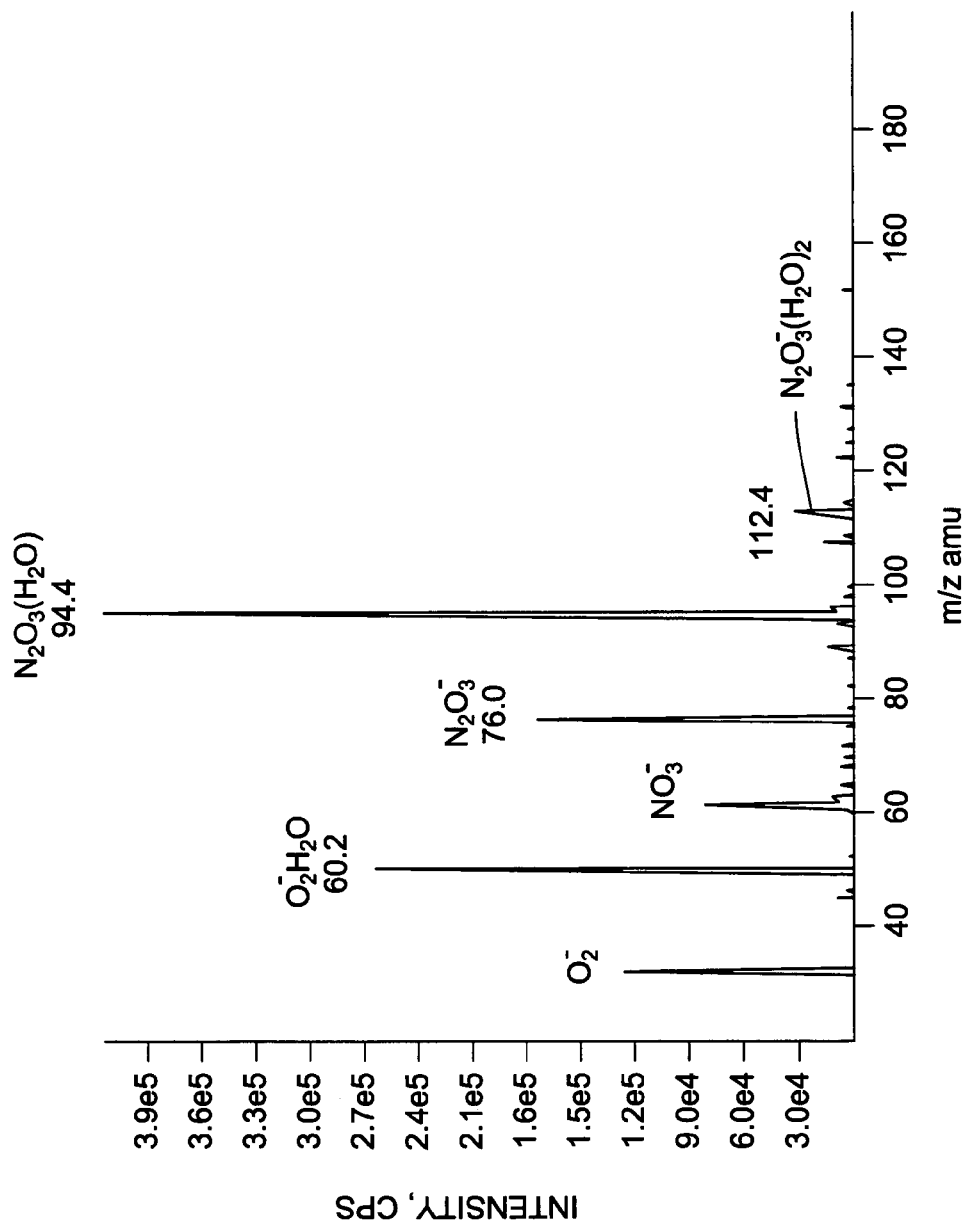
FIGS. 5A and 5B are graphs showing negative mode mass spectrometer spectra for (FIG. 5A) air, and (FIG. 5B) air plus 20 ppm of $SF_6$(M=146), after plasma ionization according to an illustrative embodiment of the invention.
Figure 5B:
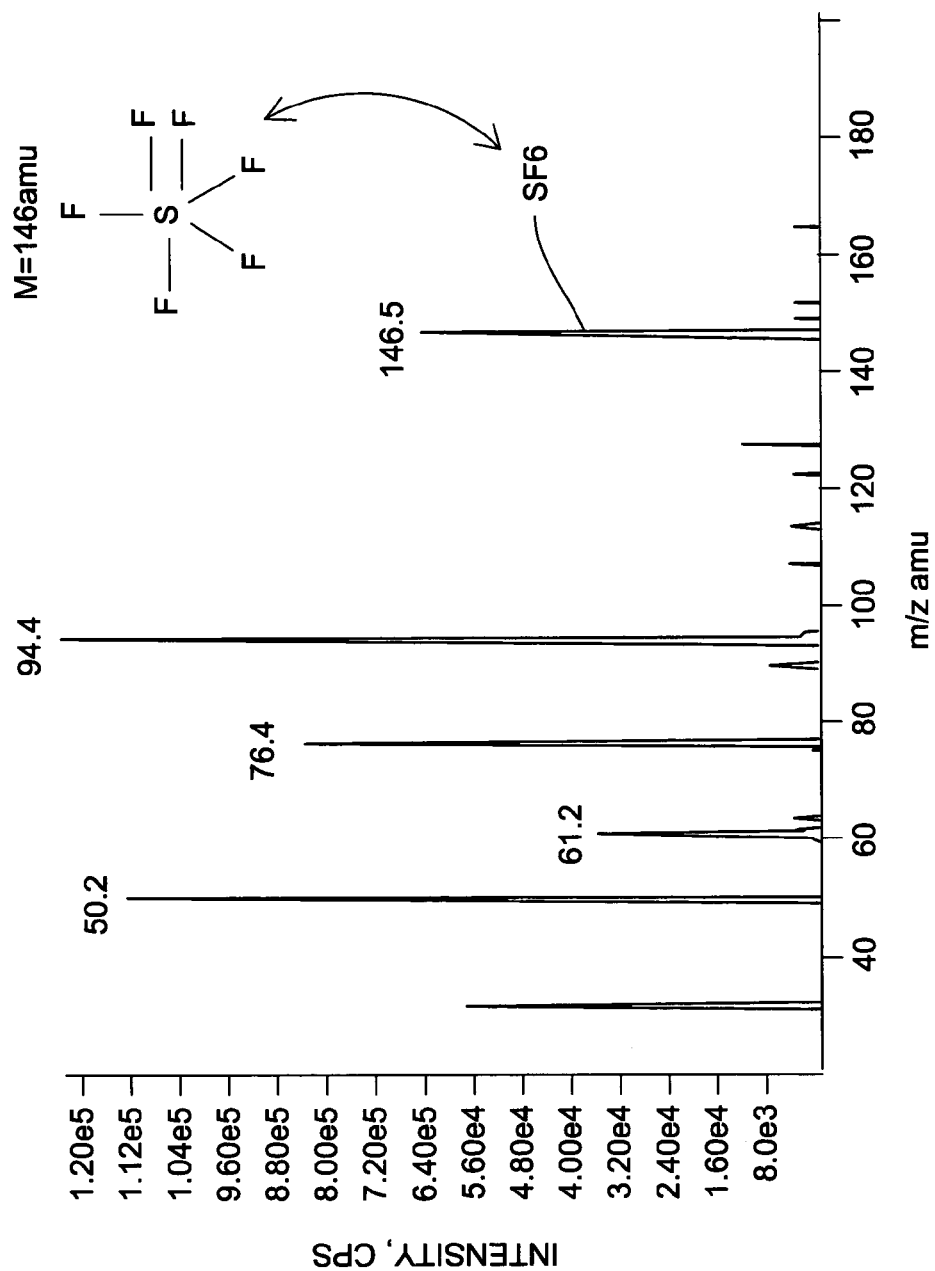

FIGS. 5A–5B show negative mode mass spectrometer spectra for air and air plus 20 ppm of $SF_6$, respectively, after plasma ionization, according to an illustrative embodiment of the invention. Comparing the two frames, the $SF_6$ (M=146 amu) peak stands out and is clearly identified, while the background spectra retains its integrity.

Figure 6:
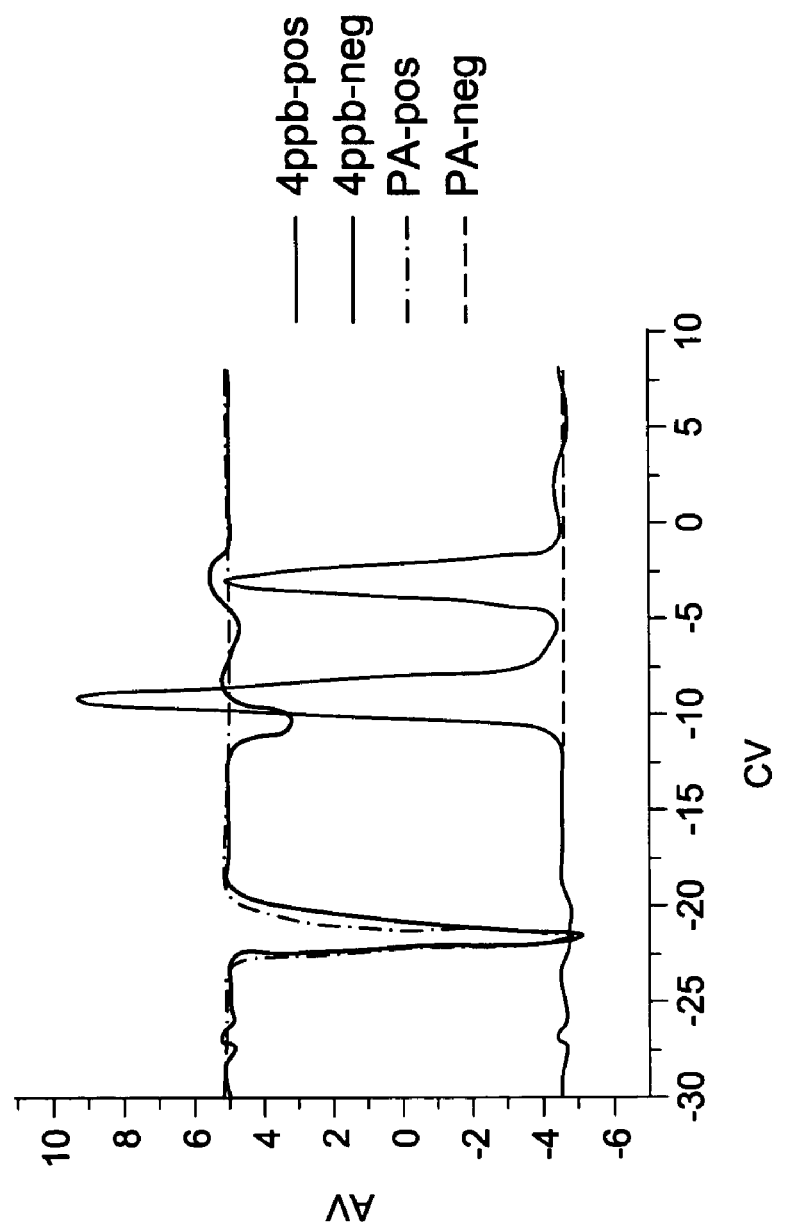
FIG. 6 is a graph showing DMS detection of mercaptan in purified air ionized in a capacitive gas discharge plasma ionizer according to an illustrative embodiment of the invention.
Figure 7:
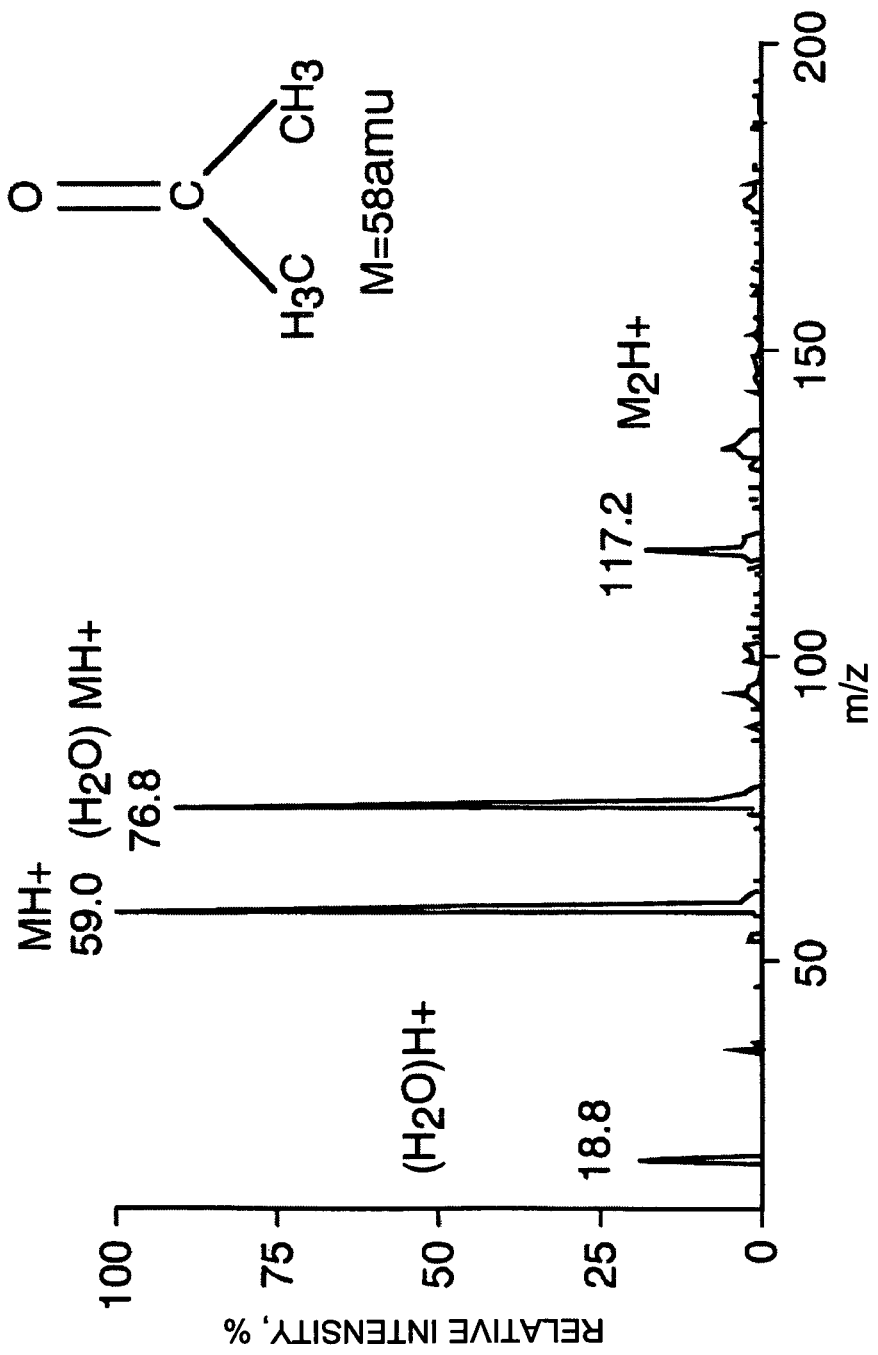
FIG. 7 is a graph showing mass spectra for acetone generated and reproduced by ionization of acetone according to an illustrative embodiment of the invention.

Exceptional detection results may also be obtained using other detection devices. For example, in FIG. 6, a DMS spectrometer received an ionized output of a mercaptan sample and purified air as outputted by an a capacitive gas discharge plasma generator of the invention. As can be seen from the graph of FIG. 6, the negative and positive mercaptan (+/−mer.) peaks and background spectra are clearly defined. FIG. 7 shows a graph depicting another illustrative application of the invention in which the mass spectra for acetone was generated and reproduced by soft ionization of the acetone.

Figure 8:
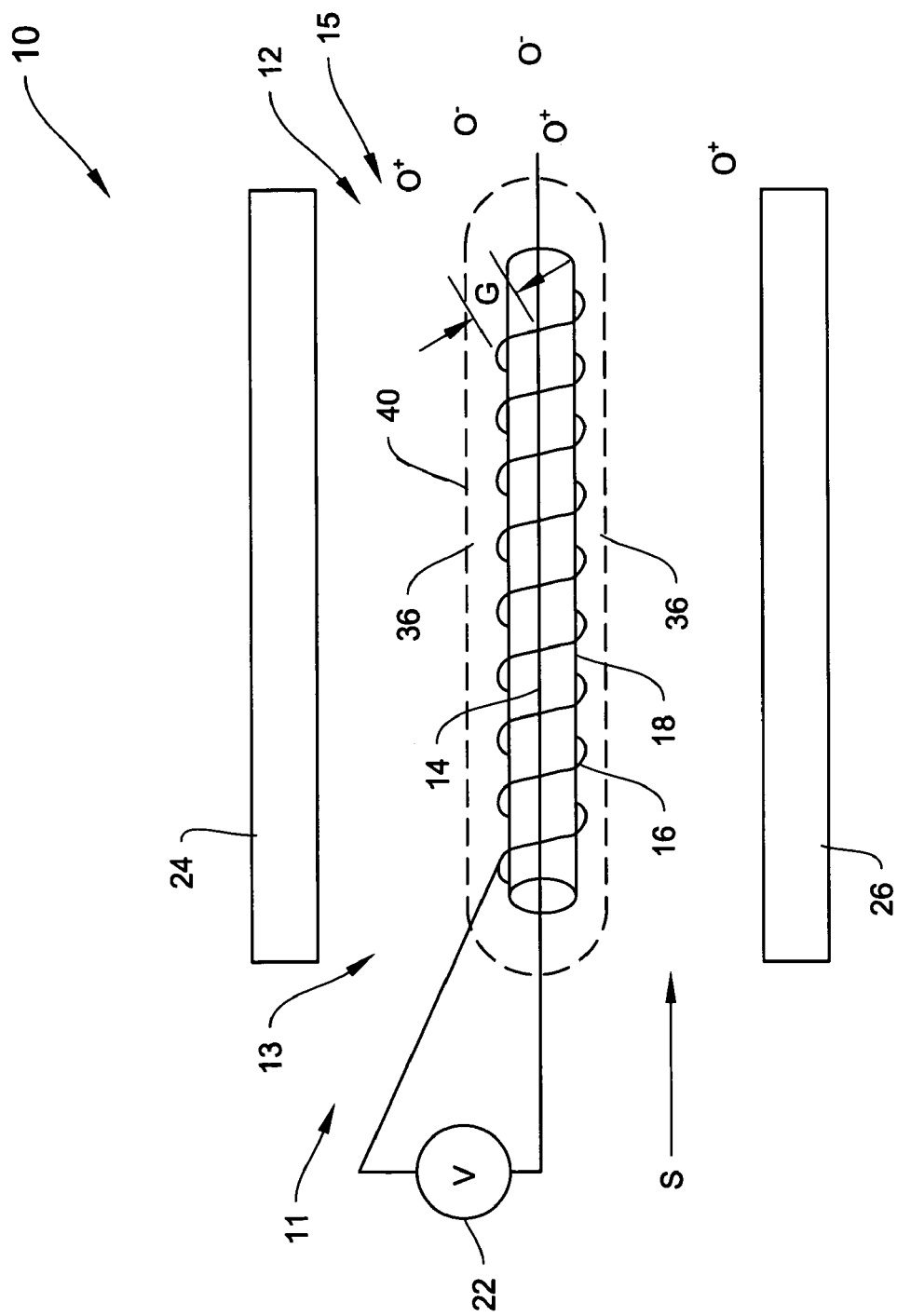
FIG. 8 is a diagram of a capacitive discharge plasma ionizer structure according to an illustrative embodiment of the invention.

FIG. 8 depicts a system 10 including a capacitive discharge plasma ionization source 11 positioned within a flow channel 12 according to an illustrative embodiment of the invention. The ionization source 11 defines an ionization region 36 about the ionization source 11. The flow channel 12 has a planar geometry formed by upper and lower substrates 24 and 26. Alternatively, the ionization source 11 may be placed within a cylindrical, polygonal (e.g., rectangular), or otherwise suitably shaped flow channel. According to various illustrative embodiments, the flow channel may include flat or curve surfaces, and the surfaces may be relatively smooth or textured.

The ionization source 11 of FIG. 8 includes a first electrode 14 placed within an isolating capillary tube 18 and a second electrode 16 wrapped around the capillary tube 18. The electrodes 14 and 16 are separated by a gap G. One end of each of electrodes 14 and 16 is connected to the RF drive voltage supply 22 such that the electrodes 14 and 16 function as the plates of a capacitor, with the drive RF voltage applied across them.

Figure 9:
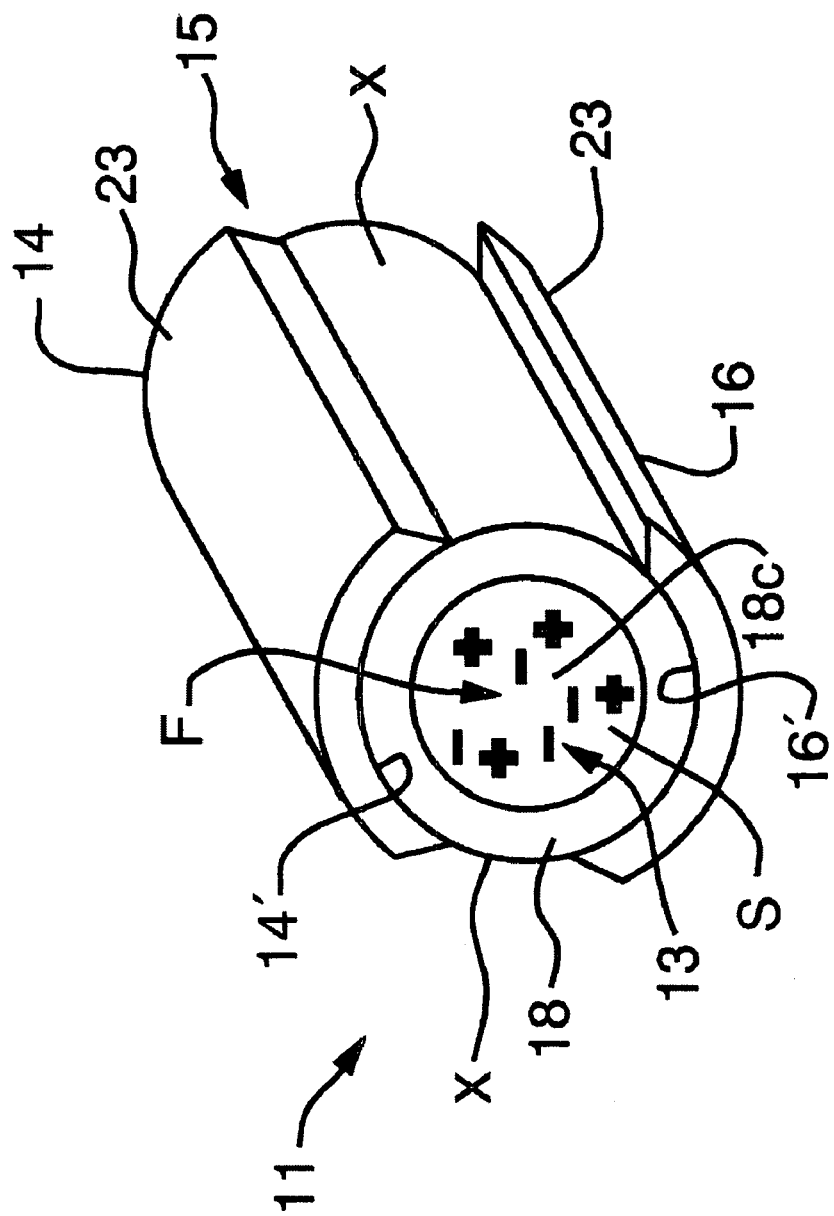
FIGS. 9–12 are diagrams of capacitive discharge plasma ionizer structures according to alternative illustrative embodiments of the invention.

FIG. 9 shows another illustrative embodiment of the invention, in which a plasma ionization source 11 includes an isolation substrate 18. As shown in FIG. 9, the isolation substrate may include, for example, a glass capillary tube. The isolation substrate 14 may be coated with a metallization layer 23. The metallization layer 23 is parted at "x" to define two metallization regions forming the electrodes 14 and 16. In one illustrative configuration, the inner faces 14' and 16' of the electrodes 14 and 16, respectively, are formed on the isolation substrate surface of the tube 18 and face each other through the capillary tube 18 across the open lumen 18c. An RF signal from a voltage source, such as the voltage source 22, may be applied to the electrodes 14 and 14 of FIG. 8 to generate a field F within the lumen 18c of the capillary tube 18.

In the illustrative embodiment of FIG. 9, the gap separating the electrodes 14 and 16 is defined by the outside diameter of the capillary tube 18. Within the tube 18, the entire lumen 18c may be utilized as an ionization region. In one operation, the gas CG and sample S are flowed into the lumen 18c of the capillary tube 18 through the inlet 13. The gas CG is ionized and forms a plasma field F, which in turn ionizes the sample S between the electrodes 14 and 16. This process generates both positive and negative ions, and ionizes the sample into both positive and negative ions +/−, which can be isolated. The ions subsequently exit through outlet 15 for further use, such as in an ion mobility spectrometer, and in one preferred embodiment, in a DMS that processes both positive and negative species simultaneously.

Figure 10:
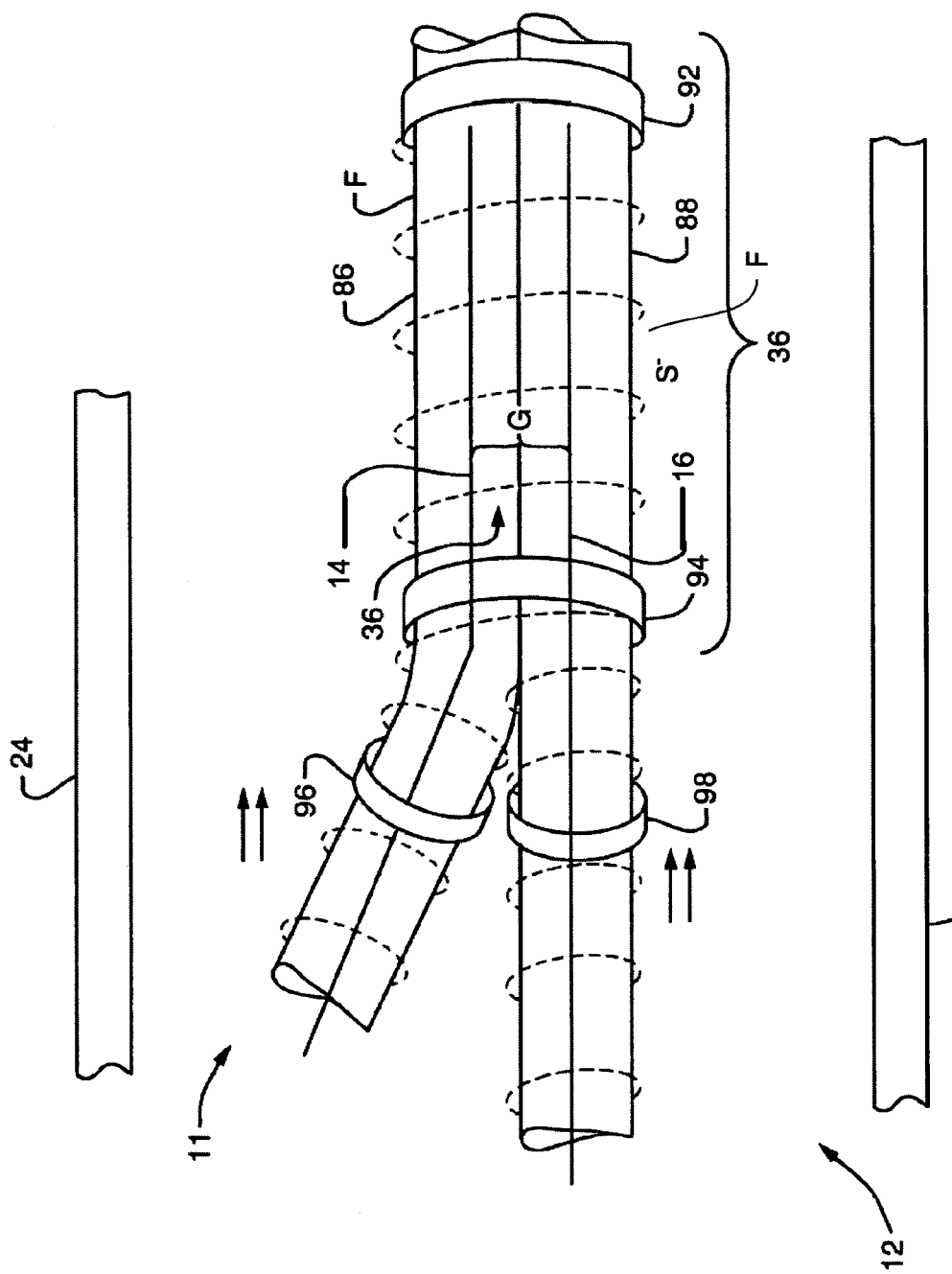
Figure 11:
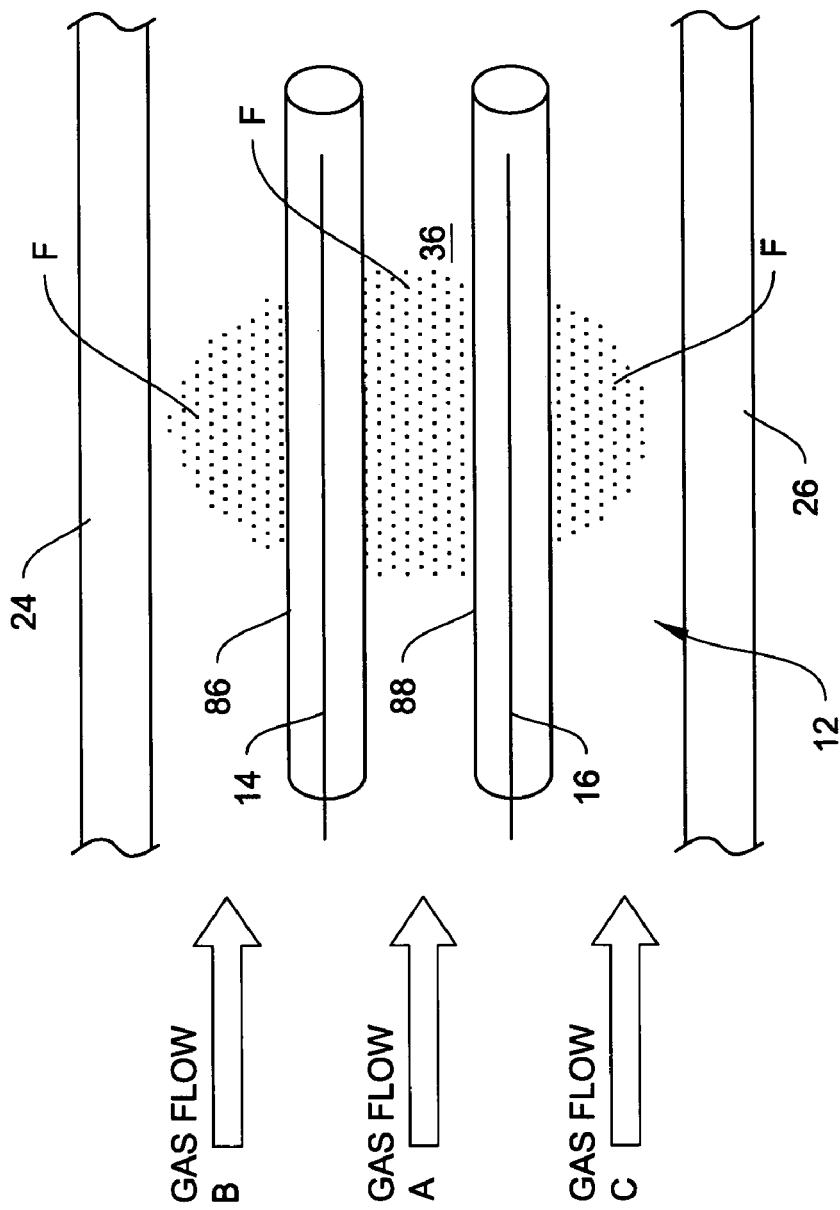

FIGS. 10 and 11 show alternative illustrative embodiments of the invention in which the conducting electrodes 14 and 16 are placed into adjacent tube-like dielectric sheaths 86 and 88, formed from, for example, glass, quartz, ceramic or other suitable material. Preferably, the dielectric sheaths 86 and 88 are fixtured so that the separation between the electrodes 14 and 16 is fixed within the ionization region 36. This separation can range, for example, from having the dielectric sheaths 86 and 88 touching to having a separation of about 5 mm or more.

As shown in FIG. 10, the electrodes 14 and 16 may be held and joined via collars 92 and 94. Just beyond the collar 94, the ionization region is effectively terminated after the electrodes 14 and 14 diverge. This arrangement enables defining the length of the ionization region and thus provides predictable performance characteristics. The abutting collars 96 and 98 are affixed on each of the tubes 86 and 88 after the collar 94 to fix this divergence. In various illustrative embodiments, the electrodes 14 and 16 may be formed of conventional thin wire filaments and may be contained in a tube or coated with a dielectric or other insulating material.

Figure 12:
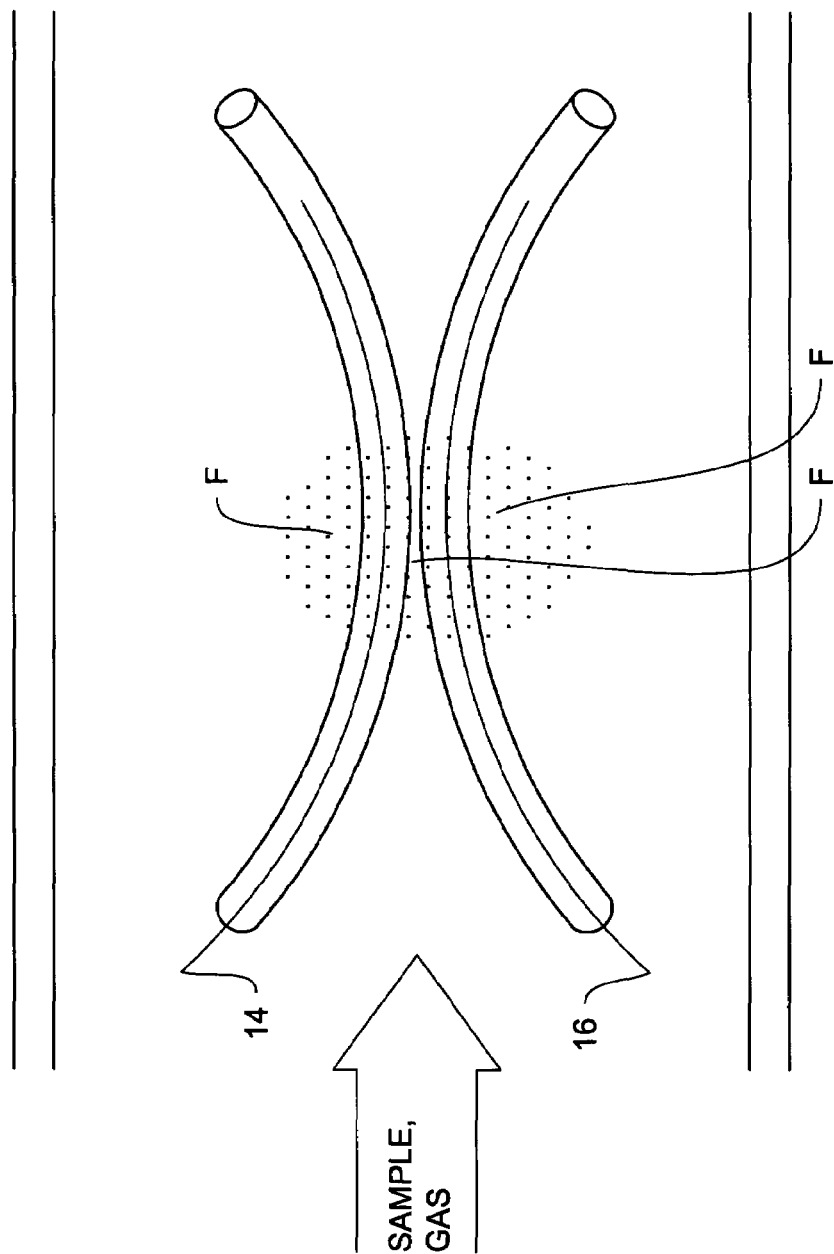

FIG. 12 shows an alternative illustrative embodiment of the invention employing diverging curved plasma electrodes 14 and 16. In this embodiment, the field F is formed between the diverging electrodes 14 and 16. In other illustrative embodiments, the plasma electrodes 14 and 16 may be, for example, parallel or angled relative to each other, be relatively straight or curved, have relatively smooth or textured inner and out surfaces, or any combination of the above.

As described above, the electrodes 14 and 16 are separated by a gap, whether exposed or isolated, embedded in a dielectric material, or within isolating tubes, for example, and whether parallel or diverging. Additionally, the electrode diameter and isolation coating material type and diameter/thickness may be selected such that the fields generated between the electrodes 14 and 16 are accessible to the gas flow. In FIG. 11 the gas flows between the electrodes 14 and 16 and therefore, through the plasma-generating field between the electrodes 14 and 16. However, in FIG. 10, the gas flows along the perimeter of the tubes. Preferably, the field generated between the electrodes extends into this perimeter flow. According to the illustrative embodiment, the drive signal 22, the filaments 14 and 16, and the coating diameter are selected to accommodate generation of the plasma ionization field F in this perimeter area.

FIG. 13A shows a rectangular cross-section plasma flow arrangement wherein the gas is contained and flows between the plasma electrodes 14 and 16 in the field F, according to an illustrative embodiment of the invention. In the embodiment of FIG. 13B, the electrode 14 is on a surface of a first substrate 24, and the electrode 16 is on a surface of a second substrate 26. The electrodes 14 and 16 are driven by the voltage source 22.

An isolation layer 34 of, for example, $Al_2O_3$ (Alumina) or $SiO_2$, or other suitable material, is formed over one or both of the electrodes 14 and 16. In the embodiment of FIG. 13B, the ionization source 11 is arranged with the opposing surfaces of the inner isolators 34 being spaced apart by about 10 μm or more to define the plasma ionization region 36.

As discussed above, FIG. 12 shows curved diverging tube electrodes 14 and 16 for plasma generation. In FIG. 13C, the electrodes 14 and 16 are positioned at an angle to achieve a divergence. The electrodes 14 and 16 are formed respectively on the upper and lower substrates 24 and 26. The angle between the substrates 14 and 16 is selected such that the ionization region 36 has a narrow region 41a and a wide region 41b. A higher field strength is created in the narrow region 41a relative to the wide region 41b as a result of the electrodes 14 and 16 being closer together. This in turn creates a higher field strength and hence a more intense ionization field, which can assist in plasma ignition. In the illustrative embodiment of FIG. 13C, the gas that enters the plasma ionization region 36 is first ionized in the narrow region 41a. The electric field travels from the narrow region 41a to the wide region 41b and the ionization process propagates accordingly to generate the ions (++,--).

Figure 13D:
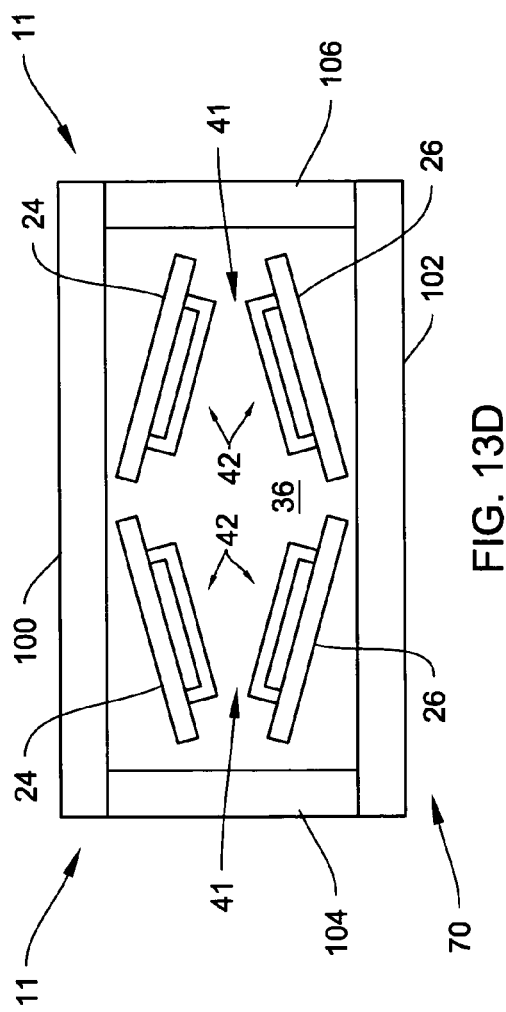

In the embodiment shown in FIG. 13D, a pair of ionization sources 11 having non-parallel electrodes cooperate to form a plasma generator, according to an illustrative embodiment of the invention. The ionization sources 11 are positioned within a flow channel 110 defined by an upper substrate 100, a lower substrate 102, a first spacer plate 104, and a second spacer plate 106. As the sample enters the ionization region 36, the plasma formation and ionization process initiates in the narrow regions 41 nearer each spacer plate and then progresses towards the wider regions 42 nearer the center of the channel 110.

Figure 13E:
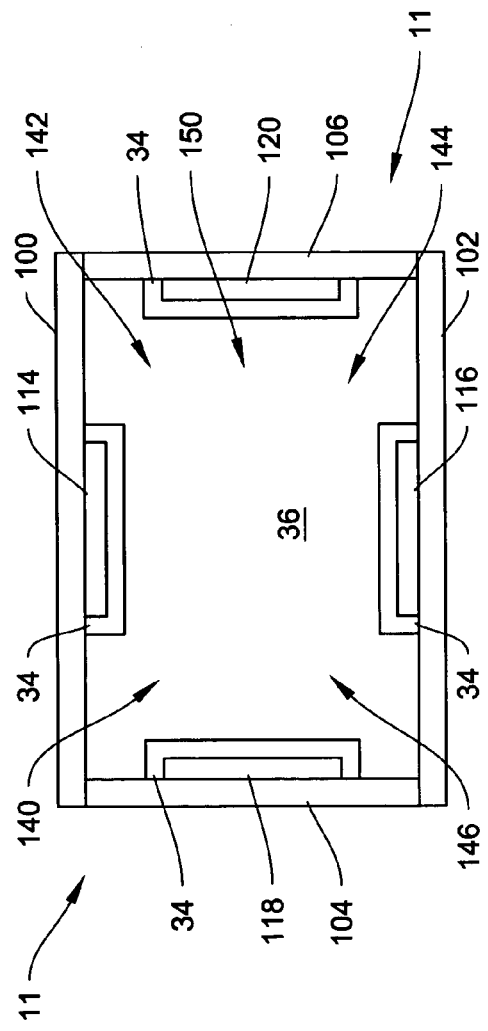

Diverging electrodes are not required to create the above discussed intense ionization regions. FIG. 13E, which depicts an extension of the illustrative embodiment of FIG. 13D can also provide similar intense ionization regions. Referring to FIG. 13E, the ionization source 11 includes a first electrode 114 mounted to an upper substrate 100 and a second electrode 116 mounted to an inner surface of a lower substrate 102. In addition, a third electrode 118 and a fourth electrode 120 are mounted to the inner surfaces of side spacer substrates, 104 and 106, respectively.

The electrodes 114, 116, 118, and 120 couple to a drive control/source and are arranged such that the electrodes 114 and 118 form one capacitor and the electrodes 116 and 120 form another capacitor. Two of the electrodes (e.g., 114 and 118) are of the same polarity, while the two others (e.g., 116 and 120) are of the opposite polarity, such that there are four intense plasma formation and ionization regions 140, 142, 144, and 146 near the corners of the electrodes. When the gas enters the plasma ionization region 36, the ionization process begins at these intense ionization regions and then propagates toward the center 150 of the ionization region 36.

Figure 13F:
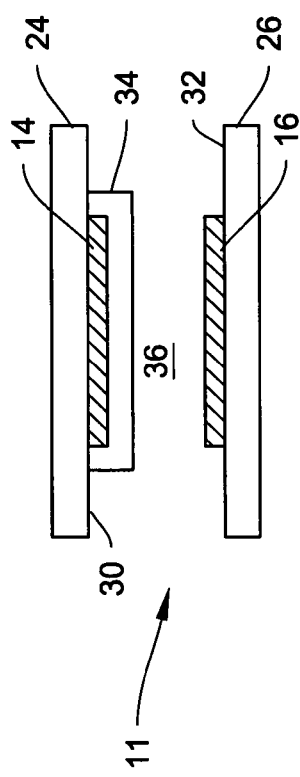

The plasma electrodes can operate without an isolator or at least without an insulator on both electrodes. For example, in an alternative embodiment shown in FIG. 13F, the electrode 16 is not covered by an isolating material. Furthermore, the electrode 14 need not be covered by the isolator. That is, both electrodes 14 and 16 may be exposed directly to the sample gas.

Figure 13G:
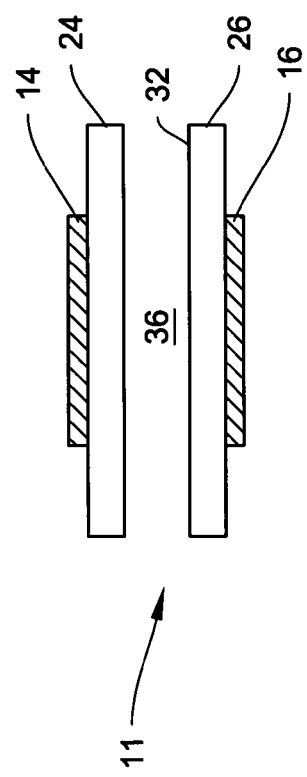
Figure 13H:
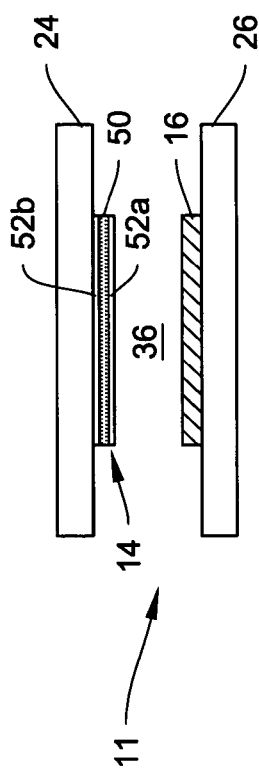

Alternatively, as shown in FIG. 13G, the electrodes 14 and 16 may be mounted to the respective outer surfaces of the substrates 24 and 26, need not be covered by an isolating material. In another alternative embodiment, one electrode is within a favorable environment, e.g., encapsulated in dielectric, while the other electrode is adjacent to the carrier gas flow to be ionized in the generated plasma field. As illustrated in FIG. 13H, the electrode 16 is mounted to the substrate 26, wherein the electrode 14 includes a metal layer 52a on one side of a dielectric substrate 50. The opposite side of the dielectric substrate 50 can also be coated with an additional metal layer 52b. In either case, the electrode 14 is attached to the substrate 24 by suitable attachment mechanism, such as, for example, epoxy glue.

Referring now to FIG. 13I, an alternative embodiment of the ionization device 10 includes an accelerator electrode 60, having its own self potential, mounted to the isolator layer 34 which covers the electrode 14. Alternatively, the electrode 14 and the accelerator electrode 60 may be mounted on opposite sides of the substrate 24, as depicted in FIG. 13J. The accelerator electrode 60 advantageously enables additional control of the ion flow.

As shown in FIG. 14A, the accelerator electrode 60 may include a series of small electrodes 62 interconnected with conductive wires 64. In another illustrative embodiment, as shown in FIG. 14B, the accelerator electrode 60 may include a mesh of interconnected horizontal 66 and vertical 68 wires. Alternatively, as shown in FIG. 14C, the accelerator electrode 60 may include an ensemble of small conductive electrodes 61 that are surrounded by a ring of conductive material 63, such as, for example, a conductive metal.

As discussed above, plasma generators of the invention may be formed with a variety of electrode configurations, which need not be planar plates. As shown in FIGS. 15A–15D, a needle electrode 170 may be used in conjunction with a planar electrode 174 or another needle electrode 170. In FIG. 15A, a needle electrode 170 is coated with an insulator 172 and cooperates with a planar electrode 174 to form a plasma generator of the invention. In FIG. 15B, the planar electrode 174 is coated. In FIG. 15C both are coated, and in FIG. 15D the planar electrode 174 is replaced with a second needle electrode 170, which may have coating 172.

FIG. 15E shows a plasma generator having parallel electrode faces 14" and 16" on a single substrate 24. FIG. 15F shows the diverging embodiment of FIG. 13C configured on a single substrate 24 with diverging electrode faces 14" and 16".

Figure 16A:
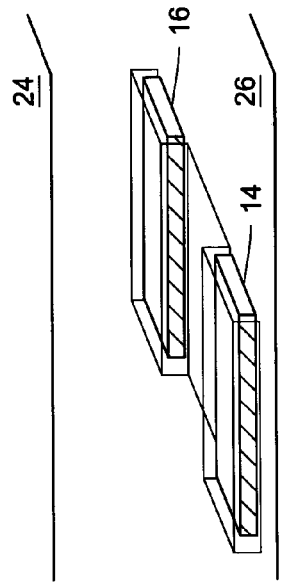
FIGS. 16A–16D show additional illustrative planar, non-planar and contoured electrode configurations for a capacitive discharge plasma ionizer according to the invention.
Figure 16B:
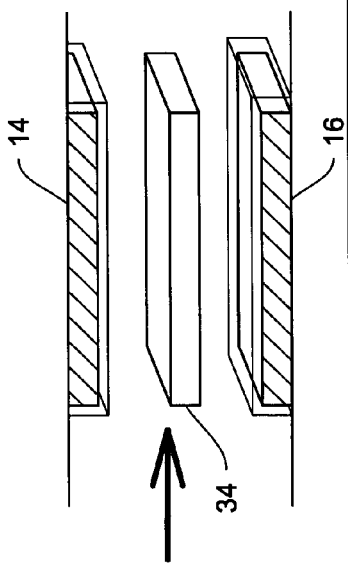
Figure 16C:
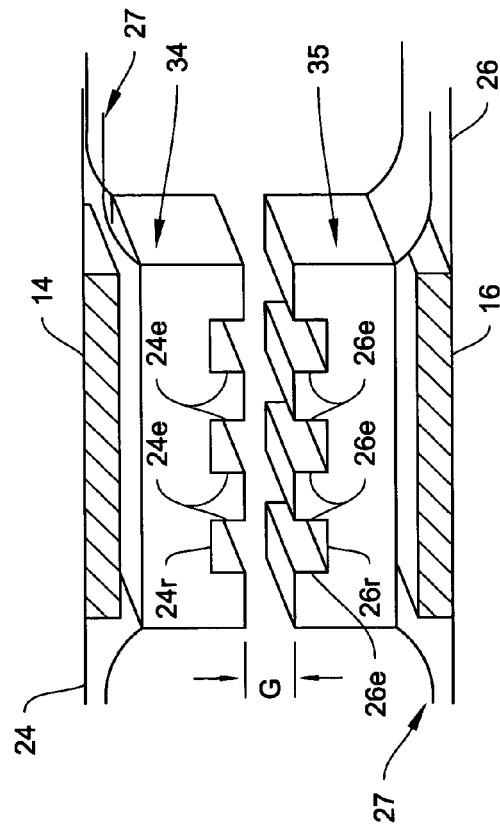

FIGS. 16A–16C show additional planar, non-planar and contoured plasma electrode configurations, respectively, according to various illustrative embodiments of the invention. In some illustrative embodiments, the invention employs a dielectric 34 (such as a floating dielectric as shown in FIG. 16A), which may be, for example, of high permitivity material, such as ceramic, or ink, and enables larger spacing between the metal electrodes, while still achieving a tight, effective gap G spacing. Such a configuration achieves well defined, temp-controlled emission qualities in practice of embodiments of the invention. In this illustration, an adhesive, such as glass frit 27, bonds the dielectric layers 34 and 35, electrodes 14 and 16, and substrate support structure 24 and 26.

Figure 16D:
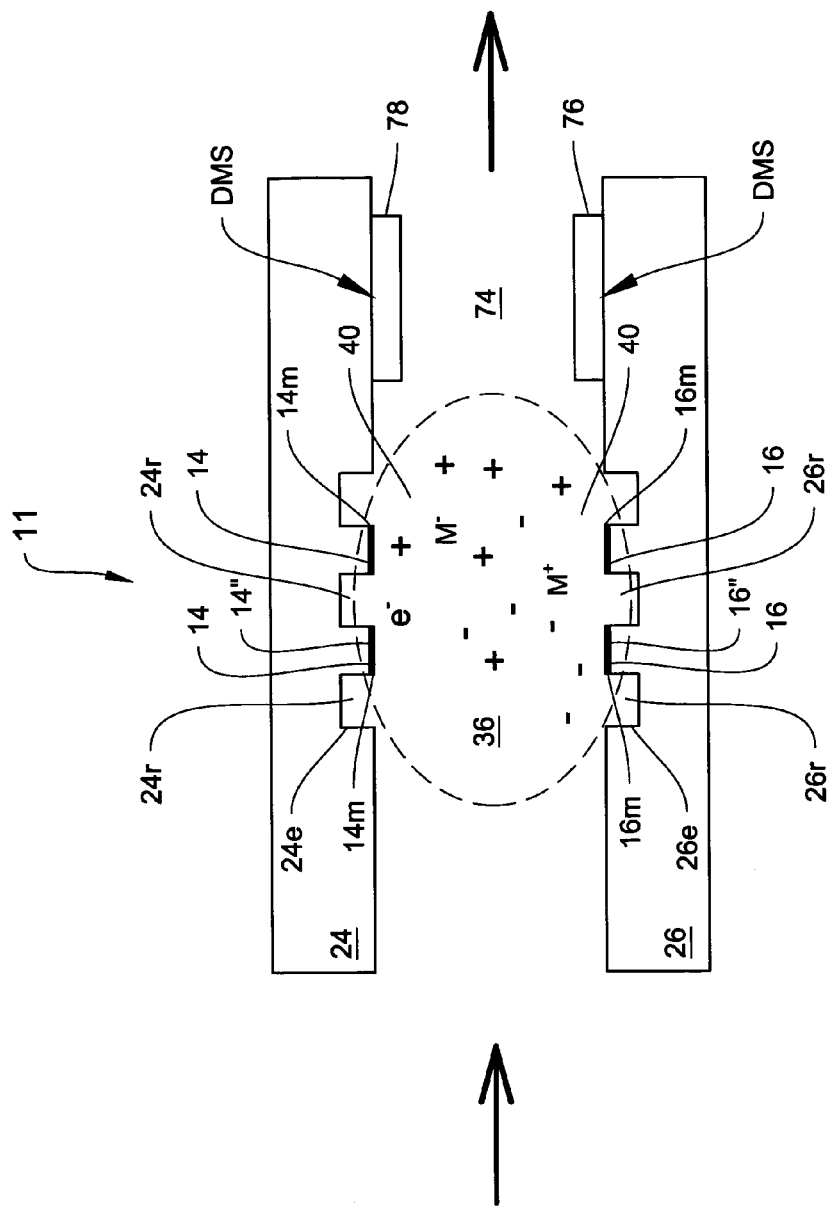

FIG. 16D shows an application of the configuration of FIG. 16C, but with the electrodes formed directly on the ceramic substrates 24 and 26, without the dielectric. In FIG. 16D, the plasma generator 11 is formed between two substrates 24 and 26. The substrates 24 and 26 include a plurality of electrodes, which extend above a local recessed area on each substrate. More specifically, one or more of the electrodes 14 and 16 extend above and beyond an adjacent substrate recess 24r or 26r, provided on each substrate 24 and 26, respectively. The recesses 24r and 26r and the associated edge features 24e and 26e provide a geometric field enhancement and have the effect of focusing the plasma at or above the plasma electrodes 14 and 16 away from the substrate surfaces. The electrodes 14 and 16 may be formed, for example, as metallization layers 14m and 16m on the insulating substrates 24 and 26, respectively, above the associated recesses 24r and 26r and edge features 24e and 26e.

In the illustrative embodiment of FIG. 16D, the plasma 40 is formed in the plasma ionization region 36 somewhat distant from the supporting substrate surfaces. This in effect isolates the corrosive effects of plasma interaction from the neighboring and recessed substrates 24 and 26, with the effect of reducing the complexity of the plasma ionization process. This approach makes it much less likely that matter from desorption, surface erosion and the like, will contaminate the ion flow. As a result, a more efficient, reliable and stable analytical ionization source is realized.

Turning now to FIG. 17, the electrodes 14 and 16 are formed on a single substrate 24" (such as discussed above with respect to the embodiments of FIGS. 15E–15F). The electrodes 14 and 16 each extend to define a number of tines, such as tines 14a, 14b, 14c, 16a, and 16b. These tines enable the electrodes 14 and 16 to be intermeshed while forming the plasma generator 11 on a single substrate. The electrodes 14 and 16 are driven by the RF source 22. FIG. 18 depicts a similar embodiment, but with the tine orientation rotated ninety degrees.

As discussed above, in one preferred embodiment, the electrodes 14 and 16 are isolated from the gas flow. In the embodiments of FIGS. 17 and 18, an isolating layer, for example of a dielectric coating 34, such as, for example, $Al_2O_3$ (Alumina), $SiO_2$, or the like, preferably formed on each exposed electrode (and tine) surface, provides the requisite isolation. The isolation layer is indicated in FIG. 18 by a dotted outline.

Figure 19:
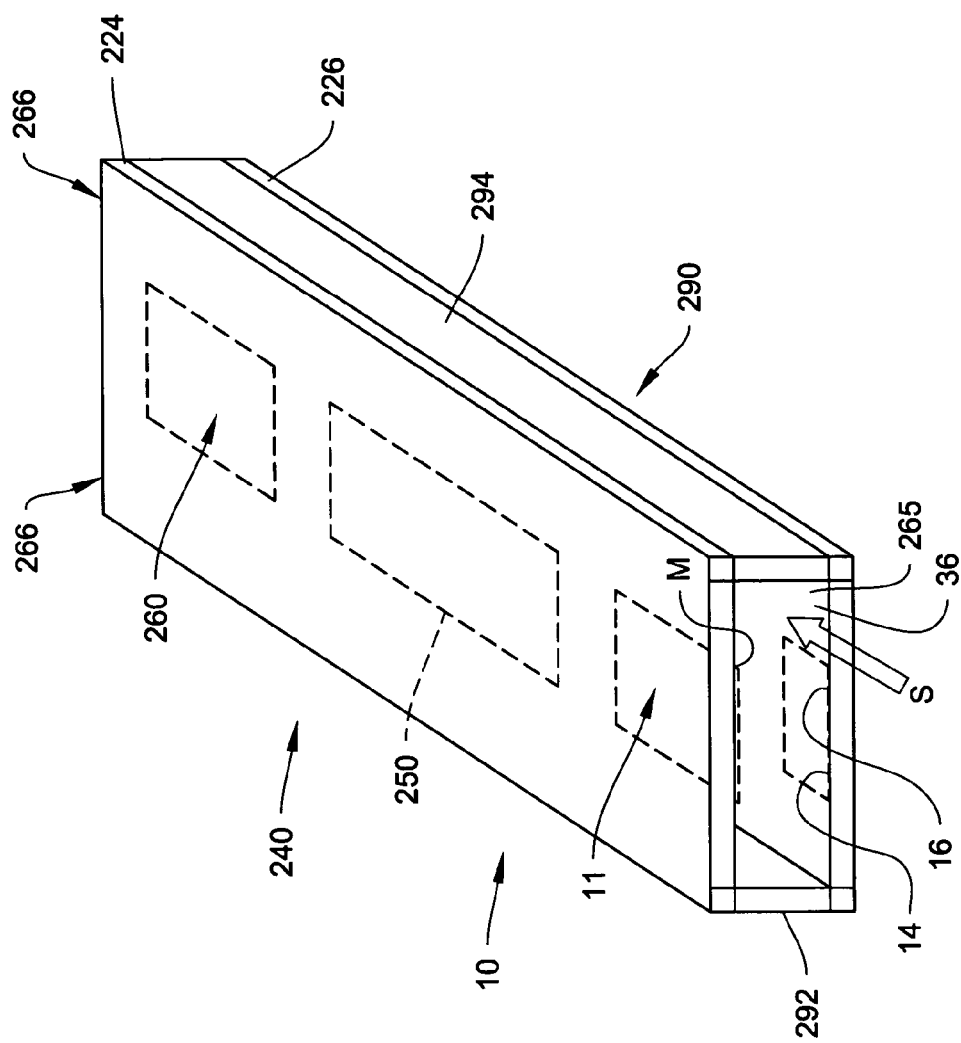
FIG. 19 shows a diagram of a DMS microchip device with opposed substrates and having a plurality of electrodes for plasma ionization and sample analysis according to an illustrative embodiment of the invention.

As shown in FIG. 19, the single substrate may be enclosed in a flow channel defined by a housing M to provide an enclosed plasma generator 11 of the invention, with a sample intake at an inlet 265 and an exhaust at an outlet 266. It should be noted that electrode isolation is not shown in FIG. 17 and FIG. 19, but may be similarly employed in those embodiments.

The plasma generator 11 of the invention may be formed on the same substrates that incorporate a DMS device. As shown in the illustrative embodiment of FIG. 19, a microchip 290 may be formed incorporating a plasma generator 11 of the invention, with mating opposed substrates 224 and 226 for the electrodes. In various embodiments, a separate plasma generator, such as that shown in FIG. 17, may be formed on each of the facing substrates or. Alternatively, a single plasma generator may be formed. A DMS device 240, having a filter 250 and optionally a detector 260 may also be defined within the same microchip structure 290.

In the analytical system 10 shown in FIG. 19, the carrier gas CG and sample S are introduced at inlet 265, and are ionized by the plasma process at plasma generator 11. The ionized particles are analyzed in the DMS device 240 (at the DMS filter 250). The filter 250 output may be directed to the input of a mass spectrometer or other detector device or simply to an onboard detector 260, as shown, as it flows toward the exhaust 266.

In various illustrative embodiments of the invention, separation of the substrates and accurate spacing of the electrodes is desirable and may be achieved as needed, such as by use of spacer parts 292 and 294 in the microchip structure 290 of FIG. 19. The substrates 224 and 226 are formed mated against the spacers 292 and 294, which may be integral extensions of the substrates, or a housing, or separate components, as needed, and may form a sealed structure.

As can be seen from the above discussion, advantages of the invention include that, in various illustrative embodiments, it provides a low-cost, non-radioactive, highly-efficient, clean and stable, radio frequency plasma ion source for using in fluid flows. According to other advantages, illustrative embodiments of the invention are capable of providing a wide range of plasma levels and are operable at low power over a range of pressures, including atmospheric pressure, in air or other gas environments. According to further advantages, illustrative embodiments of the invention are capable of ionizing a wide range of compounds, ranging from those having low ionization potential (such as acetone) to those having high ionization potential (such as $SF_6$), among various other compounds, for example.

Illustrative embodiments of the invention can also be operated with good control over formation of ions and ion species. As an illustration, the amount of energy in the plasma can be controlled, such as by control of the energy supplied by drive circuit 22. Control of the amount of energy imparted into the gas and the resulting plasma controls the ion species generated in the plasma. By enabling control this energy, the invention provides control of the formation of ions. This control may also be exercised to prevent formation of unwanted ions, such as nitrogen ions (NOx species), which can interfere with detection of other negative ions. This control can also be employed for increasing and/or decreasing fragmentation or clustering for a particular downstream use.

Figure 20A:
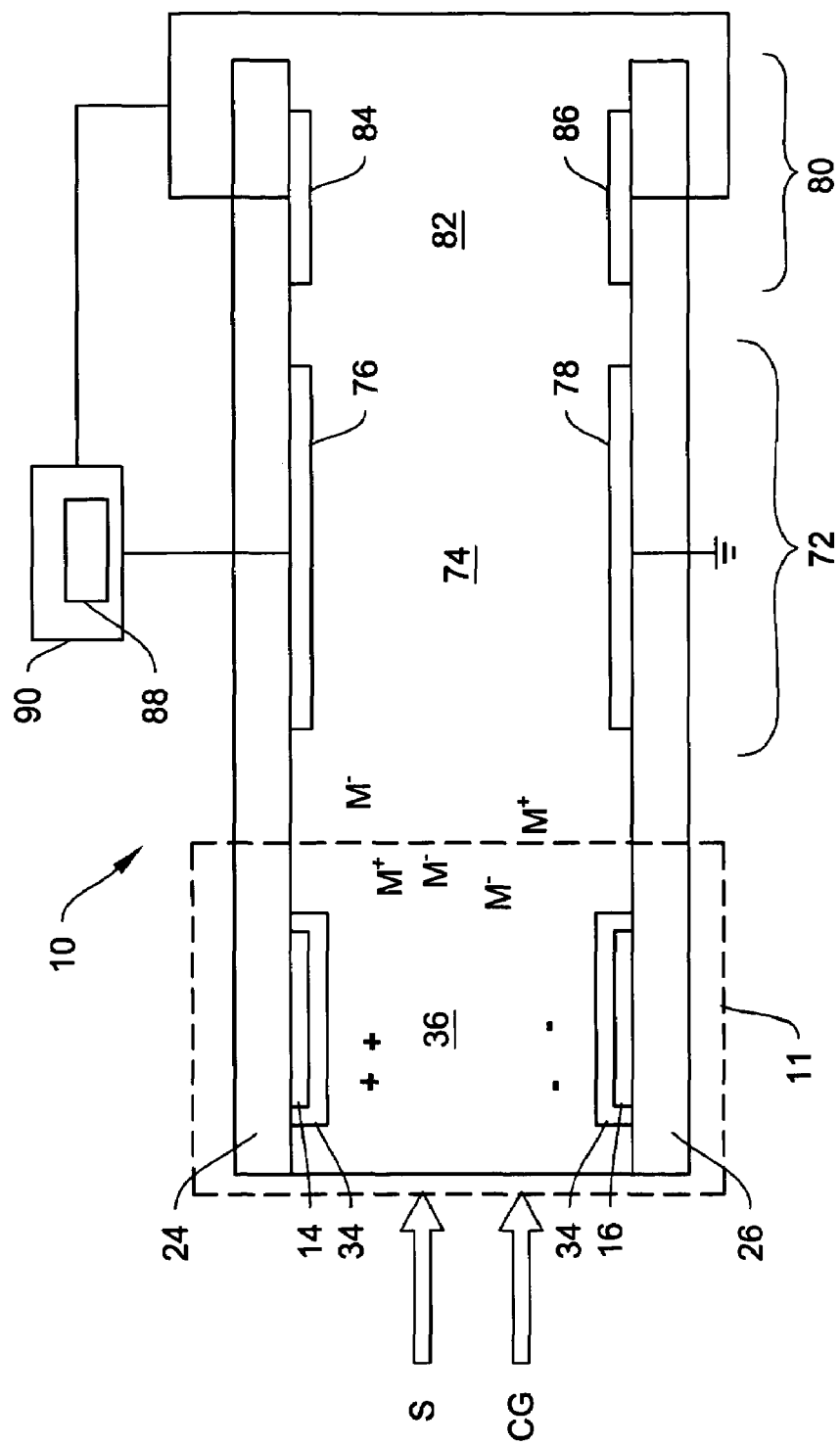

According to various illustrative embodiments, the ionization device 11 is suitable for use in many types of gas analyzers and detectors. For example, FIG. 20A depicts a DMS system 10 having an ionization device 11 upstream for plasma ionization. Ions are generated for chemical analysis of a sample S in a carrier gas CG.

More particularly, the system 10 of FIG. 20 includes an ionization source 11, an ion filter 72 in the filter region 74 defined between filter electrodes 76 and 78, and a detector 80 in a detection region 82 between detector electrodes 84 and 86. Asymmetric field and compensation bias signals or voltages are applied to the filter electrodes 76 and 78 by a drive circuit 88 within a control unit 90. The detector electrodes 84 and 86 are also under the direction of the drive circuit 88 and the control unit 90.

Briefly, in operation, the carrier gas CG, is ionized in the plasma region 36 forming ions ++,−− and the sample S is ionized creating both positive and negative ions, $M^+$ and $M^-$. Based on DMS ion filtering techniques, only certain ion species pass through the filter region 74, while others are filtered out (i.e., they are neutralized by contact with the filter electrodes 76 and 78). Those that pass through are detected at the detector electrodes 84, 86. Preferred DMS configurations are described in greater detail in U.S. Pat. Nos. 6,495,823 and 6,512,224, the entire contents of both of which are incorporated herein by reference.

Figure 20B:
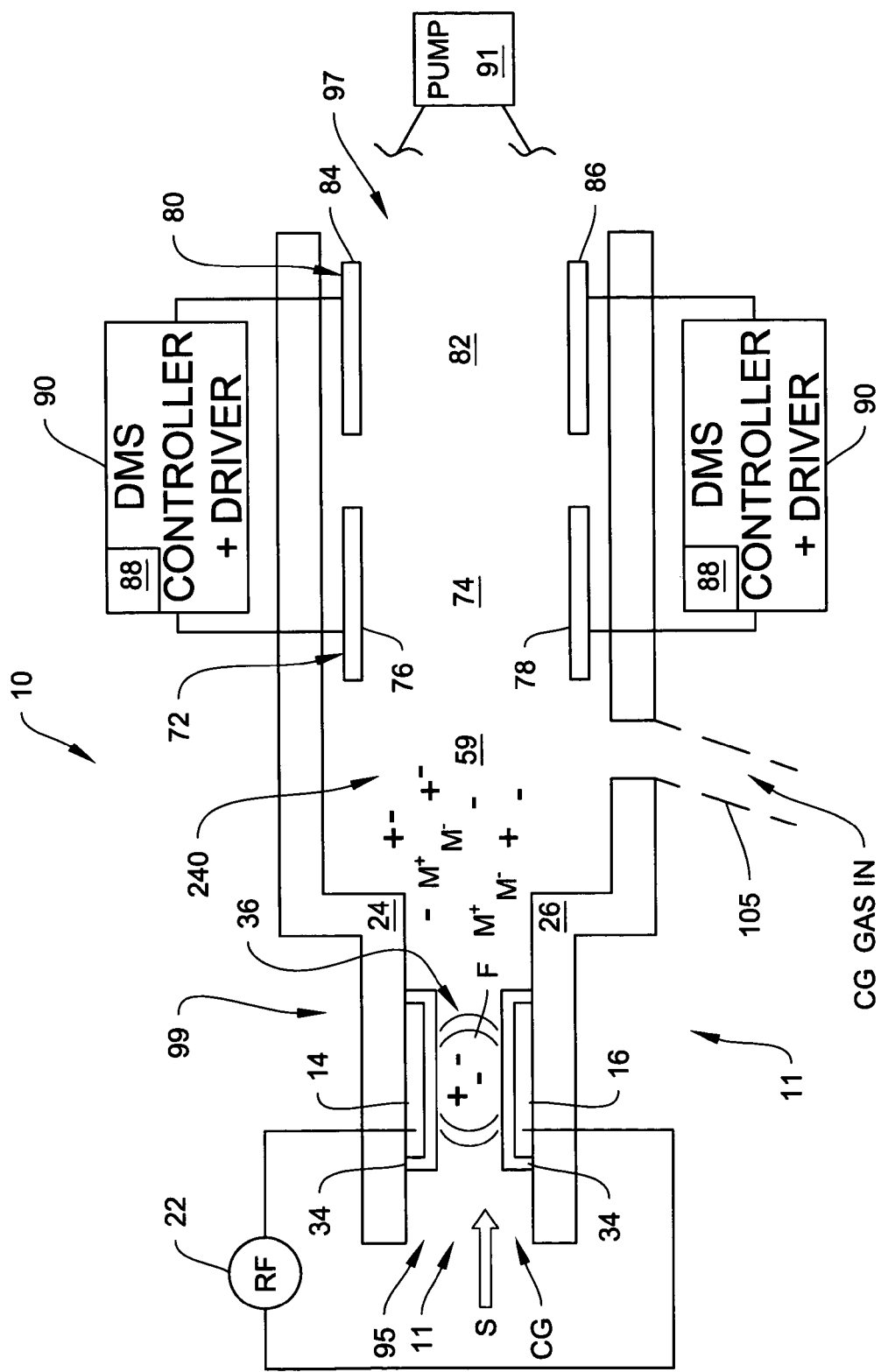

As depicted in FIG. 20A, the electrodes 14, 76 and 84 are coplanar and the electrodes 16, 78 and 86 are coplanar, being formed on the substrates 24 and 26, respectively. Alternatively, as shown in FIG. 20B, the system 10 includes a necked down, reduced diameter/width region 99 of the substrates in which the ionization source 11 and the electrodes 14 and 16, reside. In this configuration, the electrodes 14 and 16 are spaced apart by less than the distance separating the filter electrodes 76 and 78. This enables a closer orientation of the plasma generating electrodes 14 and 16, while a greater separation is provided for the filter electrodes 76 and 78.

In FIG. 20B, the capacitive discharge ionization source 11 is integrated with a DMS apparatus 240 in analytical system 10. The system 10 of FIG. 20B includes a filter 72 and detector 80 formed on the substrates 24 and 26. In this embodiment, at least one and preferably two of the electrodes 14 and 16 is protected from the plasma with a dielectric 34. The filter 72 applies a compensated high field asymmetric waveform to a pair of filter electrodes 76 and 78, which generates a high electric field there between. According to ion mobility characteristics of the ions passed into the DMS filter field, a species of ions is passed for detection at the detector electrodes 84 and 86 of the detector 80. In a typical DMS manner, the detection event is correlated with the applied drive voltages and known device performances to characterize the detected ion species. According to a feature of the invention, this can also be correlated with drive and control of the ionization device 11, for total analytical system control.

Positive and negative ions are generated in the plasma generator and consequently positive and negative sample ions are presented to the DMS filter. It is a characteristic of preferred DMS systems of the invention, including in-line plate-type DMS systems, that both positive and negative ion species can be filtered substantially concurrently, and in some embodiments substantially simultaneously. Those species requiring the same compensation will pass substantially concurrently/substantially simultaneously to the detector. The dual electrode detectors 84 and 86 then detect these passed species substantially concurrently/substantially simultaneously.

In operation, the carrier gas, with a sample of chemical compounds, is inputted at the upstream inlet 95 and the gas flows through the apparatus and out exhaust outlet 97. Gas flow rate and pressure may be controlled by use, for example, of a downstream exhaust pump 91. The DMS system is driven and controlled by controller and driver circuit 88, which may be incorporated into and packaged with the plasma controller and drive circuit 90. The plasma generating electrodes 14 and 16, filter electrodes 76 and 78, and the detector electrodes 84 and 86 may all be separate and distinct structures or may be formed as electrodes on the surfaces of the substrates 24 and 26, for example.

Figure 20C:
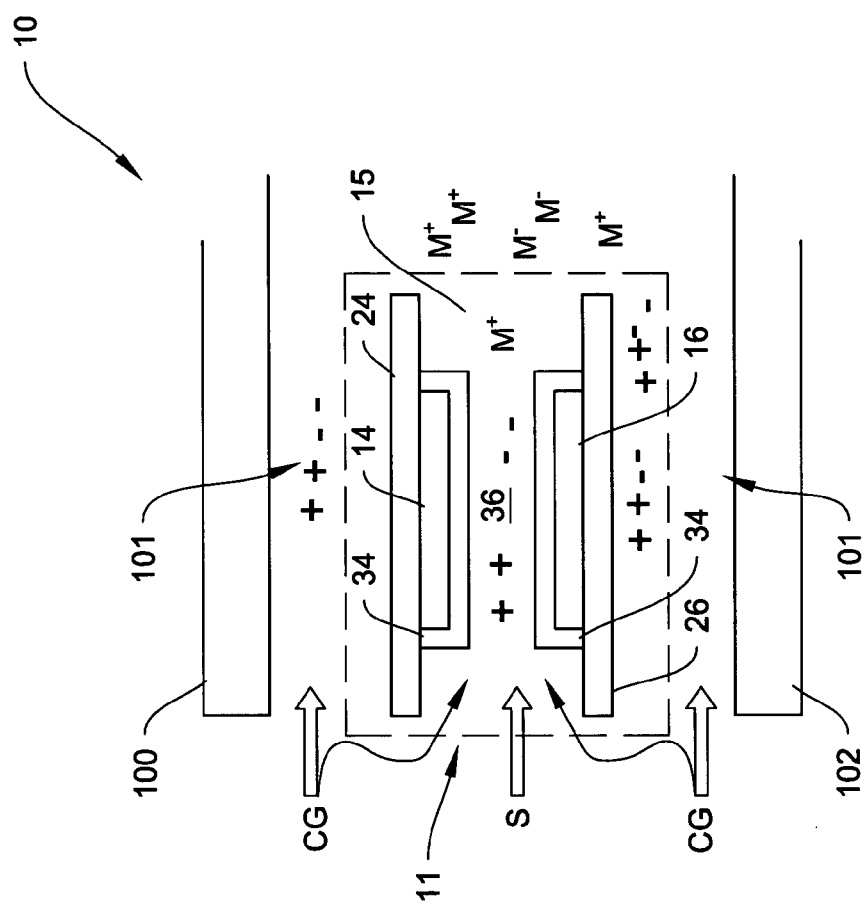

In another illustrative embodiment, shown in FIG. 20C, the ionization source 11 is located within a channel 101 in between the substrates 100 and 102. In this arrangement, the carrier gas CG, splits and partly flows within the ionization region 36, where it is ionized to form the plasma, ++,−−, and also outside of the ionization source 11. The sample S flows into the plasma ions ++,−− within the ionization region 36 and is ionized, but at a higher concentration versus the reduced carrier gas. These ions flow out of the ionization source 11 and are carried downstream for further analysis.

In the embodiment of FIG. 20C, the efficiency of ionization of the sample is increased by reducing the amount of carrier gas in the ionization region. In an alternative embodiment of the invention, also shown in FIG. 20B, to increase the ratio of the sample S to the carrier gas CG, and to increase the efficiency of ionization of the sample S, the sample S is introduced into the ionization source 11 with a reduced, and preferably minimized, amount of carrier gas CG. The carrier gas is ionized within the plasma. The sample is also ionized. All of this flows into a flow mixing and sample ionization region 59, where a second stream of carrier gas CG is introduced via an additional inlet 105 (shown in dotted outline in FIG. 20B) to carry the ions downstream toward the filter 72 for further analysis. A feature of this embodiment is that a lower amount of background gas is ionized, which relatively increases the ratio of the ionized sample to the ionized carrier gas, thus reducing the effect of the reactant ion peak in the analysis and improving the effective ionization chemistry.

Figure 20D:
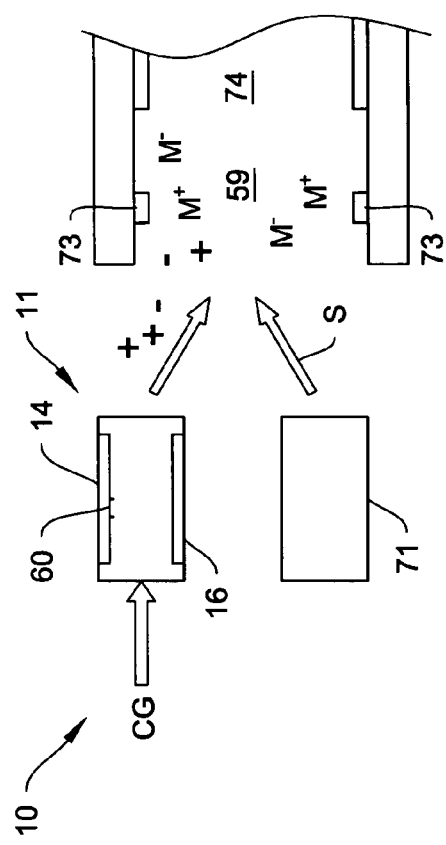
Figure 20E:
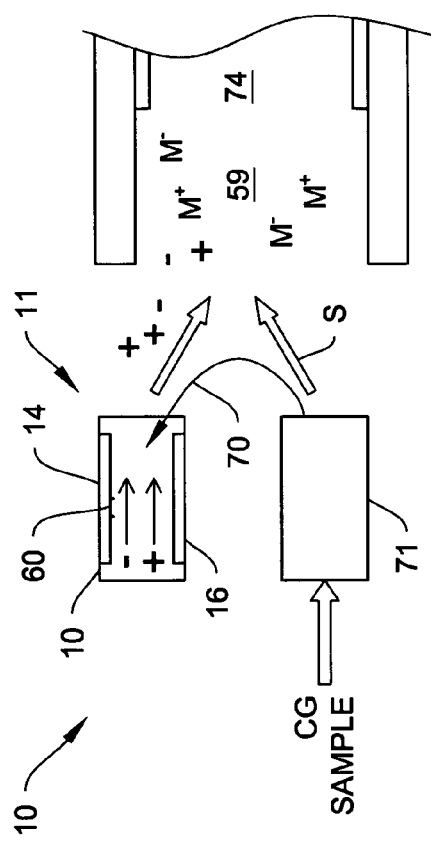

Referring now to FIG. 20D, an alternative system of the invention 10 includes plasma ionization device 11 which receives a carrier gas flow CG. The carrier gas is ionized and these ions ++,−− flow into an ionization region 59 where sample S from the source 71 is ionized. The sample S is delivered to the ionization region 59, such as by a flow of carrier gas from the source 71 after the plasma ions are generated. The sample is ionized in the region 59 and the ionized sample molecules M+, M– are then carried downstream accordingly. This arrangement avoids the complex ionization chemistry that can occur when ionizing sample within the plasma ionization section 11, and also can reduce unwanted affects of plasma ionization chemistry upon the sample ionization and downstream analysis In a further embodiment, biased accelerator electrode(s), 73, such as shown in FIG. 20D, can be provided to assist delivery of selected portions of the ionized sample into the DMS filter region 74. In another illustrative embodiment, shown in FIG. 20E, a counter flow 70 of carrier gas and sample is carried into the ionization device 11 for ionization. These ions then flow downstream to the sample ionization region 59 for ionization of the sample and generation of ions to be analyzed. The counter flow 70 sweeps the flow of unwanted ionization products away from ionization region 59. Also, a variety of gases which are different from the sample can be mixed to create ions, e.g., use of dopants such as acetone, water, etc.

FIG. 20F shows a plural channel embodiment 10 of the invention, including a first flow channel 270 having a plasma ionizer 11, which receives the gas flow CG and generates the ions ++,--. These ions flow into an ion diverter, which may be a baffle or another gas flow, to influence and redirect the ion flow. Preferably, the diverter is selective. For example, FIG. 20F includes a diverter 271, which diverts selected ions into second flow channel 272 through opening 273. The remaining flow and other by-products of the plasma ionization process are exhausted out of flow channel 270 at vent 280.

The diverter may also be a biased electrode. In one embodiment, as shown in FIG. 20F, diverter 271 includes first and second electrodes 274 and 275 which are independently biasable. In one illustration, electrode 274 is negatively biased which drives the negative ions --,-- generated in the plasma ionization part 11 through access 273 into a sample ionization section 276 in the second flow channel 272, with the negative ions flowing toward the positively biased electrode 275. These negative ions –,– ionize the sample S and carrier gas CG, and thus provide sample ions S–, S– for downstream analysis.

Preferably, as in FIG. 20F, DMS filter 277 and ion detector 278 are associated with flow channel 272. The DMS analyzer benefits from splitting the ion flow, such that the sample is isolated from the harsher ionization chemistry that occurs directly within the plasma generator 11. In a further embodiment, the pressure in the first flow channel 270 can be kept slightly lower (for example, and without limitation, about 0.95 atm) than in the second (for example, and without limitation, about 1 atm) so that a sweeping counter-flow keeps unwanted plasma ionization by-product from flowing into the second channel 272; this pressure gradient is indicated by the dotted arrows 279.

According to another feature of the invention, the plasma intensity can be modified, modulated, and/or otherwise adjusted. In one illustrative embodiment, the plasma and ionization chemistry occurring in the plasma generator is favorably modified by controlled introduction of a doping gas D (FIG. 20F), for example, acetone. In this manner, plasma formation and ionization efficiencies can be increased as needed, which then reduces the hysteretic effect of plasma ignition and burn. One result is that the plasma ignition may be assisted, such as with a pulse of dopant, and/or the ionization intensity may be sustained or operated at a higher level by continued flow of dopant and at lower power. Thus, high, middle, and low output intensities can be achieved through use of such a control mechanism.

Use of the dopant for ignition reduces the energy required from the power supply, reduces the destructiveness of ignition, reduces heat generation, simplifies circuit design and simplifies power sourcing logistics, while sustained use of the dopant reduces the keep alive energy required to sustain the plasma. These contribute to lower power demand and reduced wear and longer life of the plasma source.

Another advantage of introduction of dopant D into the dual channel apparatus of FIG. 20F, is that the dopant accelerates and assists plasma ionization in the first flow channel 270 and then unwanted ionization by-products are exhausted via the vent 280, while sample ionization proceeds in the second flow channel 272.

Additional illustrative embodiments of the invention include arrays of plasma sources, flow channels, analyzers, and the like, each of which may be operated under different conditions, such as with dopants D, excitation energies, plasma intensities, analytical conditions, and the like, all to better control the analytical process.

Dopants may also be utilized in illustrative embodiments of the invention according to the teachings of U.S. patent application Ser. No. 10/462,206, filed Jun. 13, 2003, for METHOD AND APPARATUS FOR CONTROL OF MOBILITY-BASED ION SPECIES IDENTIFICATION, by Raanan A. Miller, et al., the entire contents of which are incorporated herein by reference.

FIGS. 20G–20I show three illustrative arrays of the invention. In FIG. 20G, the analytical array 200 includes a plurality of parallel flow paths 12, each having a plasma ionization source 11 and DMS analyzer 20, the latter including a DMS filter 72 and detector 80. Sample, carrier gas and dopant, if any, are delivered into the flow path for ionization and analysis. The plasma generator is capable of delivering positive and negative ions simultaneously, while each DMS is capable of analyzing the same simultaneously and issuing an output indicating detection of both ion modes simultaneously. Therefore, having a parallel array according an embodiment of the invention enables a robust analytical effort to be amassed for a given task. Fast and reliable species identification is provided.

Each flow path may appear as shown in FIG. 20G. An alternative configuration is shown in FIG. 20H, where illustrative flow path 12 has a first plasma ionizer 11 and a first analyzer. Dopant may be introduced into the plasma generator 11 along with the carrier gas CG, or dopant may be introduced along with the sample S into the less harsh environment of the downstream sample ionization region 59. The ionized sample is filtered 72 in the analyzer and detected at the detector 80, which provides a first set of data relating to sample identification. The sample is neutralized as it exits the detector 80, and therefore can be re-ionized and reanalyzed and redetected under the same or different conditions in the next in-line plasma ionizer 11, and the analyzer 20, as shown. A more robust analysis of the sample can be thus rendered.

In one additional embodiment, shown in FIG. 20I, the carrier gas CG is introduced and ionized in the plasma generator 11 and the sample S is introduced downstream and is ionized in the sample ionization region 59. The sample ions S+, S–, can be ionized in the analyzer 20 in the flow path 12a. However, the deflector electrode(s) 83 can be biased, as needed, to deflect a positive or negative ion mode. For example, if the electrode 83 in the flow path 12a is biased negatively, then negative ions S– can be deflected into the flow path 12b and further analyzed. The electrodes 83 may also be provided in flow path 12*b*, and in this example, can be positively biased to attract the deflected ions. The carrier gas CG transports the ions S−, S− into the DMS analyzer 20 accordingly. The remainder of the ion flow in the flow path 12*a* can be processed or reprocessed downstream or can be vented, as desired, for the particular analytical goal at hand.

In a further illustrative embodiment, the invention provides a configuration that reduces the complexity of chemical reactions occurring during the ionization process. As discussed above, the sample S and carrier gas CG flow into the plasma 40 in the gap between the plasma source electrodes 14 and 16 and are thus ionized. Such ionization can produce a complex chemistry. As described earlier, if the gas is air, it can produce both positive and negative ions, usually including $(H2O)_n$, $H^+$, $O^-$, $O_2^-$, $O_3^-$, $(N_xO_n)^+$, and $(N_xO_y)^-$ $(H_2O)_n$).

At times, such complexity can interfere with ionization and detection of particular analytes in the sample S. This can occur, for example, when plasma formation and direct ionization of the sample in air includes formation of $NO_2$, which can interact with the sample and interfere with negative mode sample detection. Therefore ionization of sample without formation of $NO_2$, and the like, is desirable in many cases.

Figure 21:
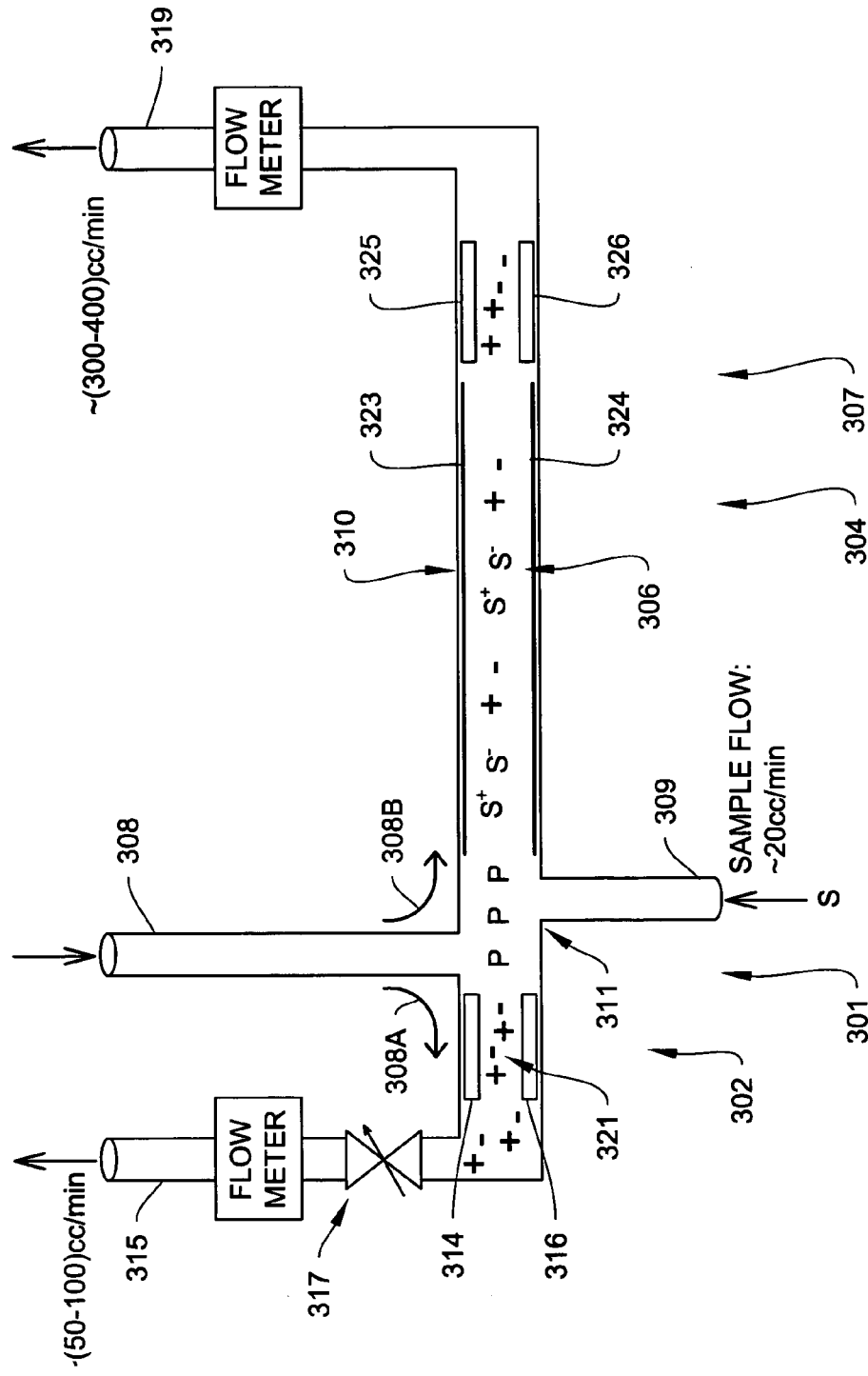
FIG. 21 is a diagram of an illustrative DMS system having a plasma photo-ionization source and split gas flow according to an illustrative embodiment of the invention.

FIG. 21 shows an illustrative embodiment of the invention that addresses the challenges associated with complex chemistries by providing a windowless UV ionization source. Such a photon ionization source is desirable for many applications and is shown in conjunction with an illustrative downstream DMS filter system.

More particularly, the analytical system 300 includes a plasma ionization section 301 and a DMS filter section 304, coupled by flow path 306. Optionally, the system 300 also includes a downstream detector section 307. The flow path 306 includes a transport gas inlet 308 at the downstream end of plasma source 302 and a further downstream sample inlet 309 upstream from the DMS filter 310. The flow path 306 extends between an upstream outlet 315 via a needle valve 317 and a meter 318 above the plasma source 302 and a downstream outlet 319 the below detector section 307. The gas flow from the source 308 is split into an upstream flow 308A and a downstream flow 308B, which may be regulated by control of the needle valve 317.

The transport gas is ionized to generate ions and photons in the plasma generated between the electrodes 314 and 316 of the plasma generator 302. The ionized gas flow and its products is carried by the flow 308A to the outlet 315 away from the filter section. However, the photons P generated in the plasma section, travel downstream adjacent to the sample inlet 309, in a photo-ionization region 311, into the ion filter section 304 between DMS ion filter electrodes 323 and 324. Upon filtering, the ion species of interest are passed by the filter into the detector 307. According to this illustrative embodiment, both positive and negative ion modes of the passed species are detected substantially concurrently/substantially simultaneously at the oppositely biased detector electrodes 325 and 326, with the expended flow then proceeding to the outlet 319.

Thus, in various illustrative embodiments, the invention provides a highly functional windowless UV ionization system. This windowless function avoids the degradation of the UV window. As has been observed, $NO_2$ can interfere with the detection and identification of ion species, either by obscuring detection of an analyte, causing peak shifts, or the like. When the carrier gas is air, ionization of the carrier gas can generate $NO_2$. Another benefit of photon-based ionization of the sample S and the carrier gas CG in the flow 308B in the photo-ionization section 311 is that the production of $NO_2$, and its interaction with species formation is significantly reduced. The reduced $NO_2$ stream then flows into the analyzer 304.

According to the illustrative embodiment of FIG. 21, a first gas flow 308A, which may be referred to as a counter-flow or curtain gas, is directed into the plasma ionization section 302 to generate the plasma 321. The ionization by-products are swept from section 302 by the flow 308A away from the photo-ionization region 311. Thus, photons from the plasma enable photo-ionization of the sample S to proceed without $NO_2$ interferences. This embodiment therefore provides an improved photon source and an improved sample photo-ionization environment.

Figure 22:
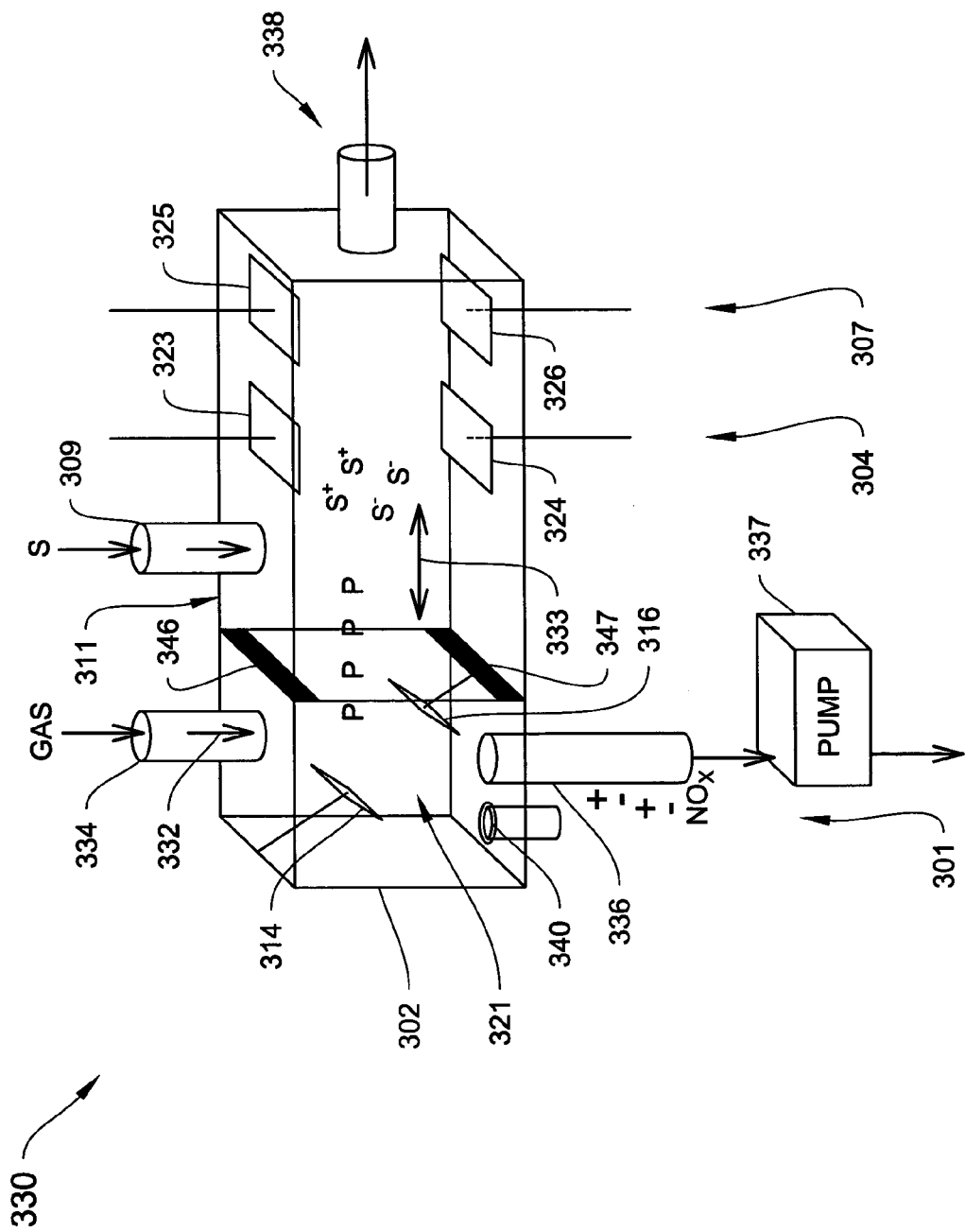
FIG. 22 is a diagram of an alternative illustrative embodiment of the analyzer and plasma photo-ionization source of FIG. 21.

FIG. 22 shows a system 330 employing an alternative photo-ionization embodiment of the invention. The system 330 performs similarly to the system 300, but with a different flow pattern. More specifically, the system 330 includes a plasma ionization section 301, a DMS filter 304, and a detector 307. An ionizable gas flow, such as the air flow 332, flows from the inlet 334 to the outlet port 336 between the electrodes 314 and 316 and through the plasma 321 formed by plasma generator 302. This is at the upstream end of the flow path 333.

Ions and other by-products are generated in the plasma and are exhausted from the flow at the outlet port 336. The exhausting may be assisted by a controlled pump 337. The photons P are also generated and flow into the sample photo-ionization section 311 adjacent to the sample delivery port 309. The soft ionization of the sample, the DMS species filtering, and the detection then proceed, as earlier described, with little or no unwanted effects from the plasma ionization process.

A portion of the gas inflow 332 splits into the flow path 333 and flows downstream, carrying the ionized sample from the photon-ionization section 311 and into the downstream analyzer's DMS filter 304. The carrier gas CG and sample S that are ionized and generate ions +,−, including ionized sample S−,S+, flow into the analyzer section 304 (DMS filter), without generation of $NO_2$ and avoiding other process complexities. In one aspect, interaction of the photons P and the sample S is at least partially responsible for producing the ionized samples S+ and S−.

Thus, in these embodiments, a first gas flow is for formation of plasma, wherein the flow also sweeps unwanted ions and the like away from the photo-ionization section. The photo-ionization of sample may be achieved using a second separate gas flow, or a split flow as shown earlier, such as where the pressure from the sample inlet side is higher than present in the plasma ionization region 301. But in any event photo-ionization transpires in a controlled environment and avoids the formation of $NO_2$ and the like, enabling improved downstream ion species analysis.

In a further embodiment of the invention, a strategy for controlling plasma level is provided. Open loop techniques can be used for this purpose but make it difficult to accommodate non-linearities in plasma generation. In a preferred embodiment, a feedback loop is formed to enable close regulation of the output of the plasma generator. Referring to FIG. 22, photo-detector 340 is placed adjacent to the plasma source 321. Now, the level of emission or generation of photons within the plasma source can be detected and used as a measure of plasma output. Photons continue to flow into the photo-ionization section without interference, while photons which otherwise would not travel into the photo-ionization region are detected by photo-detector 321.

This detector connects to the system controller, such as controllers 22*d* (FIG. 1C) or 222 (FIG. 20B), enabling detection and maintenance of the plasma/photon level by direct measurement. We have found that light intensity is directly proportional to plasma/ionization level, and therefore is a good performance measure.

In one embodiment, a conventional photo-detector, with response near the emission wavelength of 400 nm was used to measure the light intensity. As a result, the drive signal to the plasma generator was controlled to regulate the plasma and/or photon intensity at a desired steady state. This enabled ionization of the sample S to proceed under preferred and expected conditions. In a further embodiment, a photo-spectrometer was used to more completely tune the photon spectral output.

In a further embodiment of the invention, the filter electrodes 323 and 324 are substantially simultaneously RF-driven and DC-biased and act as attractor electrodes, which draw ions from the plasma ionization source 302 into the photo-ionization section 311 for increasing ionization efficiency of the media thereat in the second gas flow.

In the embodiment of FIG. 22, the control electrodes 346 and 347 are driven to attract or repel positive and/or negative ions and therefore, control introduction of such ions into the photo-ionization section for additional control of the ionization process in the photo-ionization region 311. The plasma drive according to various illustrative embodiments of the invention will now be discussed. Returning to FIGS. 1A–1C, it will be appreciated that use of the resonant drive 22 for generating plasma at plasma source 11 for producing a high frequency RF plasma field decreases power consumption. In a preferred embodiment, the resonant drive circuit 22 also provides system stability via a feedback loop. More particularly, it will be appreciated that plasma pumping energy strongly depends on field strength. If applied voltage and/or frequency (and electric field correspondingly) rises, then discharge energy increases. This results in increasing rate of ionization and, consequently, an increase in discharge activity. Unchecked, this increase can result in a excessive increase in plasma energy and heating.

In one embodiment, the electrodes 14 and 16 act as a capacitor in L-C resonant circuit 22*c*. If the capacitor's conductivity increases, then the Q-factor of the resonant circuit decreases. Since applied voltage is proportional to the Q-factor, the voltage decreases as well. Thus, the electrodes 14 and 16 are part of a negative feedback loop for maintaining the plasma at a desired energy level for a given drive voltage and frequency, preventing runaway plasma growth and overheating.

A particular drive circuit 22 design depends on target plasma levels and electrode and gap dimensions. Nevertheless, typically, an AC voltage, with an amplitude sufficient to produce a large electric field F, is required to initiate and maintain the discharge in atmospheric conditions. The reactive power in the megahertz frequency range is on the order of tens of watts for a capacitive load of tens of picoFarads. Therefore, an illustrative embodiment of the invention employs a resonant oscillator, with a capacitive load as a component of the output LC-circuit.

In further embodiments of the invention, modulation of the plasma generator drive signal reduces power consumption. Use of such modulation improves spectrometer performance (whether such modulation is small signal, large signal, analog, digital or otherwise). This modulation encodes the ionized sample signal to be detected.

This characteristic modulation can be used to discriminate against noise contribution that is spread over a different and wider band of frequencies. An AC coupled amplifier, with a narrow band filter centered on the modulation frequency, significantly increases the signal to noise ratio of the spectrometer. Additionally, the filter frequency pass band can be narrowed to the limit of the modulator stability. Alternatively, if noise contribution is still too high or to negate modulator signal drifts or shifts, lock-in techniques, such as actively tracking the modulator frequency and using a narrower filter band, can be employed.

Several benefits of ionization modulation can be obtained in practice of the invention. These benefits include, without limitation: improved signal to noise ratio, ionization of selected chemical species, reduced ionization of interfering species, improved detector performance, optimization of system power use.

The invention is not limited to use of inert gases, as in some prior art systems. The invention has improved configurations, with use of a broader array of gases, including air (whether filtered, ambient, or processed zero air), depending upon species being detected. The invention, in various illustrative embodiments, also incorporates the ability to change plasma source intensity by control of how it is excited, such as with a signal varying between 10's of kHz to 100's of MHz. By way of example, in one low power embodiment of the invention, the plasma is driven at about 1 MHz. The plasma ionization source of the invention may be driven using various drive circuits, whether LC, transformer, resonant, H-bridge, planar magnetic, or the like. It is a further benefit of the invention that the plasma ionization source, in various configurations, is designed to be integrated into and/or used with a mass spectrometer and/or ion mobility based analyzer, and preferably a DMS filter/detector.

The plasma source of the invention has various applications, and a preferred embodiment is used in conjunction with a DMS analyzer. An illustrative plasma drive circuit of the invention is shown in the context of a DMS chemical analyzer in FIG. 23. The system 400 generates and analyzes ions according to the invention. The system 400 includes an ionization source 405 and DMS spectrometer 408 (having a filter and detector). The ionization source 405 ionizes fluids, such as gases, and the spectrometer 408 filters the ionized gases and detects the gas ions that pass through the filter. The system 400 includes a flow path or channel 104, which may be at atmospheric pressure, in which the ions travel.

The ionization source 405 includes a plasma source interface 406, which includes first and second differential source electrodes 407*a* and 407*b* (collectively, source electrodes 407), and a Radio Frequency (RF) source driver 420 connected to the source electrodes 407. In response to a sufficient voltage being supplied across the source electrodes 407, a discharge field is established. A gas sample 440 is flowed into the field between the source electrodes 407. The gas sample 440 is ionized by capacitive discharge between the source electrodes 407. This discharge ionization produces a plasma from the plasma source 435, with both positive and negative ions.

In a preferred DMS spectrometer 408, forming these ions enables chemical analysis of compounds, where ion species are separated based on differences of mobility in a DMS filter field. Spectrometer 408 includes a filter 410 and detector 415. The filter 410 includes an ion interface 411 and filter driver 425. The ion interface 411 includes filter electrodes 412*a* and 412*b*. Similarly, the detector 415 includes a filtered ion interface 416 and detector processor 430, that latter which may be provided as an on-board component or as a separate device. As shown, the filtered ion interface 416 includes detector electrodes 417a and 417b.

A gas plasma source 435 is ionized by the discharge in an RF field between the source electrodes 407. The plasma in turn ionizes the gas sample 440 and forms ions 445 (e.g., $M^+$, $MH^+$, and $M^-$). Generated ions exit the ionization source 405 to the spectrometer 408 for analysis.

Driver electronics are provided to drive the electrodes of the ionization source 405 and the filter 410. A source driver 420 is connected to the source electrodes 407. A filter driver 425 is connected to the filter electrodes 412a and 412b. In addition, detector processing 430 may be applied to measure the ions 445 received by the detector electrodes 417 that improves the performance of the detection of the ions 445 based on known characteristics of the source driver 420. The characteristics may be provided by the source driver 420 to the detector processing 430 via a bus 450.

The plasma source driver 420 enables plasma generation. Electronics used to generate plasma are typically of high power, high cost, and low reliability due to high frequency, high voltage, and complex load presented by the plasma source. In contrast, a preferred embodiment of the source driver 420, according to the principles of one aspect of the invention, generates low energy plasma using low power (< about 1 W) and enables linear control of the plasma intensity enabling fine control of the ion 445 generation.

Controlling plasma intensity by varying applied voltage is difficult due to the hysteretic and threshold nature of the plasma. FIG. 24 is a plot indicating the area of hysteresis. The plasma intensity at points A and B are more than necessary, if not too much, for the detector 415. In other words, at the level of high optical intensity as shown on the curve, there are too many ions for sensitive measurements to be made when fine measurements are desired. A non-modulated voltage produces the sharp curves as shown in FIG. 24, which includes the hysteretic band between points A and B. Thus, low optical intensities cannot be achieved through use of a source driver that provides voltages in a manner producing such curves.

In contrast, FIG. 25 provides a curve resulting from the source driver 420 producing a duty cycle modulation on the drive signal. By duty cycle modulating a switching waveform applied to the plasma source 435, linear control of the intensity of ions produced can be achieved. In an example ionization source, a 3% duty cycle as shown in FIG. 25 may be optimum for generating plasma. In an example DMS system 408, this enables reliable and sensitive measurements at detector 415.

In addition to allowing linear control of the ion production, modulation information associated with the source driver 420 can be used to improve signal-to-noise ratio of the recovered signal by the detector 415. The applied modulation, shown in FIGS. 26A–26C, results in the ions 445 being produced at the modulation frequency (e.g., 2 kHz). The ions 445 may be interchangeably referred to as ion packets 445 hereafter. Knowing this frequency and allowing for a measurable phase delay down the length of the channel 104 of the system 400 allows for the use of synchronous detection of the ion packets 445. The modulation frequency may be provided to the detector processor 430 via the bus 450. This results in large improvements in the signal-to-noise ratio as a result of reducing sensitivity of the detector 415 to signals of any other frequency and phase.

The modulation itself may be designed to operate a transformer (not shown) employed by the ionization source 405 at resonance (e.g., 2 MHz) with a peak-to-peak voltage of sufficient amount to produce the ion packets 445, such as a signal level of 2500 Vpp. By providing the modulated signal at a given duty cycle, such as about 3%, plasma intensity sufficient to produce ion levels compatible with the detector 415 can be achieved, which in one example is at about 100 mW.

Other benefits beyond the savings in power may also result from operating at lower energy states. For example, the ionization source 405, when operated in accordance with the intensity curves of 23A, generates a relatively high amount of ozone, which may interfere with sensing of the ion packets 445. Moreover, the ion packets 445 of high energy level can cause breakdown, caused by thermal effects and ablation, of uncoated electrode plates 407a and 407b and 412a and 412b, or isolation materials used to protect the electrodes. For example, in some previous designs, the electrodes and/or isolation materials have a typical lifetime of about 100 days. With this new, lower energy technique, the electrodes and/or isolation materials may last indefinitely. In addition, the heating of the electrodes 407 in the ionization source 405 is caused by the high energy states of the plasma source 435 in previous techniques; however, with this new, low energy technique, heating does not occur to significant levels and heat sinks are not necessary, which allows the system 400 to have a smaller overall design, lighter weight, and be better suited for a hand-held design.

Figure 23:
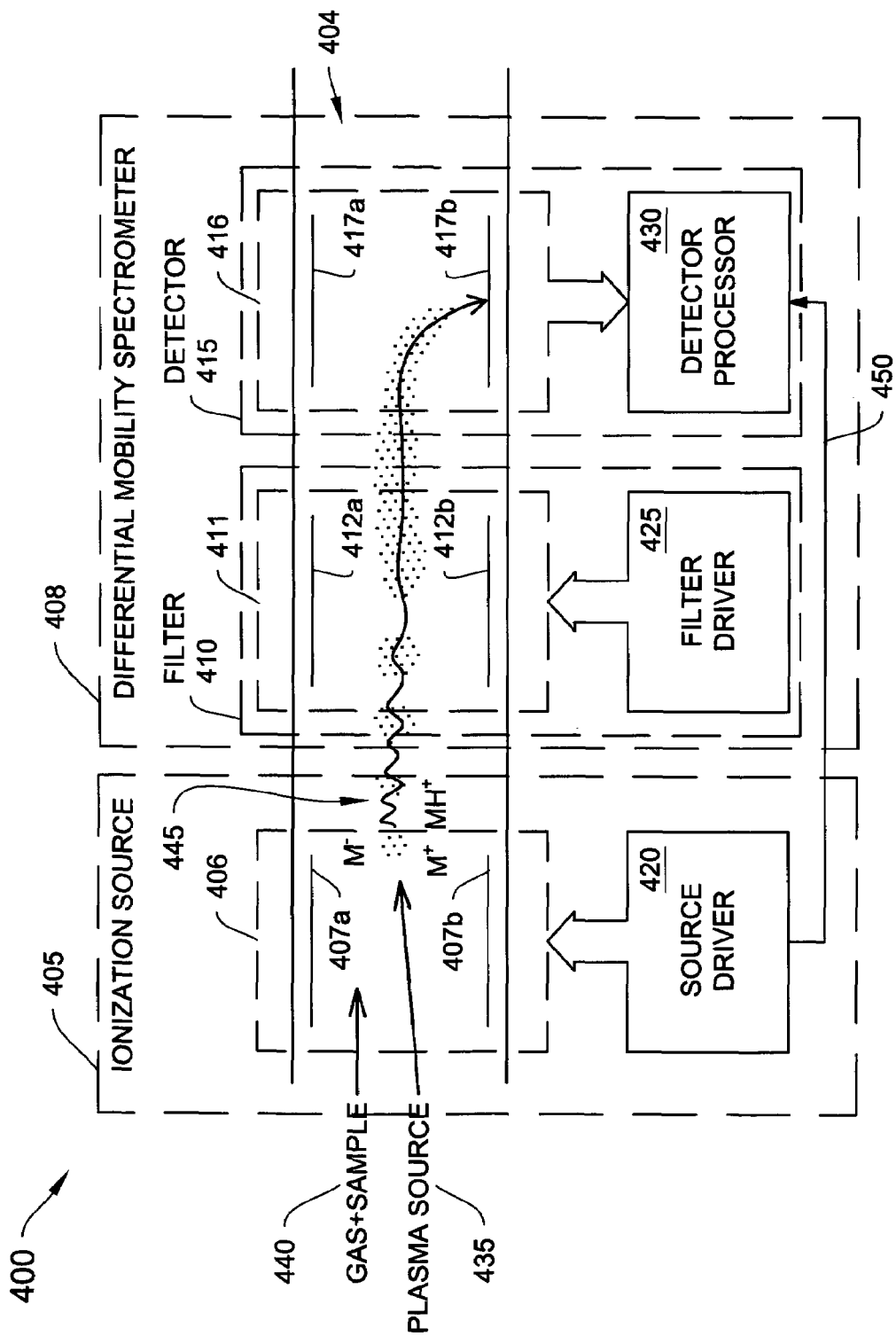
FIG. 23 is a block diagram of a system including a differential mobility spectrometer connected to an ionization source employing the principles of the an illustrative embodiment of the invention.
Figure 28:
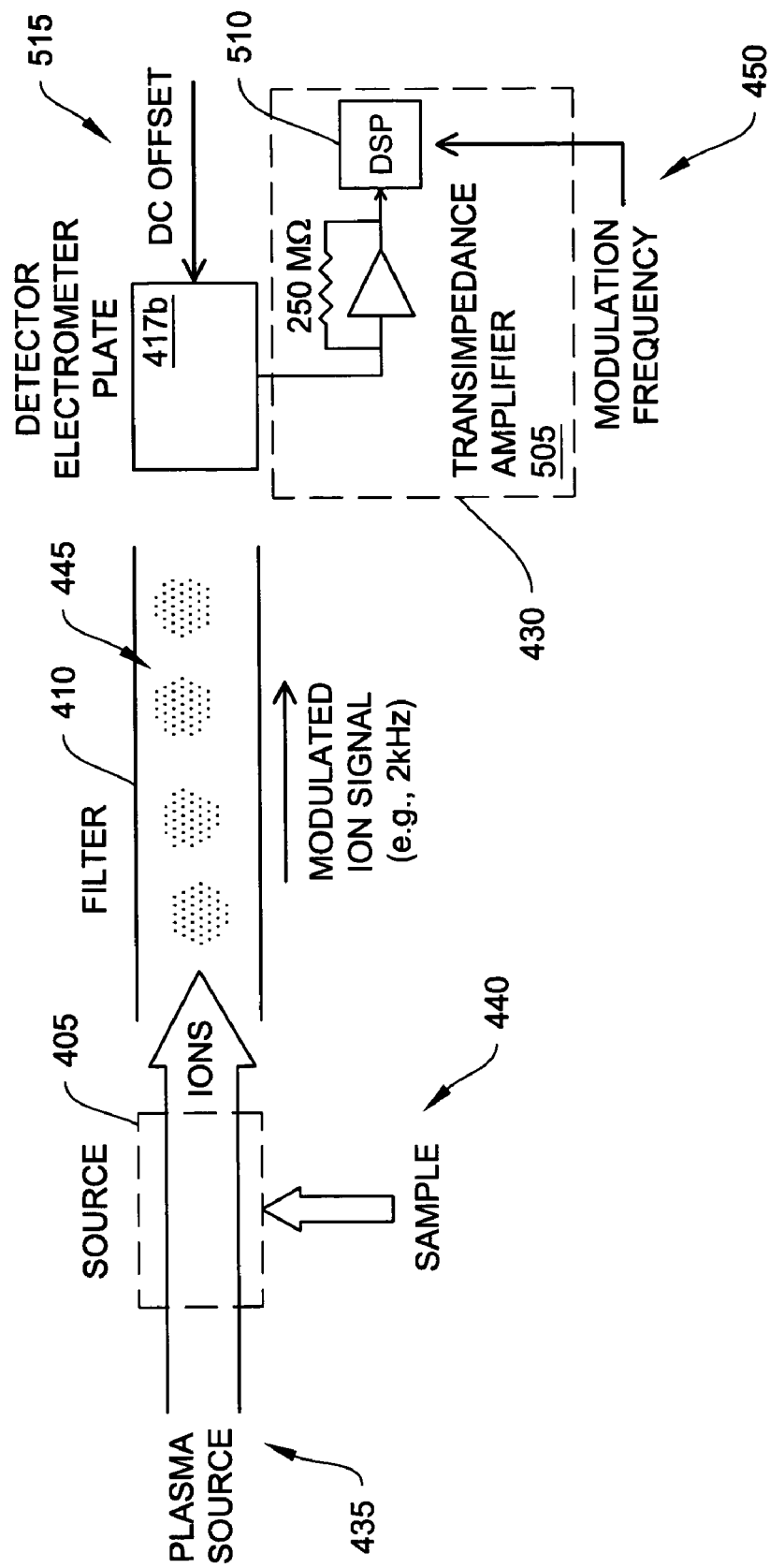
FIG. 28 is a block diagram showing ions produced in the system of FIG. 23 in response to the drive signal of FIG. 27, and also including a schematic diagram of a detector circuit to measure the ions.

Referring now to FIG. 23 and FIG. 28, the ionization source 405 produces ions in ion packets 445, which are filtered by filter 410 such as by DMS techniques. In one embodiment, the ion packets 445 passed by filter 410 are received at detector electrometer plates 417. One of the detector electrometer plates 417a is positively charged with respect to ground, repels positively charged ions in the ion packets 445, and attracts negatively charged ions in the ion packets 445. The other of the detector electrometer plates 417b is negatively charged with respect to ground, repels negatively charged ions in the ion packets 445, and attracts positively charged ions in the ion packets 445. The DC offset 515 from ground is applied to the two detector electrometer plates 417, although only plate 417b is shown in FIG. 28.

Detection of the ions 445 at the detector electrometer plates 417 results in a small (e.g., pico amps, pA) amount of current that is then amplified by, for example, a transimpedance amplifier 505. The transimpedance amplifier 505 may include, for example, a feedback resistance element of tens to hundreds of mega ohms (Mohms). Thus, the small current is amplified to a voltage range that can be interpreted by a processor 510, such as a digital signal processor (DSP).

Figure 26A:
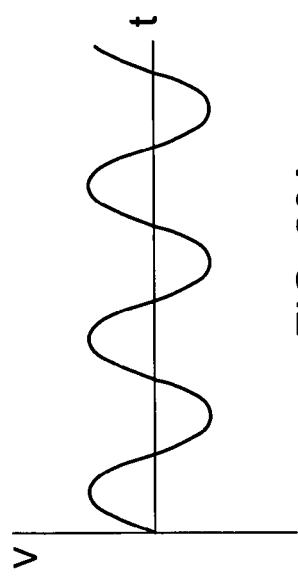
FIGS. 26A–26C show graphs of illustrative waveforms for driving a plasma generator of the invention.
Figure 26B:
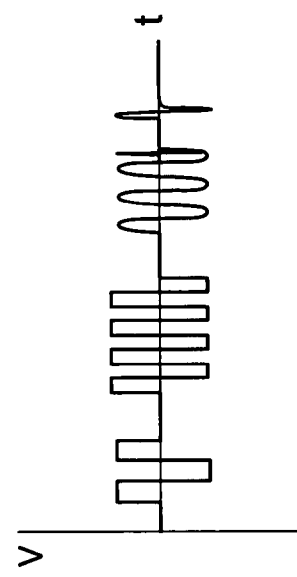
Figure 26C:
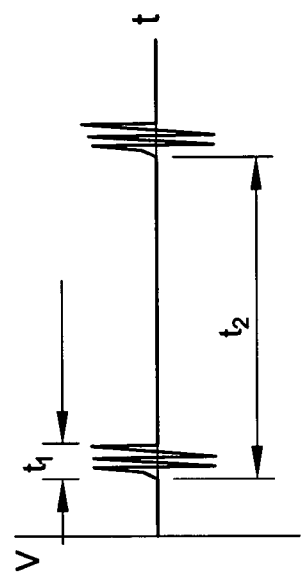
Figure 27:
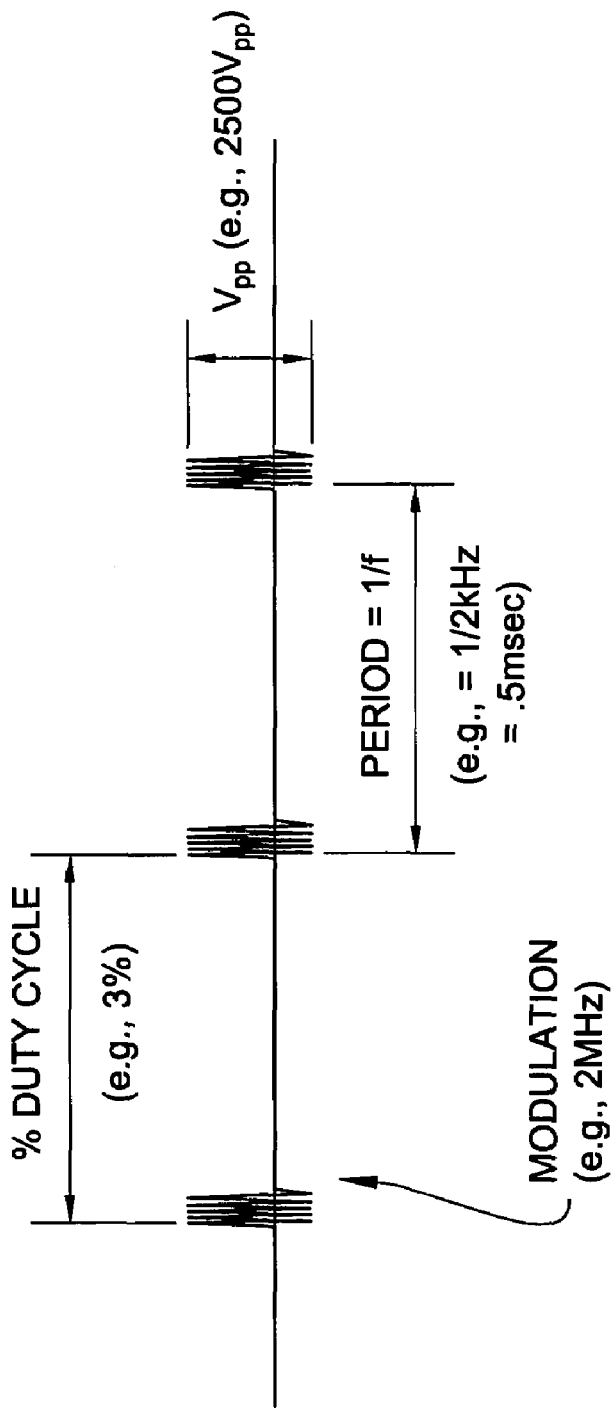
FIG. 27 is a time plot of a modulated drive signal having a duty cycle used to produce an output consistent with the graph of FIG. 25 according to principles of an illustrative embodiment of the invention.

In various illustrative embodiments, the plasma field has an RF component that may be of a standard or custom shape (e.g., sinusoidal, bias offset, pulse width modulated, or otherwise). For example, embodiments of the invention are operable with a sinusoidal high frequency high voltage waveform applied to plasma electrodes 14 and 16, as shown in FIG. 26A, modulated as in FIG. 26B or pulsed ("packetized") as in FIG. 26C.

Use of the packet waveform increases discharge stability, decreases power consumption, and further controls ionization efficiency. More specifically, the pulsed design follows from the recognition that a finite time interval is required for the plasma instability to reach the macrolevel. Therefore, energy is delivered to the discharge gap by short high frequency (RF) high voltage high intensity pulses, so that the instability does not have the time to develop. Once a pulse is switched off, dissipative processes suppress the development of the instability. If the pulse repetition period is comparable to the energy relaxation time in the plasma, its period-averaged parameters, including the degree of ionization, will be quasi stable. In one illustrative embodiment, the pulse had a frequency of about 1–20 MHz, a duration of about 1 msec, and a peak-to-peak voltage of about 1000–10000 volts. In one illustration, the duty cycle ($t_1/t_2$) of the packet waveform was approximately $\frac{1}{11}$.

Use of the packet waveform is beneficial. Because the efficiency of ionization of the plasma ionization device 11 is directly proportional to the voltage supply duty cycle, drive circuit 22 consumes less power (proportional to duty cycle) to provide the pulsed waveform versus the continuous waveform. Further, the service lifetime of the ionization device 11 increases by a factor of 5 to 10 times when the ionization device is powered with a pulsed packet waveform.

With either continuous or packet waveform, a sufficient RF voltage will be developed across electrodes 14 and 16 to cause the local gas to electrically discharge and form a plasma. An advantage of operating the source driver 420 (see FIG. 23) with a pulse width modulated signal is the generation of ion packets 445 as opposed to a continuous stream of ions. This "packetized" transfer of ions 445 allows for the detector processor 430 to use, for example, a synchronous detection technique as applied to packets of filtered ions that arrive at the detector. A synchronous detection technique can measure at a given frequency and phase to yield a high-Q, narrow band filter at, for example, 2 kHz, which is the modulation frequency used at the source driver 420 and provided to the detector processor 430 via the local bus 450. Through use of this synchronous phase detection filter technique, such as in a synchronous filter, the signal-to-noise ratio of ion detection can be improved between about 40 dB and 60 dB. Other processing techniques to further improve the gain or provide other advantages can be employed through the use of other DSP analysis or analog techniques.

Figure 29:
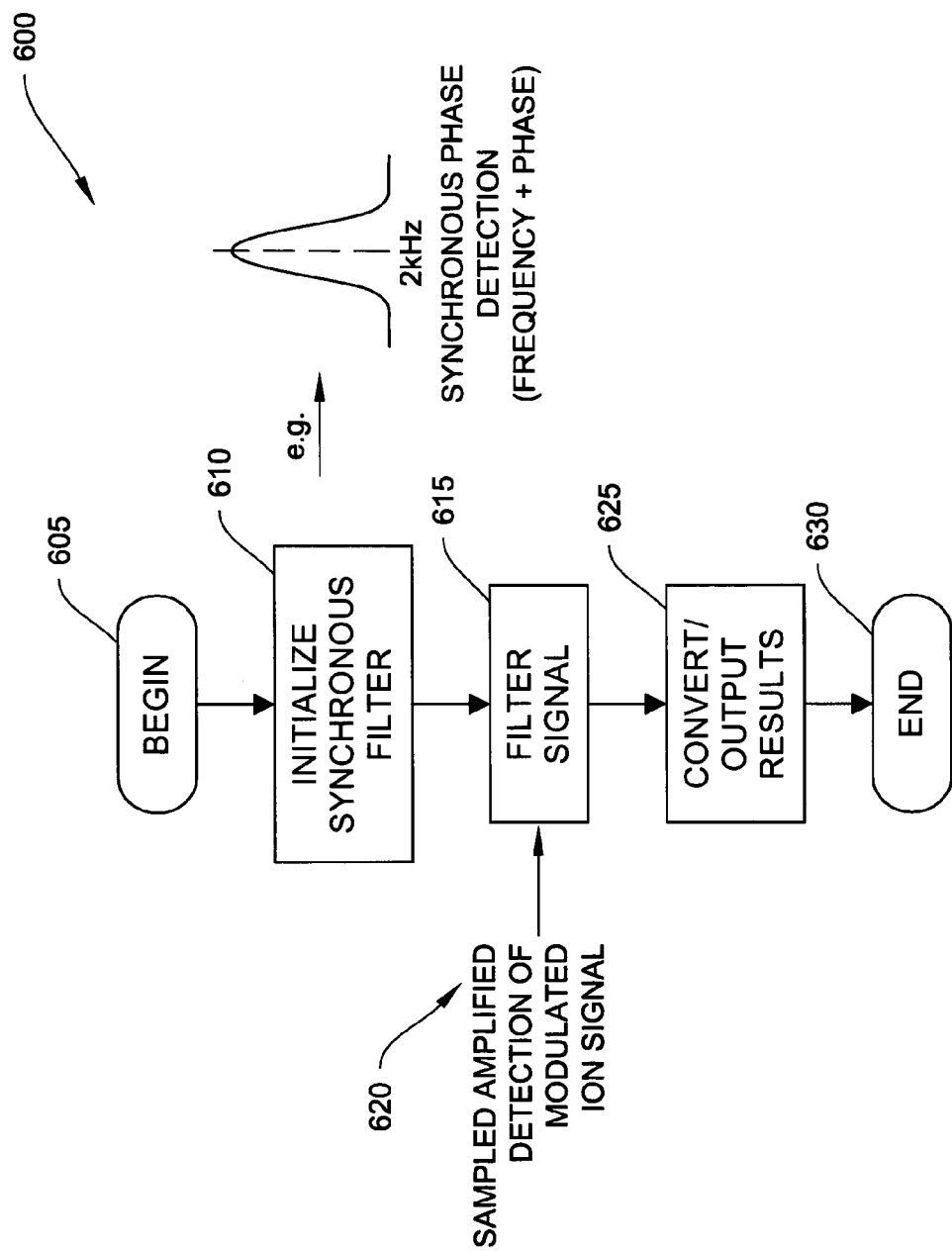
FIG. 29 is a flow diagram of an illustrative process for measure the ions of FIG. 28.

FIG. 29 is a flow diagram of an example process for execution in the DSP 510 for detecting the ion packets 445 just discussed. The process 600 begins (step 605) when the detector processor 430 is turned on. A filter, such as provided with the above synchronous phase detection filter technique discussed above, is initialized (step 610) based on predetermined parameters. The sampled amplified detection of the modulated ion signal 620 is filtered (step 615), and the DSP 510 may convert and/or output the results (step 625) to a display or in a communication signal to another processor, such as a data collection or managerial-type processor. The results may also be used as feedback to a circuit that controls the generation of the plasma; for example, the results may be used to control the duty cycle applied to the plasma to increase or decrease the amount of ions 445 generated by the ionization source 445 for improved and/or dynamic compensation of same.

Figure 30:
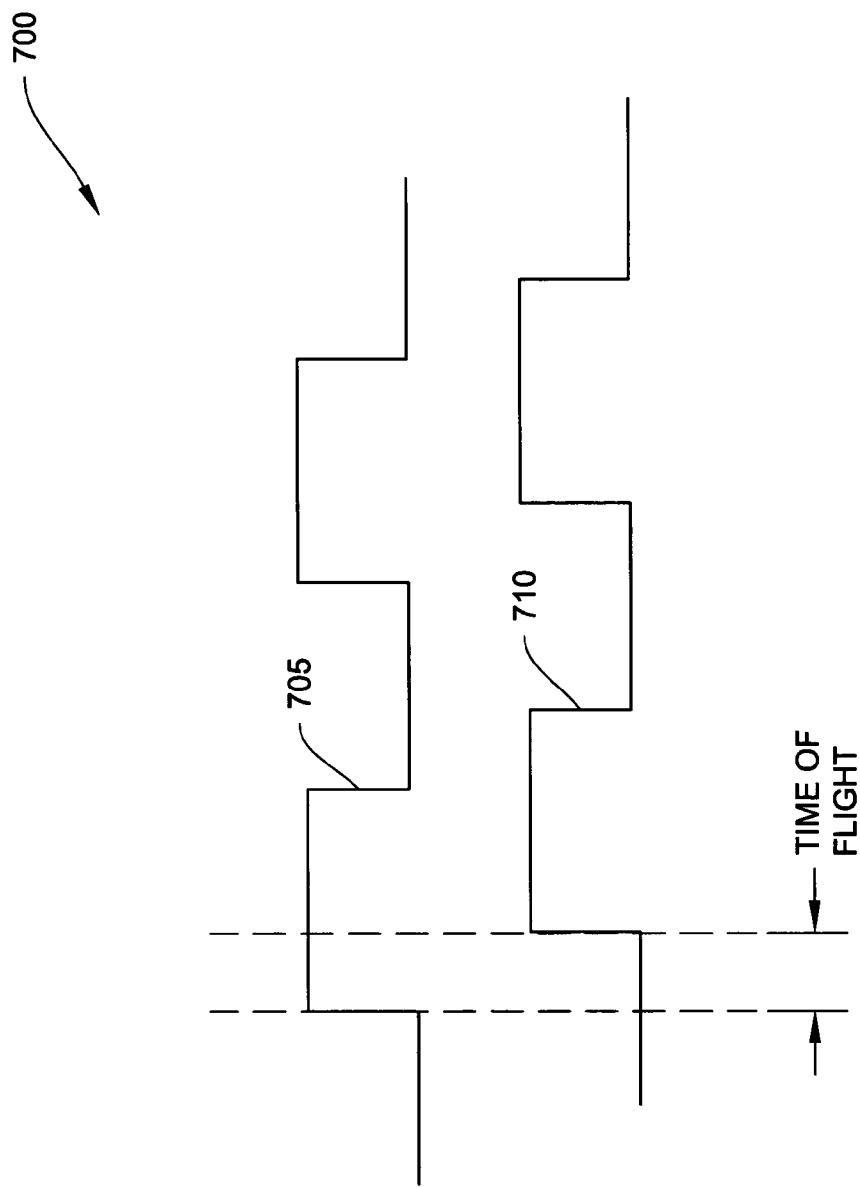
FIG. 30 is a timing diagram indicating an illustrative time of flight for the ions of FIG. 28.

Because of the packetized nature of the ion production, other information may also be gleaned through use of this technique. For example, in the embodiment 700 of FIG. 30, a waveform of the drive signal 705 and detection signal 710 can be compared against one another in the DSP on the rising edge or falling edge to determine a "time of flight" (TOF) of the ions from the ionization source 405 to the detector 415, which provides useful detection information like that obtained in known TOF ion mobility spectrometers. A DMS filter drive according to an illustrative embodiment of the invention will now be discussed. There is a need for efficient DMS filter drive circuit designs as may be desirable for faster and more reliable operation, especially in the context of hand-held and battery-operated applications. Moreover, traditional designs typically exhibit poor efficiency due to the effects of both parasitic and load capacitances. As discussed below, the invention, in various illustrative embodiments, overcomes these deficiencies.

In the illustrative embodiment of FIG. 23, the filter driver 425 provides excitation to the electrodes 412a and 412b of the DMS filter 410. The excitation includes RF voltage and compensation. A preferred DMS system of the invention is driven as taught in U.S. Provisional Patent Application Ser. No. 60/498093, incorporated herein by reference, wherein filter driver 425 uses a low duty cycle (e.g., less than or equal to about 20%), high voltage (greater than or equal to about 1500 volts to peak), and high frequency (e.g., greater than or equal to about 1 MHz) signal applicable to ion filtering.

This results in power consumption less than or equal to about 1 watt. By comparison, a common DMS filter driver applies an RF voltage having 1500 Vpp to the filter electrodes 412 and which in one embodiment translates into about 13 Watts of power required to operate system 400. At 13 Watts of power, the system 400 uses more power than desirable for long periods of hand-held usage and raises heat dissipation issues.

In a low power practice of the invention, the filter driver 425 takes advantage of parasitic capacitances in transformers within the circuit through the use of a resonant reset technique to generate a high voltage pulse during the flyback cycle. In addition to this technique, a specially designed low capacitance planar transformer may be used to drive the capacitive load (i.e., filter electrodes 412) of the DMS filter 410.

Advantages provided through use of this design include, for example,: operating the circuit from a low voltage DC (e.g., 20 volts) source; employing a small geometry, low voltage MOSFET transistor to cause the fly-back switching of the transformer(s); using low cost components; sensing voltages on the low voltage primary side of the transformer (s) such that no high voltage resistors or capacitors are needed; achieving very efficient (< or = about 1 W) in power consumption; and tuning the circuit for operation at different frequencies. In one DMS embodiment, about 1500 volt operation at about 800 KHz using only about 750 mW is achieved, whereas traditional circuit types use > about 10 W.

Figure 31:
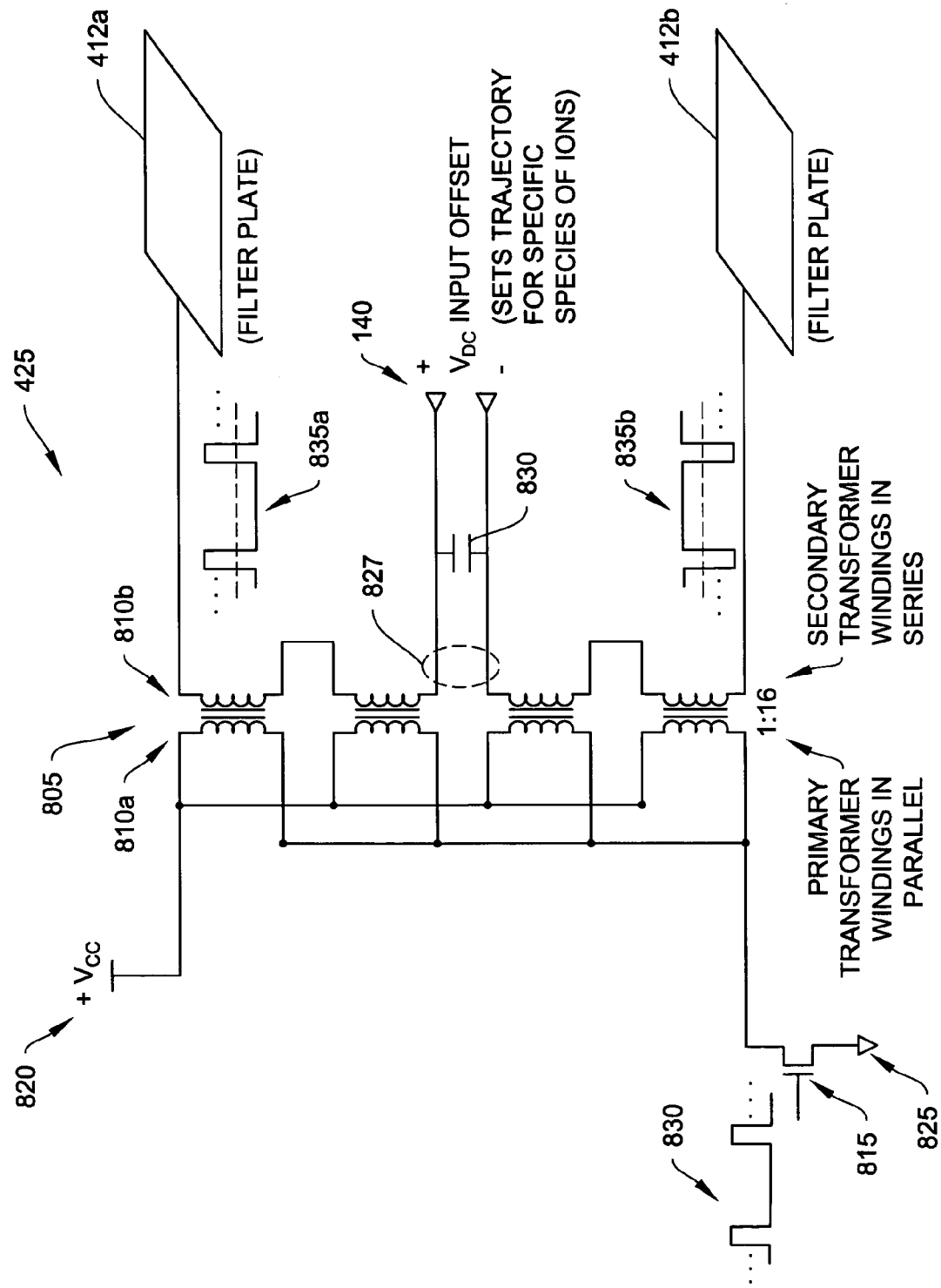
FIG. 31 is a generalized schematic diagram of an illustrative filter driver for the system of FIG. 23.

FIG. 31 is a generalized schematic diagram for a filter driver 425 according to an illustrative embodiment of the invention. In this embodiment, four transformers 805 are arranged to provide power to the filter electrodes 412a and 412b. Primary transformer windings 810a of the transformers 805 are connected together in a parallel arrangement. One end of the primary transformer windings 810a is connected to Vcc, and the other end of the primary transformer windings 810a is connected to a power return 825 through a MOSFET transistor 815.

Secondary transformer windings 810b of the transformers 805 are connected together in a series arrangement. At a location 827 between the secondary transformer windings 810b, a set of inputs 140 is provided to present a DC offset to the filter electrodes 412 via the secondary windings 810b. A capacitor 830 is included to facilitate application of the DC offset.

Figure 32:
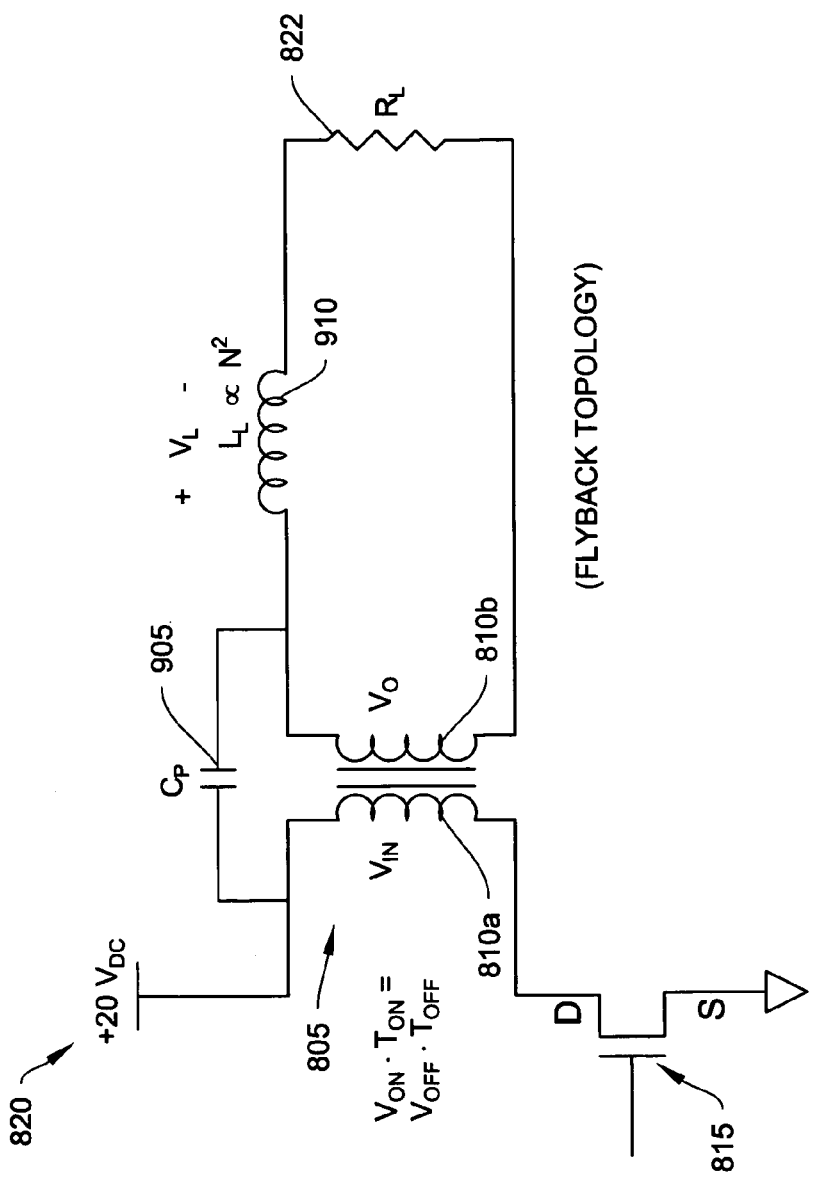
FIG. 32 is a generalized schematic diagram depicting parasitic capacitance and leakage inductance associated with the transformers of the circuit of FIG. 31.

FIG. 32 illustrates the leakage inductances and parasitic capacitances associated with the transformers 805 to aid in understanding the operation of the filter driver 425 when used in the fly-back configuration of FIG. 31. Referring to FIG. 32, a parasitic capacitor (Cp) 905 spans between the primary transformer windings 810a and secondary transformer windings 810b. A leakage inductor 910 is connected in series between the secondary windings 810b and a load resistance 822.

The value of the leakage inductance 910 is proportional to the square of the turns. In operation, the leakage inductance 910 causes a voltage drop when power is transferred from the secondary transformer windings 810b to the load resistance 822. In previous designs that used only a single transformer 805, fewer primary turns are used to minimize the value of the leakage inductance 910, thereby minimizing voltage drop across it. The problem is that fewer primary turns results in more current experienced in the primary transformer windings 810a and in the drain-to-source path in the MOSFET 815. Because of the higher current, higher current rated elements, such as inductor wire and MOSFET devices, must be employed. However, through use of the parallel arrangement of the primary windings 810a and series arrangement of the secondary transformer windings 810b, as shown in FIG. 31, a lower amount of leakage inductance 910 is experienced.

In other words, in the traditional filter driver 425, a single transformer results in a dramatic increase of leakage inductance 910, such as by a factor of 16. Meanwhile, because of the parallel/series arrangement of the primary transformer windings 810a and secondary transformer windings 810b, respectively, the increase in leakage inductance 910 is considerably less, such as only increased by a factor of four with four transformers 805 to produce the same output voltage as the prior, single transformer design.

Moreover, in typical applications, the voltage gain across a transformer is generally desired to be less than or equal to about 4:1, where $V_0/V_{in}$ is proportional to $N_{secondary}$. In the ion filtering application at hand where a pair of filter electrodes 412 are being driven, the voltage gain is approximately 16:1. This gain is consistent with the parallel/series designed discussed above.

The parasitic capacitance 905 is used to further increase the transformer gain in that the MOSFET 815 can be switched at a rate that matches the oscillation frequency experienced between the primary transformer windings 810a and parasitic capacitance 905. In this way, the voltage differential between VCC 820 and power return can be made lower (e.g., 20V rather than 200V) and still produce the necessary output voltage for driving the filter electrodes 412 at a level sustaining proper operation, i.e., filtering of the ion packets system 445 (FIG. 23).

Figure 33:
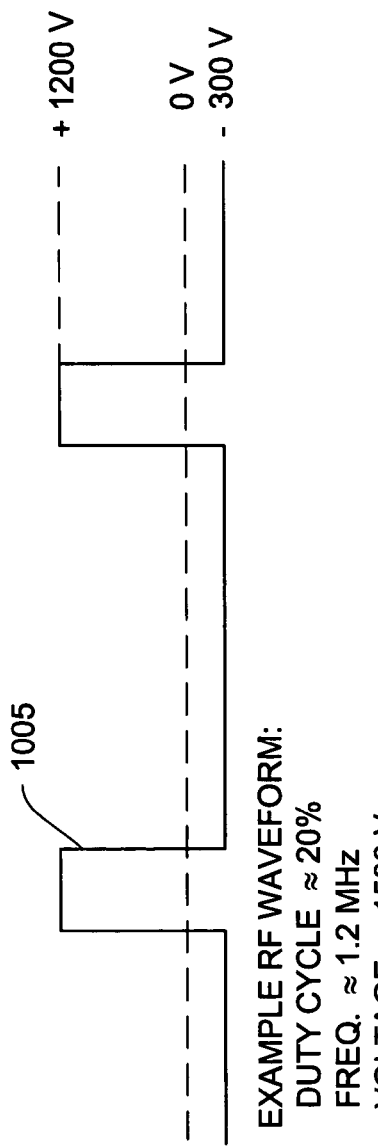
FIG. 33 is an a graph of an RF waveform exemplary of the type produced by the circuit of FIG. 31.

FIG. 33 is an example RF waveform 1005 used to drive the filter electrodes 412. The waveform 1005 has a duty cycle of approximately 20% on and operates at a frequency of about 1.2 MHz, with peak-to-peak voltages of approximately 1500 Vpp. This waveform tracks an input signal 830 (FIG. 31) provided to the gate of the MOSFET 815, where the waveform 1005 is shown in FIG. 31 as a differential drive signal 835a and 835b presented to respective filter electrodes 412a and 412b.

Figure 34:
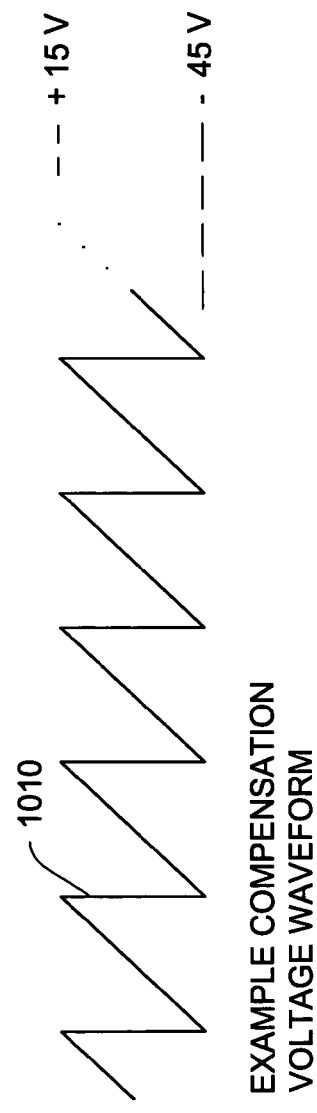
FIG. 34 is a graph of an exemplary low frequency, compensation voltage waveform for modulating the RF waveform of FIG. 33.

FIG. 34 depicts a waveform (e.g., sawtooth waveform) 1010 that is used to provide the compensation voltage applied to the DC offset input location 827 (FIG. 31) in the secondary transformer windings 810b. The waveform 1010, in this embodiment, has a peak positive voltage of about +15V, a peak negative voltage of about −45V, and a user selectable frequency of, for example, about one scan about every four to twenty seconds, optionally corresponding to a user display. Such a waveform is designed to properly filter the ions in the ion packets system 445, produced by the ionization source 405, traveling through the filter 410 to the detector 415. Based on the types of ions traveling through the filter 410, which is a function of the plasma source 435 and sample 140 under test, the compensation voltage waveform 1010 may be changed in shape, frequency, and/or voltage range. A feedback arrangement may be provided, where the detector processor 430 may have some optimization processes that provide feedback to the filter driver 425 to automatically adjust the characteristics of the compensation voltage waveform 1010.

Figure 35:
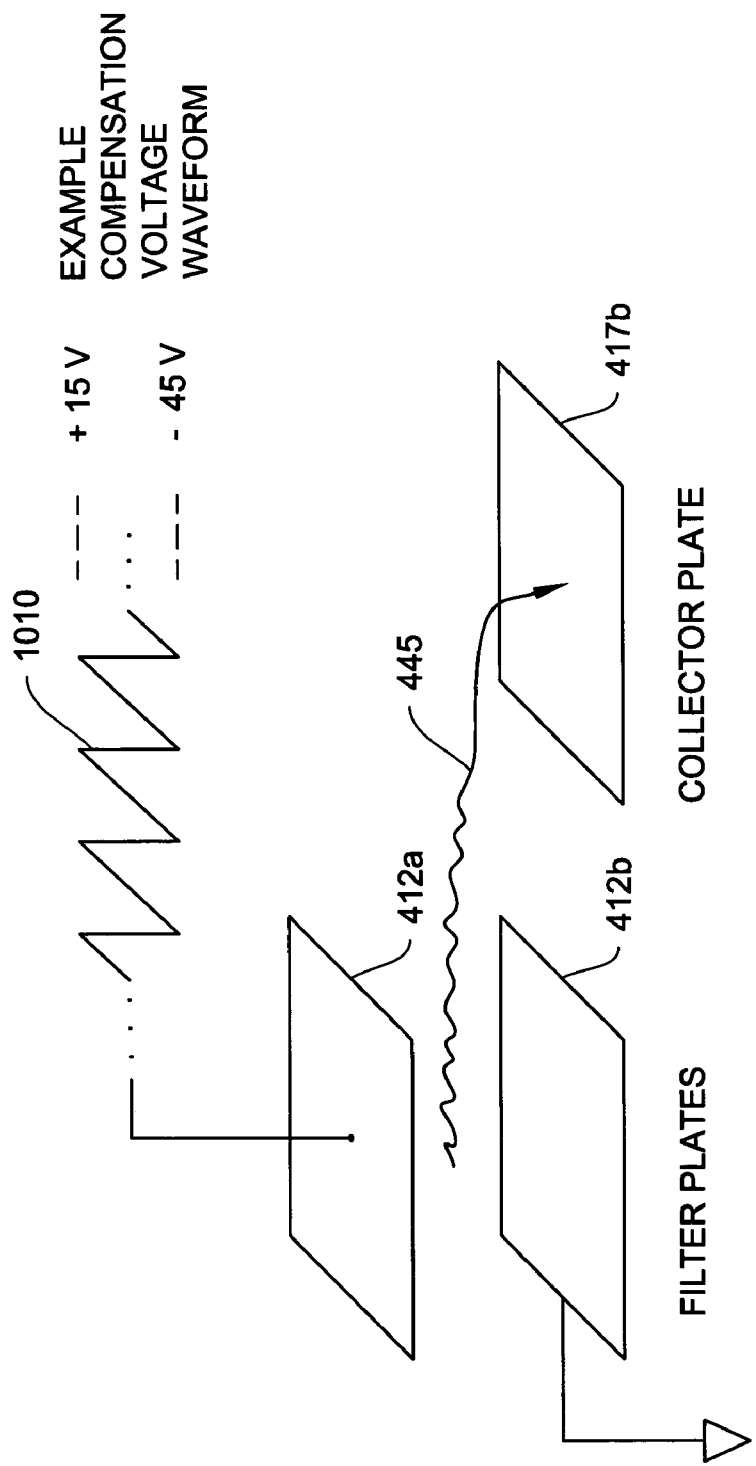
FIG. 35 is a diagram of a filter and detector of a type that may be employed in the system of FIG. 23 and having a compensation voltage of the type depicted in FIG. 34 applied to the filter.

FIG. 35 is a graphical diagram of the ion packet system 445 traveling between the filter electrodes 412a. The example compensation voltage waveform 1010 is applied to the filter electrodes 412, causing the ion packets system 445 to oscillate between the plates. Ions system 445 not having characteristics compatible with the compensation voltage waveform 1010 "drop-off" from the ion packets system 445. The ion system 445 that pass through the filter electrodes 412 contact the collector plate 417b.

Beyond the circuit improvements discussed above, improvements to the transformers themselves may also be used to improve overall filter driver 425 performance.

Figure 36A:
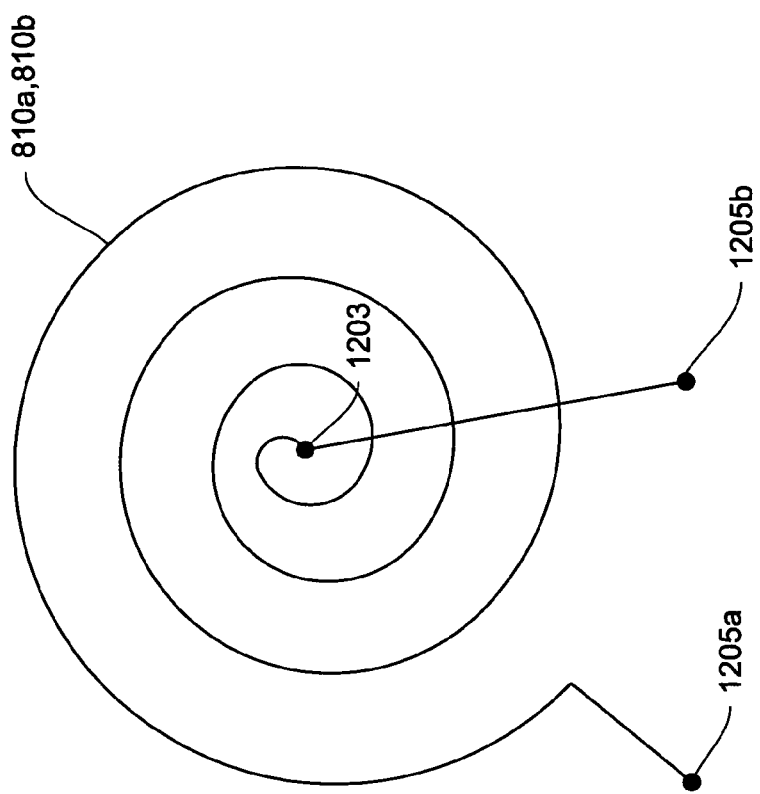
FIG. 36A is a top view of a circuit board trace used to implement a primary or secondary winding in the transformers of FIG. 31.

FIG. 36A is an example of one such improvement, where a top view of a helical shape is shown. The helical shape provides the primary and secondary transformer windings 810a and 810b of the transformers 805. A first connection point 1205a may be connected to the voltage source VCC 820, and a secondary connection point 1205b may be connected to the MOSFET 815, as discussed in reference to the primary transformer windings 810a of FIG. 31.

Continuing to refer to FIG. 36A, the helical windings may be implemented on a printed circuit (PC) board that inherently has a high withstand voltage (i.e., arcing is prevented for up to very high voltages). The high withstand voltage transformer is an improvement over traditional toroidally wound transformers that use transformer wire that has a lower withstand voltage for a similar cost of materials. In addition, the printed circuit board has a smaller physical size than toroidally wound transformers and can be made through less expensive automatic production techniques.

Figure 36B:
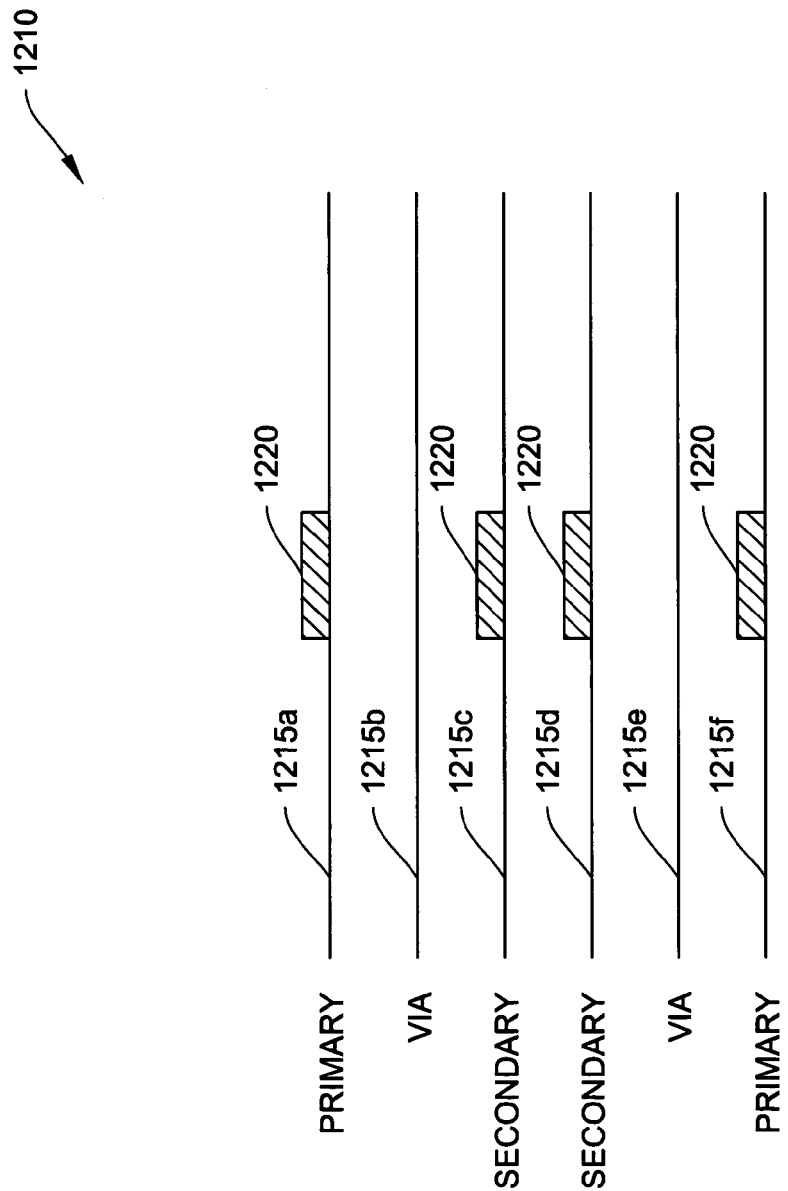
FIG. 36B is a cross-sectional view of a circuit board layering diagram having indications of traces used to implement the primary and secondary windings of the transformers of FIG. 31.

Referring to FIG. 36B, a cross-sectional view of a six-layer printed circuit board 1210 of the helical shape of the windings 810a, 810b is shown. The printed circuit board 1210 includes layers 1215a, 1215b, . . . , 1215f with traces 1220 used to implement the helical design of FIG. 36A. The primary transformer windings 810a are printed on the outside layers 1215a and 1215f in this embodiment, and the secondary transformer windings 810b are printed on the two innermost layers 1215c and 1215d. The layers without the traces 1220 (i.e., layers 1215b and 1215e) provide layers where the center point 1203 of the helical design (FIG. 36A) is routed from the center to the connection point 1205b. A full circuit board 1210 supports a single or multiple transformers, depending on the size of the circuit board 1210. For example in one implementation, a 1"×1" square circuit board supports a single transformer 805.

With the topology of FIG. 36B, a build-up of capacitance (i.e., capacitance is proportional to the trace area divided by the distance between the traces) is incurred, which causes inefficiency in the operation of the transformers 805. So, in order to reduce this capacitance, a different layout may be employed, shown in FIG. 37.

FIG. 37 is a top view of a layout of the primary transformer windings 810a and secondary transformer windings 810b. The windings 810 are concentric spirals, where, in this embodiment, the primary transformer windings 810a are "within" the secondary transformer windings 810b. Mechanically, the traces 1220 on a 6-layer circuit board 1210 may be on different layers 1215a, 1215f, 1215c, 1215d, and "via" layers 1215b, 1215e may support extension of the center points 1203 and 1303, to the respective connection points 1205b and 1305b. Traces to the other connection points 1205a and 1305a may be on one of the via layers or windings layers.

In operation, coupling between the outer concentric winding (e.g., secondary transformer winding 810b) and a center magnetic core (discussed later in reference to FIG. 38) is reduced due to an increased distance between the windings and the center magnetic core. However, this loss is less than increases resulting from offsetting the traces 1220 composing the primary and secondary windings 810a and 810b, which reduces capacitance therebetween.

Figure 38:
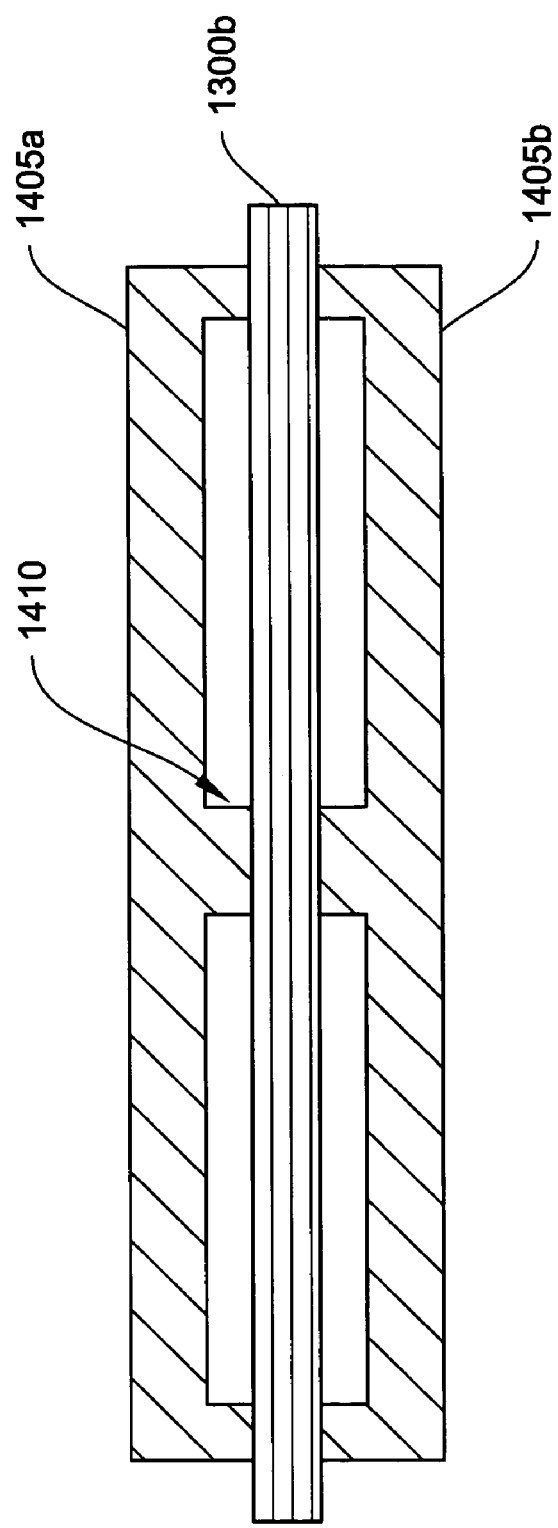
FIG. 38 is a mechanical diagram of a transformer of FIG. 31 implemented in a circuit board using the techniques discussed with respect to FIGS. 35–37.

FIG. 38 is an example of the 6-layer circuit board 1300b of FIG. 36B that is sandwiched between a magnet having first and second components 1405a and 1405b. These components 1405 have a central peg, which may be about ¼" in diameter. The central peg 1410 feeds through the circuit board 1300b, and, consequently, in the center of the helical transformer windings 810a and 810b, as just described, to form a transformer adapted to meet the performance metrics discussed above.

While this invention has been particularly shown and described with reference to several embodiments, it should be understood that various changes in form and details may be made herein without departing from the scope of the invention encompassed by the appended claims.

As can be seen from the above discussion, plasma sources according to the invention are useful in a wide range of systems that require sample ionization. The invention may be provided as a stand-alone device or may be incorporated into a larger system that can benefit from a clean and stable source of ions. Examples of such systems include DMS systems, ion mobility spectrometers, and atmospheric chemical pressure ionization spectrometers, among others. However, practices of the invention are not limited to analytical purposes, and in fact, the invention has many practical applications too numerous to list herein.

What is claimed is:

1. Apparatus for analysis of chemical compounds, the apparatus comprising:
   a. capacitive discharge plasma generator for generating a plasma,
   b. a sample ionizer for ionizing a sample, said sample ionizer being enabled by said plasma, and
   c. a sample analyzer for analyzing said ionized sample.

2. Apparatus of claim 1 wherein said analyzer is for providing an analytical electric field for analyzing ions associated with said ionized sample, said analyzing being based on aspects of the mobility of said associated ions in said analytical field.

3. Apparatus of claim 2 wherein said plasma generator includes a pair of electrodes separated by a gap, wherein said plasma generator is for generating a plasma between said electrodes in said gap, and wherein at least one of said electrodes is protected from contact with said plasma.

4. Apparatus of claim 2 further including a material layer associated with said at least one electrode for protecting the surface of said at least one electrode from contact by said plasma.

5. Apparatus of claim 4 wherein said material layer includes a dielectric.

6. Apparatus of claim 2 wherein said plasma is formed in air and said plasma generation includes formation of positive and negative ions simultaneously at atmospheric pressure.

7. Apparatus of claim 2 wherein said sample ionization includes formation of positive and negative sample ions simultaneously.

8. Apparatus of claim 7 wherein said analyzer includes a differential ion mobility filter.

9. Apparatus of claim 8 further including a dual electrode detector, wherein said differential ion mobility filter analyzes said positive and negative sample ions simultaneously and passes positive and negative ions of interest to said detector, wherein said detector detects said positive and negative ions of interest simultaneously.

10. Apparatus of claim 1 wherein said plasma generator defines a plasma field region, wherein said plasma is formed in said plasma field region and said sample is ionized outside of said plasma field region.

11. Apparatus of claim 10 further comprising a flow path for carrying a gas and a sample, wherein said plasma generator is for ionizing said gas and generates ionization media and by-products, further comprising a separator wherein said ionization media is separated from said by-products, and wherein said sample ionizer ionizes said sample with said separated ionization media.

12. Apparatus of claim 11, wherein said plasma generator defines a first location in said flow path where said plasma is formed from said gas in said field, wherein ionization media is generated in said plasma field, and wherein said sample ionizer defines a second location in said flow path where said sample is ionized with said ionization media, wherein said sample ionization is isolated from said plasma formation.

13. Apparatus of claim 12 wherein said plasma generator is for operation on a plasma gas flow and said sample ionizer is for operation on a sample gas flow, wherein said ionization media flows counter to said plasma gas flow into said sample gas flow.

14. Apparatus of claim 12 wherein said ionization media includes photons and by-products, wherein said photons are separated from said by-products and flow into said sample ionizer to photo-ionize said sample.

15. Apparatus of claim 10 wherein said plasma generator generates photons and said sample is ionized with said photons outside of said plasma field region.

16. Apparatus of claim 10 wherein said ionization media includes photons and said sample is photo-ionized.

17. Apparatus of claim 16 wherein said sample ionizer is isolated from said plasma generator by a gas flow.

18. Apparatus of claim 10 further comprising a flow path for carrying a gas and a sample,
   a. wherein said plasma generator is for ionizing said gas, wherein said ionizing of said gas generates ionization media and by-products, and
   b. wherein said flow path enables (1) a flow of said by-products in said plasma field region in away from said sample ionizer, and (2) a flow of said ionization media out of said plasma field region and into said sample ionizer, and
   c. wherein said sample is ionized in said sample ionizer by said ionization media outside of said plasma field region and away from said by-products.

19. Apparatus of claim 18 wherein said flow path further enables a flow of said gas into said plasma generator and enables a flow of said sample into said sample ionizer.

20. Apparatus of claim 10 wherein said plasma generator includes a pair of electrodes separated by a gap, wherein said plasma generator is for generating a plasma between said electrodes in said gap, and wherein at least one of said electrodes is protected from contact with said plasma.

21. Apparatus of claim 20 further including a material layer associated with said at least one electrode for protecting the surface of said at least one electrode from contact by said plasma.

22. Apparatus of claim 10 wherein said gas is air at atmospheric pressure.

23. Apparatus of claim 10 wherein said plasma includes formation of positive and negative ions simultaneously.

24. Apparatus of claim 23 wherein said sample ionization includes formation of positive and negative sample ions simultaneously.

25. Apparatus of claim 24 wherein said analyzer analyzes said positive and negative sample ions simultaneously.

26. Apparatus of claim 10 wherein said analyzer is for providing an analytical electric field for analyzing ions associated with said ionized sample, said analyzing being based on aspects of the mobility of said associated ions in said analytical field.

27. Apparatus of claim 1 further comprising a flow path, said flow path having at least first and second flow channel parts, wherein said first channel part is for a first process, wherein said sample is processed in said first part, wherein said sample is ionized based on aspects of said plasma generation and ions of said ionized sample are processed in said second part, wherein said sample analyzer characterizes said sample based on said first and said second process.

28. Apparatus of claim 27 wherein said parts are aligned in series in said flow path.

29. Apparatus of claim 27 wherein said parts are aligned in parallel in said flow path.

30. Apparatus of claim 27 wherein said flow path is for carrying a gas and a sample, wherein said plasma generator is for ionizing said gas for generating ionization media, and wherein said first process includes ionizing said sample with said ionization media.

31. Apparatus of claim 27 wherein said plasma includes formation of positive and negative ions simultaneously.

32. Apparatus of claim 31 wherein said first flow channel part includes a flow outlet, wherein said sample ions are generated in said first flow channel part and include both positive and negative sample ions, wherein said sample ions are transported along said first flow channel part toward said outlet, further comprising an ion deflector, wherein selected ions of said positive and negative sample ions are deflected from said first flow channel part into said second flow channel part by said in deflector.

33. Apparatus of claim 32, wherein said selected and deflected sample ions are processed in said second flow channel part by said sample analyzer.

34. Apparatus of claim 33 wherein said sample analyzer characterizes said sample based on said processing in said second flow channel part of said selected and deflected sample ions.

35. Apparatus of claim 27 wherein said first flow channel part includes a flow outlet, wherein said sample ions are generated in said first flow channel part and include both positive and negative sample ions, and wherein said sample ions are transported along said first flow channel part toward said flow outlet.

36. Apparatus of claim 35 further comprising an ion deflector, wherein selected ions of said positive and negative sample ions are deflected from said first flow channel part into said second flow channel part by said in deflector, wherein said selected and deflected sample ions are processed in said second flow channel part, and wherein said sample analyzer characterizes said sample based on said selected and deflected sample ions.

37. Apparatus of claim 27 wherein said second part includes a device for filtering said sample ions based on aspects of ion mobility in an electric field.

38. Apparatus of claim 27 further comprising a drive controller, wherein said apparatus has a plurality of flow channels, wherein each said channel is for processing an ionized compound, wherein said processing is controlled by said controller.

39. Apparatus of claim 38 wherein each said flow channel has an associated sample ionizer, wherein each said sample ionizer ionizes said sample at a level selected by said drive controller.

40. Apparatus of claim 27 further including an inlet in said flow path for receipt of a dopant, said dopant flowing in said plasma generator to affect said plasma generation.

41. Apparatus of claim 27 further including an inlet in said flow path for receipt of a dopant, said dopant flowing in said sample ionizer to affect said sample ionization.

42. Apparatus of claim 27 further including an inlet in said flow path for receipt of a dopant, said dopant flowing in said sample analyzer to affect said analyzing of said ionized sample.

43. Apparatus of claim 27 further comprising a plasma drive controller, wherein said plasma may be generated at selected energy levels for generation of ions, where said sample ionizer ionizes said sample at a level selected by said drive controller.

44. Apparatus of claim 27 wherein said plasma generator is for direct ionization of a gas and said sample ionizer is for photo-ionization of said sample, wherein said plasma generator generates photons, wherein some of said photons pass directly from said generator to said ionizer, said direct passing being unfiltered by intervening material.

45. Apparatus of claim 44 wherein said analyzer is for providing an analytical electric field for analyzing ions associated with said ionized sample, said analyzing being based on aspects of the mobility of said associated ions in said analytical field.

46. Apparatus of claim 1 further including an input for receipt of a dopant, said dopant flowing in said plasma generator to affect said plasma generation.

47. Apparatus of claim 46 wherein said analyzer is for providing an analytical electric field for analyzing ions associated with said ionized sample, said analyzing being based on aspects of the mobility of said associated ions in said analytical field.

48. Apparatus of claim 1 further including an input for receipt of a dopant, said dopant flowing in said sample ionizer to affect said sample ionization.

49. Apparatus of claim 48 wherein said analyzer is for providing an analytical electric field for analyzing ions associated with said ionized sample, said analyzing being based on aspects of the mobility of said associated ions in said analytical field.

50. Apparatus of claim 1 further including an input for receipt of a dopant, said dopant flowing in said sample analyzer to affect said analyzing of said ionized sample.

51. Apparatus of claim 50 wherein said analyzer is for providing an analytical electric field for analyzing ions associated with said ionized sample, said analyzing being based on aspects of the mobility of said associated ions in said analytical field.

52. Apparatus of claim 1 further comprising a drive controller, wherein said plasma generating is controlled by said controller, said controller including a modulation circuit for generating a modulated drive signal for driving said generating.

53. Apparatus of claim 52 wherein said modulation circuit drives said modulated drive signal for producing ions in packets.

54. Apparatus of claim 53 wherein said packets have a frequency related to said modulated drive signal and have an average intensity linearly controlled by said modulated drive signal.

55. Apparatus of claim 54 wherein said analyzer is for providing an analytical electric field for analyzing ions associated with said ionized sample, said analyzing being based on aspects of the mobility of said associated ions in said analytical field.

56. Apparatus of claim 55 wherein said analyzer detects said packets synchronously according to said modulated drive signal.

57. Apparatus of claim 53 wherein said plasma is driven by a transformer and said modulation circuit operates said transformer at resonance with a peak-to-peak voltage of sufficient amount to produce said packets.

58. Apparatus of claim 1 further comprising a drive controller, wherein said plasma generating is controlled by said controller, further comprising a device for measuring said plasma, said controller regulating said plasma according an input from said device for measuring.

59. Apparatus of claim 58 wherein said device for measuring measures photo-intensity of said plasma.

60. Apparatus of claim 58 wherein said device for measuring measures the spectral output of said plasma generator.

61. Apparatus of claim 58 wherein said device for measuring measures photo-intensity of said plasma.

62. Apparatus of claim 1 further comprising a drive controller, wherein said plasma generating is controlled by said controller, further comprising a device for introducing a dopant to said plasma generator, said controller regulating said plasma according the amount of said dopant introduced by said device.

63. Apparatus of claim 1 further comprising a drive controller, wherein said plasma generating is controlled by said controller, further comprising a device for measuring water vapor in said plasma generator, said controller regulating said plasma according the amount of said water vapor measured by said device.

64. Apparatus of claim 1 wherein said plasma generator generates ions in a flow path and includes an electrode in said flow path.

65. Apparatus of claim 64 wherein said electrode is isolated from contact with said plasma.

66. Apparatus of claim 65 wherein said electrode is isolated by a dielectric material.

67. Apparatus of claim 64 wherein said electrode is isolated from contact with said plasma.

68. Apparatus of claim 64 wherein said electrode is isolated from contact with said sample.

69. Apparatus of claim 1 wherein said plasma generator generates ions in a flow path and includes a pair of electrodes in said flow path.

70. Apparatus of claim 69 wherein the pair of electrodes are substantially external to said flow path.

71. Apparatus of claim 1 wherein said electrodes are isolated from contact with said sample by a gas flow.

* * * * *